(12) United States Patent
Brea Fernandez et al.

(10) Patent No.: US 11,052,044 B2
(45) Date of Patent: Jul. 6, 2021

(54) IN SITU LIPID SYNTHESIS FOR PROTEIN RECONSTITUTION

(71) Applicant: The Regents of the University of California, Oakland, CA (US)

(72) Inventors: Roberto Javier Brea Fernandez, San Diego, CA (US); Christian Cole, Del Mar, CA (US); Neal K. Devaraj, La Jolla, CA (US); Brent Lyda, San Diego, CA (US); Roger Sunahara, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/489,783

(22) PCT Filed: Mar. 1, 2018

(86) PCT No.: PCT/US2018/020512
§ 371 (c)(1),
(2) Date: Aug. 29, 2019

(87) PCT Pub. No.: WO2018/160876
PCT Pub. Date: Sep. 7, 2018

(65) Prior Publication Data
US 2020/0022915 A1 Jan. 23, 2020

Related U.S. Application Data

(60) Provisional application No. 62/466,236, filed on Mar. 2, 2017.

(51) Int. Cl.
| | | |
|---|---|---|
| *A61K 9/127* | (2006.01) | |
| *C07F 9/10* | (2006.01) | |
| *C07H 15/14* | (2006.01) | |
| *C07K 14/705* | (2006.01) | |

(52) U.S. Cl.
CPC ............ *A61K 9/1277* (2013.01); *A61K 9/127* (2013.01); *C07F 9/106* (2013.01); *C07H 15/14* (2013.01); *C07K 14/705* (2013.01)

(58) Field of Classification Search
CPC ....... A61K 9/1277; A61K 9/127; C07F 9/106; C07H 15/14; C07K 14/705
See application file for complete search history.

(56) References Cited

U.S. PATENT DOCUMENTS

2010/0129433 A1* 5/2010 Kasai ..................... A61K 9/127
424/450

OTHER PUBLICATIONS

Cole, C.M., et al Angew Chem 54, p. 12738-12742, 2015.*
Mehta., S et al in J Am Chem Soc. 116, 1569-1570, 1994.*
Bosch, M.P. et al. (Jul. 29, 2004). "Synthesis and biological activity of new potential agonists for the human adenosine A2A receptor," *J Med Chem* 47(16):4041-4053, 1 page Supplementary Data.
Brea, R.J. et al. (Dec. 15, 2014, e-published Oct. 24, 2014). "In situ vesicle formation by native chemical ligation," *Angew Chem Int Ed Engl* 53(51):14102-14105.

(Continued)

*Primary Examiner* — Gollamudi S Kishore
(74) *Attorney, Agent, or Firm* — Mintz, Levin, Cohn, Ferris, Glovsky and Popeo, P.C.

(57) ABSTRACT

Described herein, inter alia, are compositions and methods useful for the reconstitution of membrane proteins.

15 Claims, 13 Drawing Sheets

(56) References Cited

OTHER PUBLICATIONS

Brea, R.J. et al. (Aug. 2, 2016, e-published Jul. 20, 2016). "Nonenzymatic biomimetic remodeling of phospholipids in synthetic liposomes," *PNAS USA* 113(31):8589-8594.

Cole, C.M. et al. (Oct. 2015, e-published Aug. 28, 2015). "Spontaneous Reconstitution of Functional Transmembrane Proteins During Bioorthogonal Phospholipid Membrane Synthesis," *Angew Chem Int Ed Engl* 54(43):12738-12742.

International Search Report dated Jun. 27 2018, for PCT Application No. PCT/US2018/020512, filed Mar. 1, 2018, 4 pages.

Mitra, N. et al. (Mar. 15, 2013, e-published Jan. 30, 2013). "Calcium-dependent ligand binding and G-protein signaling of family B GPCR parathyroid hormone 1 receptor purified in nanodiscs," *ACS Chem Biol* 8(3):617-625.

Olschewski, D. et al. (Jul. 2008, e-published May 27, 2008). "Chemical synthesis and semisynthesis of membrane proteins," *Mol Biosyst* 4(7):733-740.

Thevenin, D. et al. (Dec. 13, 2005,). "Identifying interactions between transmembrane helices from the adenosine A2A receptor," *Biochemistry* 44(49):16239-16245.

Vélez-Ruiz, G. A. et al. (2011). "Reconstitution of G protein-coupled receptors into a model bilayer system: reconstituted high-density lipoprotein particles," *Methods Mol Biol* 756:167-182.

Whorton, M.R. et al. (May 1, 2007, e-published Apr. 23, 2007). "A monomeric G protein-coupled receptor isolated in a high-density lipoprotein particle efficiently activates its G protein," *PNAS USA* 104(18):7682-7687.

Written Opinion dated Jun. 27 2018, for PCT Application No. PCT/US2018/020512, filed Mar. 1, 2018, 6 pages.

\* cited by examiner

Traditional Compounds

DDM

Liposomal preparation
Incubation of proteoliposomes
Dialysis / Bio-Beads

POPC

Micelle Formation

Bilayer Formation

Analogs 1      4

IN SITU LIPID SYNTHESIS FOR PROTEIN RECONSTITUTION

CROSS-REFERENCE TO RELATED APPLICATIONS

This application is a Section 371 US National Phase of International Application No. PCT/US2018/020512 filed Mar. 1, 2018, which claims priority to U.S. Application No. 62/466,236 filed Mar. 2, 2017, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under GM08326, GM106990, and GM083118 awarded by The National Institutes of Health, and under CHE1254611 awarded by The National Science Foundation. The government has certain rights in the invention.

BACKGROUND

Cell transmembrane receptors play a key role in the detection of environmental stimuli and control of intracellular communication. G protein-coupled receptors (GPCRs) constitute the largest transmembrane protein family involved in cell signaling. However, current methods for their functional reconstitution in biomimetic membranes remains both challenging and limited in scope. Disclosed herein, inter alia, are solutions to these and other problems in the art.

BRIEF SUMMARY

In an aspect is a method for forming a lipid membrane including a membrane protein, the method including: (i) solubilizing the membrane protein in a first surfactant to form a first solution; (ii) adding a reactive surfactant including a reactive thioester moiety to the first solution, thereby forming a second solution which includes the reactive surfactant and the membrane protein; (iii) adding a phosphatidylcholine compound to the second solution, thereby forming a synthetic phospholipid; wherein a plurality of the synthetic phospholipids form a lipid membrane including the membrane protein.

In an aspect is a method for forming a lipid membrane including a membrane protein, the method including (i) adding a reactive surfactant comprising a reactive thioester moiety to a first solution which comprises the membrane protein, thereby forming a second solution which comprises the surfactant and the membrane protein; and (ii) adding a phosphatidylcholine compound to the second solution, thereby forming a synthetic phospholipid; wherein a plurality of the synthetic phospholipid form a lipid membrane including the membrane protein.

In another aspect is provided a method for forming a synthetic phospholipid, the method including adding a reactive surfactant including a reactive thioester moiety and a phosphatidylcholine compound to a first solution, thereby forming a synthetic phospholipid.

In an aspect is provided a composition comprising a lipid membrane including a membrane protein and a synthetic phospholipid (e.g., a synthetic phospholid as described herein). In embodiments, the synthetic phospholipid has the formula:

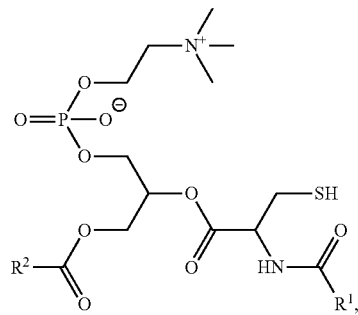

wherein $R^1$ and $R^2$ are independently substituted or unsubstituted alkyl, as described herein, including the embodiments above.

In another aspect is provided an aqueous solution including a membrane protein and a reactive surfactant which includes a reactive thioester moiety. In embodiments, the aqueous solution further includes a non-reactive surfactant (e.g., a nonionic alkyl glucoside). In embodiments, the non-reactive surfactant is n-dodecyl-β-D-maltoside. In embodiments, the membrane protein is a G protein-coupled receptor.

BRIEF DESCRIPTION OF THE DRAWINGS

(FIG. 1A) Model for native chemical ligation (NCL)-based phospholipid membrane formation with embedded $A_{2A}R$. (FIG. 1B) Synthesis of phospholipids by NCL reaction of acyl maltose thioesters and cysteine-functionalized choline-based lysophospholipids.

(FIG. 3A) Phase-contrast microscopy of a $A_{2A}R/3$ proteoliposome formed by NCL. (FIG. 3B) Fluorescence microscopy image of an in situ formed $A_{2A}R/3$ proteoliposome, showing the location of the lipid membrane staining dye Texas Red® DHPE. (FIG. 3C) Fluorescence image corresponding to an in situ formed $A_{2A}R/3$ proteoliposome, showing membrane staining of $A_{2A}R$, which has been previously labeled with Alexa Fluor® 488 dye. The white dashed line corresponds to the intensity profile showed in FIG. 3D. (FIG. 3D) Plot profile showing the fluorescent intensity of a typical membrane stained $A_{2A}R/3$ proteoliposome. The diagonally dashed-line in FIG. 3C represents the section used to make the histogram. Scale bar denotes 5 μm [RFI: relative fluorescence intensity].

(FIG. 4A) [$^3$H]-ZM241385 saturation curves with in situ formed $A_{2A}R/3$ proteoliposomes (blue line) and $A_{2A}R$-HDL reconstituted nanodiscs (orange line). (FIG. 4B) [$^3$H]-ZM241385 (antagonist)/NECA (full agonist) competition with in situ formed $A_{2A}R/3$ proteoliposomes (blue line) and [$^3$H]-NECA saturation curve with $A_{2A}R$-HDL reconstituted nanodiscs (orange line).

FIGS. 13A-13E. (FIG. 13A) Scheme of NCL reaction between a C-18 cysteine lysophospholipid (25) and a C-12 DDM analogue modified with a thioester linkage (26) to produce the membrane forming product (27). (FIGS. 13B-13C) Reconstituted A2a protein that was labeled with a 488 nm NHS-ester dye. The liposome was visualized in phase contrast (FIG. 13B) and fluorescence (FIG. 13C), illustrating membrane staining. (FIG. 13D) Binding assay of A2a with its antagonist ZM241385 after in situ reconstitution and (FIG. 13E) in HDL particles, which is a standard for activity assays. The curves show good agreement only differing in their $EC_{50}$ by +0.06 nM protein. Furthermore, if the lysophospholipid head group is ionic or zwitterionic, then it has a greater potentially of denaturing a protein of interest, thereby abolishing native function.

DETAILED DESCRIPTION

Definitions

Figure 1A:
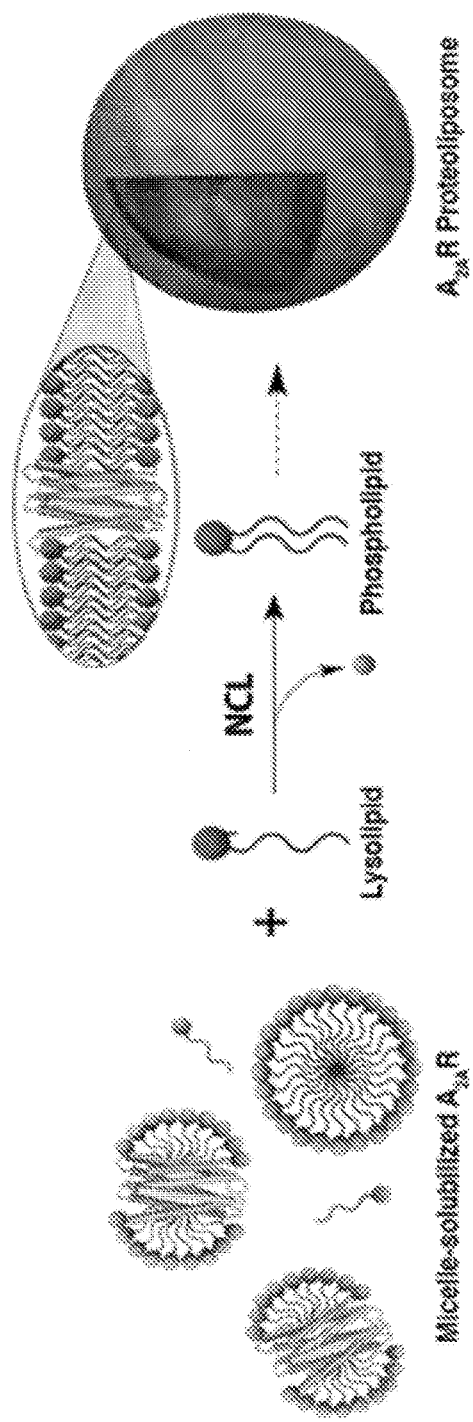
FIGS. 1A-1B. De novo synthesis of phospholipid membranes and concurrent in situ reconstitution of GPCRs.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

The symbol " $\sim\!\sim\!\sim$ " or "-" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

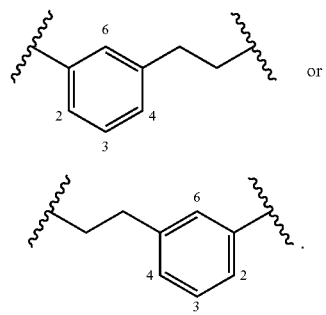

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from: (i) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from: (a) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate" refers to the resulting association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing surfactant, thioester, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, BioConjugate Techniques, Academic Press, San Diego, 1996; and Feeney et al., Modification of Proteins; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; and (m) metal bonding to reactive phosphorus groups (e.g. phosphines) to form, for example, phosphate diester bonds; (n) azides coupled to alkynes using copper catalyzed cycloaddition click chemistry; or (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "synthetic phospholipid" as used herein refers to a phospholipid synthesized ex vivo (e.g., in vitro or in situ). In embodiments, the synthetic lipid membrane is formed following the methods detailed herein.

The term "synthetic lipid membrane" as used herein refers to a lipid membrane assembled ex vivo (e.g., in vitro or in situ). In embodiments, the synthetic lipid membrane is formed following the methods detailed herein.

The term "lipid membrane" is used in accordance with its plain ordinary meaning in the art and refers to a composition comprising a plurality of phospholipids (e.g., phosphoglycerides), glycolipids (e.g., glucosyl-cerebroside), and/or cholesterol. Lipids are amphiphilic and have one end that is soluble in water, referred to as the polar head, (e.g., choline) and another end that is soluble in fat, referred to as the alkyl tail. A lipid bilayer is a type of lipid membrane formed when two layers of lipid molecules arrange such that the polar head (e.g., choline) points towards the exterior solvent and the alkyl chains point inward to form a hydrophobic domain. In embodiments, the lipid membrane is a synthetic lipid membrane.

The term "membrane protein" is used in accordance with its plain ordinary meaning in the art and refers to proteins that interact with, or are part of, lipid membranes. Integral membrane proteins refer to membrane proteins permanently attached to the membrane and are classified according to their interation with the membrane: integral polytopic proteins, also referred to as transmembrane proteins, or integral monotopic proteins (e.g., proteins that are attached to only one side of the membrane and do not span across the membrane). In embodiments, a membrane protein is a transmembrane protein (e.g., a protein which spans across membrane). In embodiments, the membrane protein is a G protein-coupled receptor.

The term "maltoside surfactant" refers to a surfactant comprising a maltose moiety.

The term "phosphatidylcholine" is used in accordance with its plain ordinary meaning and refers to phospholipid which comprise a choline moiety. Typically, a phosphatidylcholine includes a choline containing headgroup and two alkyl chains, one of which is saturated.

The term "micelle" or "micelle composition" refers to an aggregate of molecules in a colloidal solution (e.g., a lipid membrane which organizes in a substantially spherical shape in aqueous solutions). A typical micelle forms a substantially spherical aggregate with the hydrophilic region (e.g., choline) in contact with surrounding solvent, and the hydrophobic alkyl region in the center of the micelle. The lipid content of micelles can vary, thus altering micelle size, stability, solubility, curvature, etc.

The term "nonionic alkyl glucoside" and "alkyl polyglucosides" refers to compound which includes a saccharide moiety (e.g., glucose or maltose) and an alkyl (e.g., $C_6$-$C_{30}$ alkyl) chain. In embodiments, the alkyl chain is substituted with an —OH (e.g., on the terminal carbon). In embodiments, the alkyl chain is unsaturated. In embodiments, the nonionic alkyl glucoside is n-dodecyl-β-D-maltoside.

As used herein "liposomes" are substantially spherical nanoparticles made up of a lipid membrane, i.e., a lipid bilayer. The lipid content of liposomes can vary altering liposome size, stability, solubility, curvature, etc. Examples of lipids include, but are not limited to, a composition described herein (e.g., synthetic phospholipid), cholesterol, phosphatidylcholine (PC) products/derivatives (various carbon chain length fatty acids, saturated, multi-unsaturated and mixed acid PC's); 1,2-dioleoyl-sn-glycero-3-phosphoethanolamine (DOPE); 1,2-dimyristoyl-sn-glycero-3-phosphate (DMPA); 1,2-dipalmitoyl-sn-glycero-3-phosphate (DPPA); 1,2-dioleoyl-sn-glycero-3-phosphate (DOPA); 1,2-dimyristoyl-sn-glycero-3-phospho-(1'-rac-glycerol) (DMPG); 1,2-dipalmitoyl-sn-glycero-3-phospho-(1'-rac-glycerol) (DPPG); 1,2-dioleoyl-sn-glycero-3-phospho-(1'-rac-glycerol) (DOPG); 1,2-dimyristoyl-sn-glycero-3-phosphocholine (DMPC); 1,2-dimyristoyl-sn-glycero-3-phospho-L-serine (DMPS); 1,2-dipalmitoyl-sn-glycero-3-phospho-L-serine (DPPS); 1,2-dioleoyl-sn-glycero-3-phospho-L-serine (DOPC); 1,2-distearoyl-sn-glycero-3-phosphoethanolamine-N-[methoxy(polyethylene glycol)-2000] (DSPE-mPEG-2000); 1,2-di stearoyl-sn-glycero-3-phosphoethanol-amine-N-[folate(polyethylene glycol)-5000](DSPE-mPEG-5000); 1,2-distearoyl-sn-glycero-3-phosphoethanolamine-N-[amino(polyethylene glycol)-2000] (DSPE-PEG-2000); 1,2-stearoyl-3-trimethylammonium-propane (DOTAP); L-α-phosphatidylcholine, hydrogenated (Hydro Soy PC); and 2-stearoyl-sn-glycero-3-phosphocholine (Lyso PC).

Figure 5:
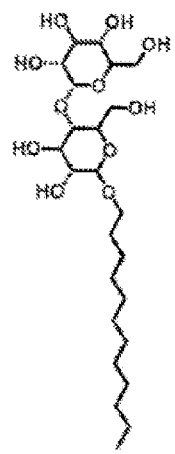
FIG. 5. Reconstitution of $A_{2A}$ protein: traditional method (left) versus NCL-based method (right). The illustration depicts bilayer-forming molecules (bottom) from micellar-forming molecules (top). To reconstitute $A_{2A}$ membrane protein using traditional compounds, first the POPC liposomes would be prepared by rehydrating and tumbling a $N_2$-dried POPC film. Next, micellar $A_{2A}$ protein in DDM would be added and pre-incubated with the liposomes to afford $A_{2A}$/POPC proteoliposomes. This is followed by the removal of the DDM detergent using dialysis or Bio-Beads. To reconstitute $A_{2A}$ membrane protein using in situ NCL reaction, a micelle-solubilized $A_{2A}$ protein containing an acyl maltose thioester (1 or 4) would be added to a cysteine-functionalized lysophospholipid (2 or 5), affording the corresponding $A_{2A}$ proteoliposomes ($A_{2A}$/3 or $A_{2A}$/6).
Figure 5:
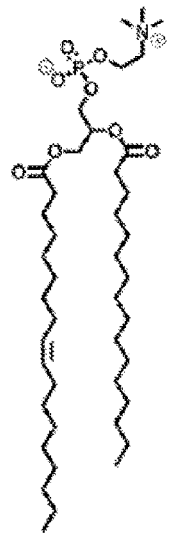
Figure 5:
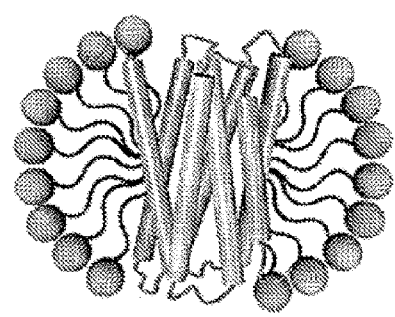
Figure 5:
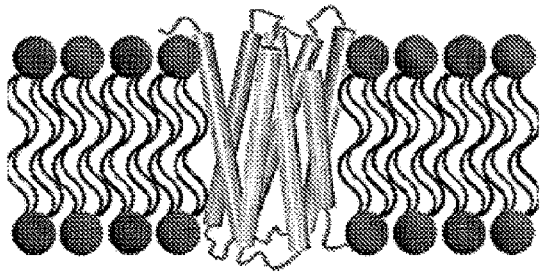
Figure 5:
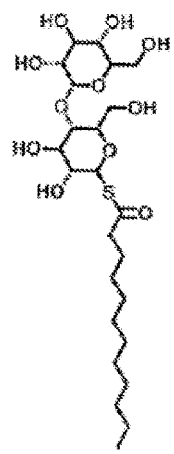
Figure 5:
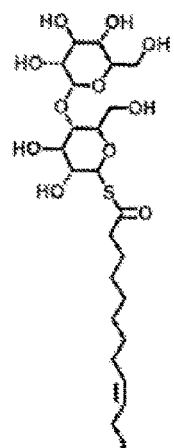
Figure 5:
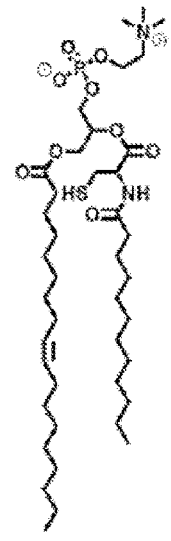
Figure 5:
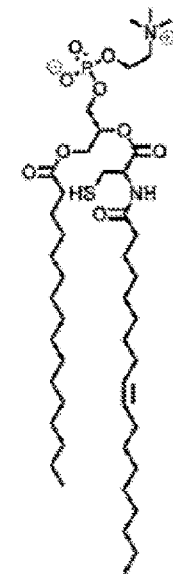

The term "proteoliposome" refers to a liposome have a membrane protein incorporated therein, e.g., as represented by the "bilayer formation" shown in FIGS. 1A and 5.

As used herein "substantially spherical" means an average tendency towards a spherical shape, e.g., a diameter through any axis is roughly equivalent. In embodiments, no diameter differs in length. In embodiments, no diameter differs in length more than about 20% or less from a diameter at any other axis. In embodiments, no diameter differs in length more than about 20% or less from a diameter at any other axis within a substantially spherical shape. In embodiments, no diameter differs in length more than about 15% or less from a diameter at any other axis within a substantially spherical shape. In embodiments, no diameter differs in length more than about 10% or less from a diameter at any other axis within a substantially spherical shape. In embodiments, no diameter differs in length more than about 9% or less from a diameter at any other axis within a substantially spherical shape. In embodiments, no diameter differs in length more than about 8% or less from a diameter at any other axis within a substantially spherical shape. In embodiments, no diameter differs in length more than about 7% or less from a diameter at any other axis within a substantially spherical shape. In embodiments, no diameter differs in length more than about 6% or less from a diameter at any other axis within a substantially spherical shape. In embodiments, no diameter differs in length more than about 5% or less from a diameter at any other axis within a substantially spherical shape. In embodiments, no diameter differs in length more than about 4% or less from a diameter at any other axis within a substantially spherical shape. In embodiments, no diameter differs in length more than about 3% or less from a diameter at any other axis within a substantially spherical shape. In embodiments, no diameter differs in length more than about 3% or less from a diameter at any other axis within a substantially spherical shape. In embodiments, no diameter differs in length more than about 1% or less from a diameter at any other axis within a substantially spherical shape.

As used herein, the term "mean longest dimension" refers to an average of the longest dimension of a substantially spherical object. In some embodiments, the mean longest dimension can be measured by the intensity-averaged particle diameters (Z-average). In some embodiments, the intensity-averaged particle diameters (Z-average) are calculated from the cumulants analysis as defined in ISO 13321 (International Organization for Standardization 1996). In some embodiments, the mean longest dimension can be measured by the number-based particle diameters. In some embodiments, particle size distribution by number is computed from the intensity distribution and the optical properties of the material. There is first-power relationship between particle size and contribution to the distribution.

As used herein, the term "room temperature" or "RT" refers to the temperature of an assay conducted at standard indoor temperature. In embodiments, room temperature refers to an assay conduct without any additional heating or cooling. In embodiments, room temperature is a controlled temperature of about 22-25° C. In embodiments, room temperature is 25° C.

As used herein, the term "phospholipid" or "phospholipids", also called phosphatide or phosphatides, refer to an member of a class of phosphrous- and/or fatty acid-containing substances. In general, phospholipids are composed of a phosphate group, two alcohols, and one or two fatty acids. On one end of the molecule are the phosphate group and one alcohol; this end is polar, i.e., has an electric charge, and is attracted to water (hydrophilic). The other end, which consists of the fatty acids, is neutral; it is hydrophobic and water-insoluble but is fat-soluble. Some non-limiting and illustrative examples of phospholipids include, but not limited to, phosphatidic acid (phosphatidate), phosphatidylcholine (pc) products/derivatives (various carbon chain length fatty acids, saturated, multi-unsaturated and mixed acid PC's); 1,2-dioleoyl-sn-glycero-3-phosphoethanolamine (DOPE); 1,2-dimyristoyl-sn-glycero-3-phosphate (DMPA); 1,2-dipalmitoyl-sn-glycero-3-phosphate (DPPA); 1,2-dioleoyl-sn-glycero-3-phosphate (DOPA); 1,2-dimyristoyl-sn-glycero-3-phospho-(1'-rac-glycerol) (DMPG); 1,2-dipalmitoyl-sn-glycero-3-phospho-(1'-rac-glycerol) (DPPG); 1,2-dioleoyl-sn-glycero-3-phospho-(1'-rac-glycerol) (DOPG); 1,2-dimyristoyl-sn-glycero-3-phosphocholine (DMPC); 1,2-dimyristoyl-sn-glycero-3-phospho-L-serine (DMPS); 1,2-dipalmitoyl-sn-glycero-3-phospho-L-serine (DPPS); 1,2-dioleoyl-sn-glycero-3-phospho-L-serine (DOPC); 1,2-distearoyl-sn-glycero-3-phosphoethanolamine-N-[methoxy(polyethylene glycol)-2000](DSPE-mPEG-2000); 1,2-distearoyl-sn-glycero-3-phosphoethanol-amine-N-[folate (polyethylene glycol)-5000] (DSPE-mPEG-5000); 1,2-distearoyl-sn-glycero-3-phosphoethanolamine-N-[amino (polyethylene glycol)-2000] (DSPE-PEG-2000); 1,2-stearoyl-3-trimethylammonium-propane (DOTAP); L-α-phosphatidylcholine, hydrogenated (Hydro Soy PC); and 2-stearoyl-sn-glycero-3-phosphocholine (Lyso PC), phosphatidylethanolamine, phosphatidylinositol, phosphatidylserine, phosphatidylinositol (PI) phosphatidylinositol phosphate (PIP) phosphatidylinositol bisphosphate (PIP2), phosphosphingolipids and any derivatives thereof.

Figure 9:
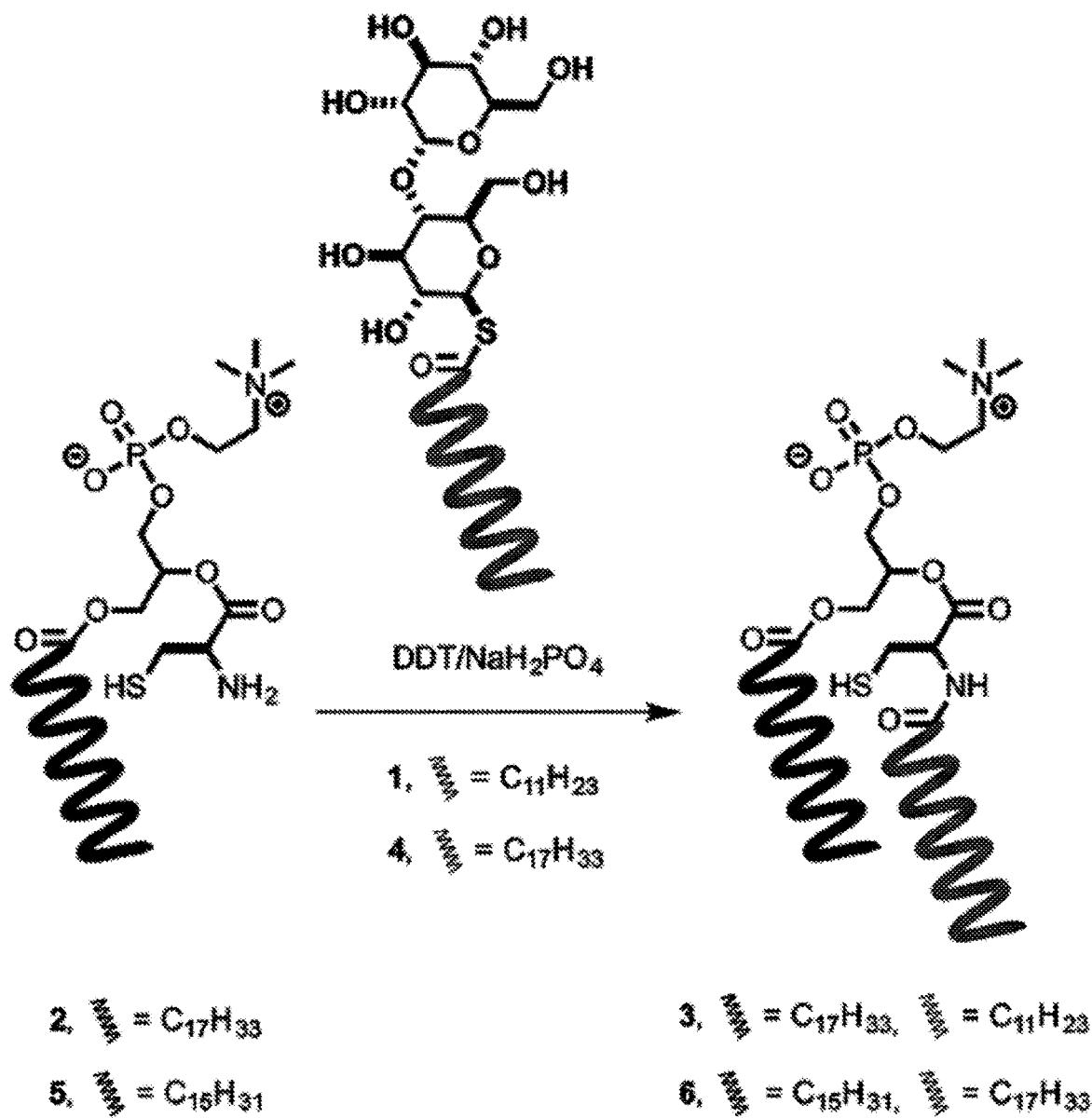
FIG. 9. De novo synthesis of phospholipids (3 or 6) by NCL reaction of an acyl maltose thioester (1 or 4) and a cysteine-functionalized lysophospholipid (2 or 5).

The term "native chemical ligation" as used herein refers to the non-enzymatic and chemoselective coupling of reactants to form a phospholipid (e.g., a maltose thioester 1 and lysophospholipid 2 to yield synthetic phospholipid 3). In native chemical ligation, the thiol group of the phosphatidylcholine compound attacks the C-terminal thioester of a reactive surfactant comprising a reactive thioester moiety (e.g., a maltoside surfactant) as described elsewhere herein, wherein the transthioesterification step is forms an amide bond via a thioester intermediate. Non-limiting examples of native chemical ligation may be found in FIG. 1B, FIG. 9 and FIG. 10.

"Liquid chromatography" and "high pressure liquid chromatography" are used in accordance with their ordinary meaning in analytical chemistry and are techniques used to separate, detect, identify, and quantify each component in a mixture. Liquid chromatography (LC) relies on gravity to allow a mobile phase to pass through a column filled with an adsorbent material. High pressure liquid chromatography (HPLC) relies on a pump to pass a pressured mobile phase through a column filled with an adsorbent material. An HPLC device (HPLC) typically comprises at least the following: a column packed with a suitable stationary phase, a pump for forcing a mobile phase through the column under pressure, and a detector for detecting the presence of compounds eluting from the column. The devices include a means for providing gradient elution, described herein. Routine methods and apparatus for carrying out LC and HPLC separations are well known in the art, and are described, for example, in J. Chromatography, 192:222-227 (1980), J. Liquid Chromatography 4:661-680 (1981), and J. Chromatography, 249:193-198 (1982), the disclosures of which are incorporated by reference herein in their entirety. All the other accessories necessary for carrying out analysis on an LC or HPLC system are well known in the art.

The term "reactive surfactant" as used herein refers to a surfactant that is capable of bonding (e.g., covalent bond or non-covalent bond) to the atoms or molecules of bioconjugate reactive groups (e.g., —$NH_2$). For example, a conjugate between a first bioconjugate reactive group (e.g., —$NH_2$, —COOH, —N-hydroxysuccinimide, or -maleimide) and a reactive surfactant (e.g., sulfhydryl, sulfur-containing surfactant, thioester) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). A reactive surfactant may crosslink with a bioconjugate reactive group (e.g., —$NH_2$). In embodiments, the reactive surfactant includes a thioester (e.g., a thioester capable of reacting with a bioconjugate group). In embodiments, the reactive surfactant includes a reactive thioester.

Methods

In an aspect is a method for forming a lipid membrane including a membrane protein, the method including: (i) solubilizing the membrane protein in a first surfactant to form a first solution; (ii) adding a reactive surfactant including a reactive thioester moiety to the first solution, thereby forming a second solution which includes the reactive surfactant and the membrane protein; (iii) adding a phosphatidylcholine compound to the second solution, thereby forming a synthetic phospholipid; wherein a plurality of the synthetic phospholipids form a lipid membrane including the membrane protein.

In an aspect is a method for forming a lipid membrane including a membrane protein, the method including (i) adding a reactive surfactant comprising a reactive thioester moiety to a first solution which comprises the membrane protein, thereby forming a second solution which comprises the surfactant and the membrane protein; and (ii) adding a phosphatidylcholine compound to the second solution, thereby forming a synthetic phospholipid; wherein a plurality of the synthetic phospholipid form a lipid membrane including the membrane protein.

In embodiments, the plurality of the synthetic phospholipid form a lipid membrane including the membrane protein in the presence of a buffer (e.g., HEPES buffer). In embodiments, the plurality of the synthetic phospholipid form a lipid membrane including the membrane protein in the presence of a buffer (e.g., HEPES buffer), a salt (e.g., NaCl), and a reducing agent (e.g., dithiothreitol (DDT) or tris(2-carboxyethylphosphine) hydrochloride (TCEP-HCl)). In embodiments, the plurality of the synthetic phospholipid form a lipid membrane including the membrane protein in the presence of a HEPES buffer. In embodiments, the plurality of the synthetic phospholipid form a lipid membrane including the membrane protein in the presence of a HEPES buffer, NaCl, and dithiothreitol (DDT). In embodiments, the plurality of the synthetic phospholipid form a lipid membrane including the membrane protein in the presence of a HEPES buffer, NaCl, and tris(2-carboxyethylphosphine) hydrochloride (TCEP-HCl). In embodiments, the plurality of the synthetic phospholipid form a lipid membrane including the membrane protein in the presence of a HEPES buffer, NaCl, dithiothreitol (DDT) and tris(2-carboxyethylphosphine) hydrochloride (TCEP-HCl).

In embodiments, the plurality of the synthetic phospholipid form a lipid membrane including the membrane protein at a pH of about 6.5 to about 8. In embodiments, the plurality of the synthetic phospholipid form a lipid membrane including the membrane protein at a pH of about 6.9 to about 7.5. In embodiments, the plurality of the synthetic phospholipid form a lipid membrane including the membrane protein at a pH of about 7.1 to about 7.5. In embodiments, the plurality of the synthetic phospholipid form a lipid membrane including the membrane protein at a pH of about 7.3 to about 7.5. In embodiments, the plurality of the synthetic phospholipid form a lipid membrane including the membrane protein at a pH of about 7.4.

In embodiments, step (i) is stirred at room temperature for about 20 to 40 minutes. In embodiments, step (i) is stirred at room temperature for about 25 to 40 minutes. In embodiments, step (i) is stirred at room temperature for about 30 to 40 minutes. In embodiments, step (i) is stirred at room temperature for about 20 minutes. In embodiments, step (i) is stirred at room temperature for about 25 minutes. In embodiments, step (i) is stirred at room temperature for about 30 minutes. In embodiments, step (i) is stirred at room temperature for about 35 minutes. In embodiments, step (i) is stirred at room temperature for about 40 minutes.

In embodiments, step (ii) is stirred at room temperature for about 20 to 40 minutes. In embodiments, step (ii) is stirred at room temperature for about 25 to 40 minutes. In embodiments, step (ii) is stirred at room temperature for about 30 to 40 minutes. In embodiments, step (ii) is stirred at room temperature for about 20 minutes. In embodiments, step (ii) is stirred at room temperature for about 25 minutes. In embodiments, step (ii) is stirred at room temperature for about 30 minutes. In embodiments, step (ii) is stirred at room temperature for about 35 minutes. In embodiments, step (ii) is stirred at room temperature for about 40 minutes.

In embodiments, step (iii) is stirred at room temperature for about 20 to 40 minutes. In embodiments, step (iii) is stirred at room temperature for about 25 to 40 minutes. In embodiments, step (iii) is stirred at room temperature for about 30 to 40 minutes. In embodiments, step (iii) is stirred at room temperature for about 20 minutes. In embodiments, step (iii) is stirred at room temperature for about 25 minutes. In embodiments, step (iii) is stirred at room temperature for about 30 minutes. In embodiments, step (iii) is stirred at room temperature for about 35 minutes. In embodiments, step (iii) is stirred at room temperature for about 40 minutes.

In another aspect is provided a method for forming a synthetic phospholipid, the method including (i) adding a reactive surfactant including a reactive thioester moiety and a phosphatidylcholine compound to a first solution, thereby forming a synthetic phospholipid.

In embodiments, the first surfactant is a nonionic alkyl glucoside (e.g., decyl glucoside, sodium lauryl glucose carboxylate, caprylyl capryl glucoside, or dodecyl maltoside). In embodiments, the first surfactant is n-dodecyl-β-D-maltoside.

In embodiments, the first surfactant is decyl glucoside, sodium lauryl glucose carboxylate, caprylyl capryl glucoside, dodecyl maltoside, or a combination of two or more thereof.

In embodiments, the first surfactant is decyl glucoside. In embodiments, the first surfactant is sodium lauryl glucose carboxylate. In embodiments, the first surfactant is caprylyl capryl glucoside. In embodiments, the first surfactant is dodecyl maltoside.

In embodiments, step (ii) includes replacing (e.g., exchanging) the first surfactant with the reactive surfactant in forming the second solution. In embodiments, the first surfactant is replaced for the reactive surfactant comprising a reactive thioester moiety (e.g., compound 1 or compound 4 as described herein), by using a 10 kDa-cutoff spin column.

In embodiments, the reactive surfactant including a reactive thioester moiety is a maltoside surfactant. In embodiments, the maltoside surfactant has the formula:

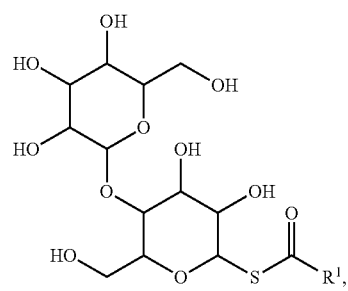

wherein R¹ is a substituted or unsubstituted alkyl.

In embodiments, the phosphatidylcholine compound is a lysophosphatidylcholine compound. In embodiments, the phosphatidylcholine compound has the formula:

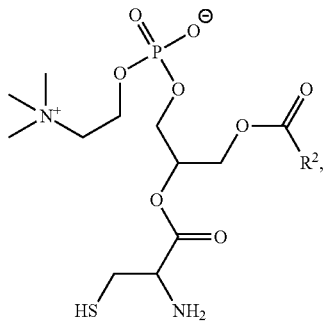

wherein R² is a substituted or unsubstituted alkyl.

Figure 1B:
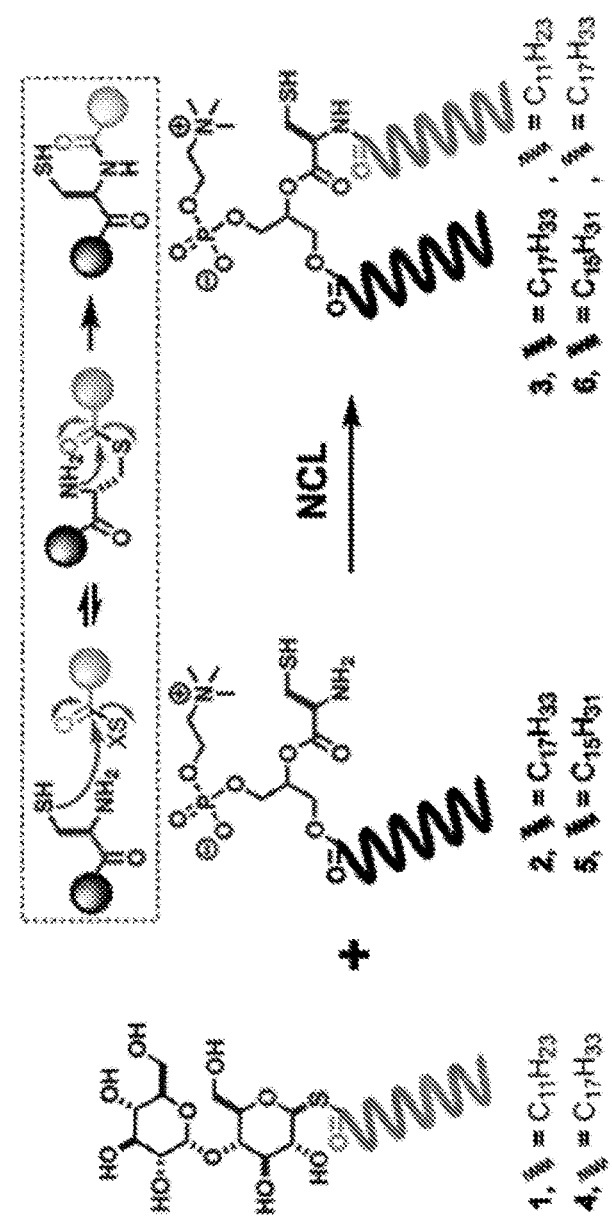
Figure 2:
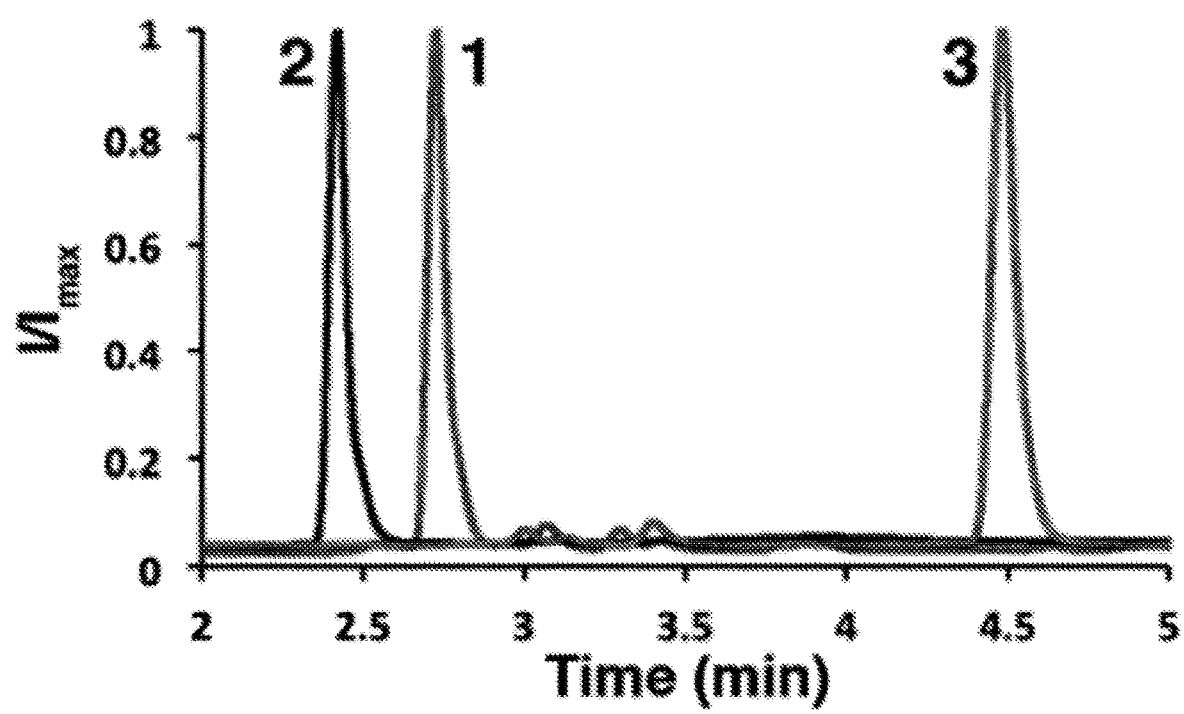
FIG. 2. Monitoring phospholipid formation by HPLC/ELSD/MS. ELSD traces corresponding to the purified dodecanoyl maltose thioester 1, lysolipid 2 and phospholipid 3. The retention times were verified by mass spectrometry and the use of known standards.
Figure 10:
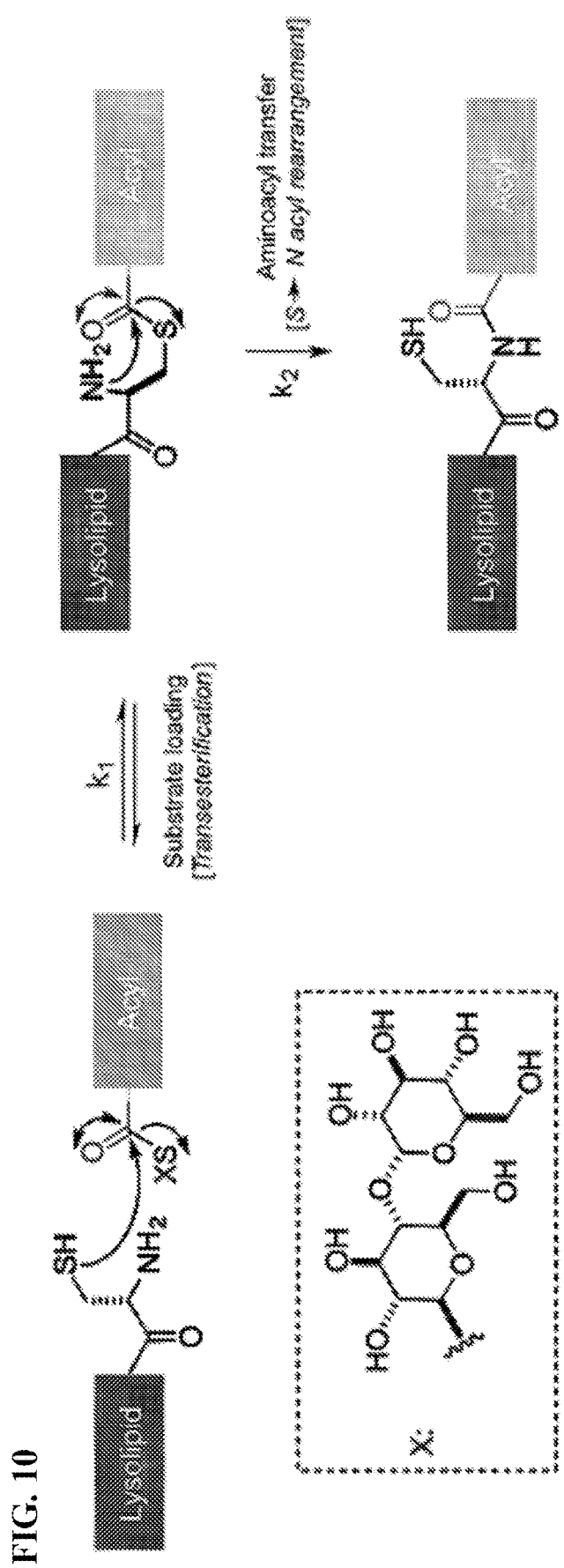
FIG. 10. Mechanism of NCL. The mechanism involves a two-step process consisting of a thiol-exchange step between a C-terminal acyl maltose thioester and the sulfhydryl moiety of an N-terminal cysteine residue in a lysophospholipid, which prompts an intramolecular nucleophilic attack by the α-amino group of the cysteine (S→N acyl rearrangement) to form the final amide bond.
Figure 11A:
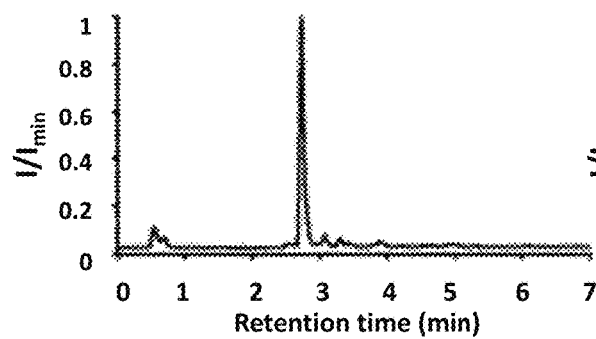
FIGS. 11A-11F. HPLC/ELSD spectra corresponding to dodecanoyl maltose thioester 1 (FIG. 11A), oleoyl maltose thioester 4 (FIG. 11B), lysophospholipid 2 (FIG. 11C), lysophospholipid 5 (FIG. 11D), phospholipid 3 (FIG. 11E) and phospholipid 6 (FIG. 11F). Retention times (tR) were verified by mass spectrometry.
Figure 11B:
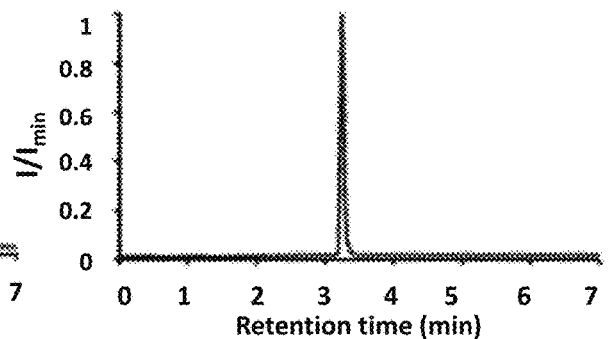
Figure 11C:
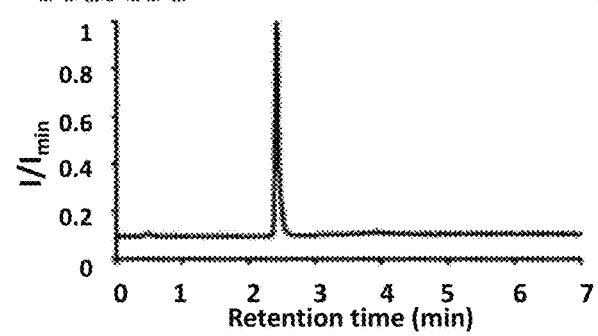
Figure 11D:
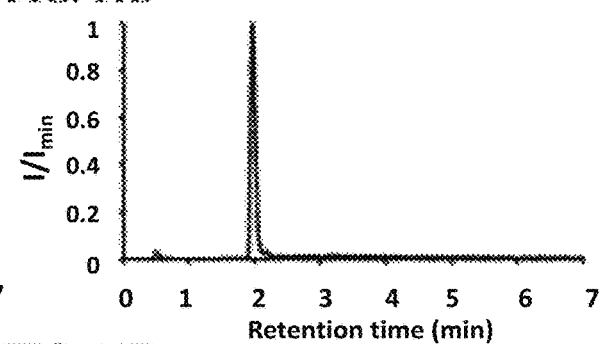
Figure 11E:
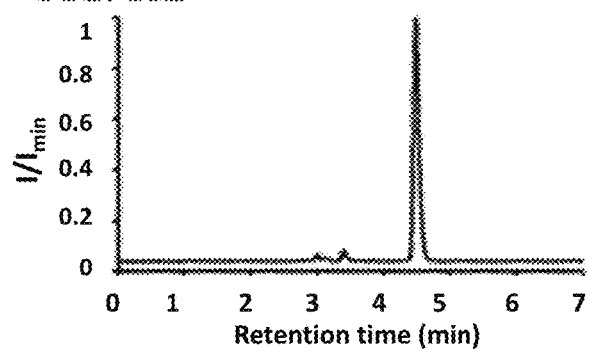
Figure 11F:
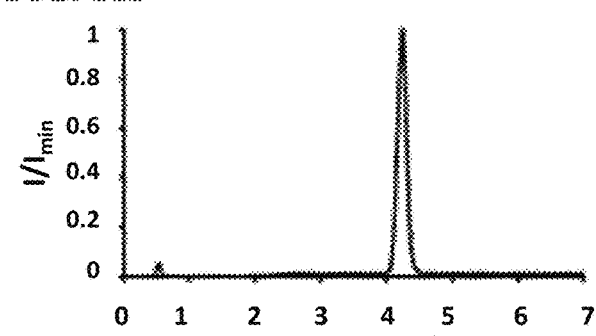
Figure 12:
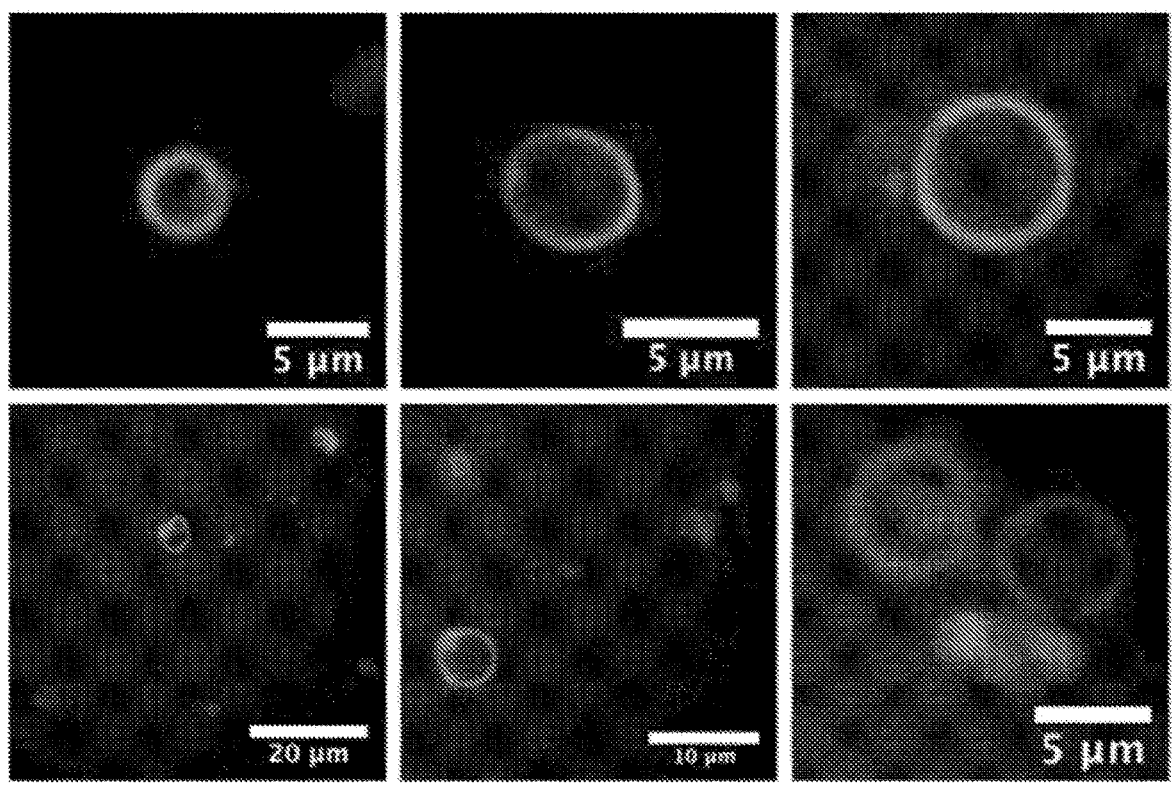
FIG. 12. Spinning-disk confocal microscope images of spontaneously reconstituted $A_{2A}R$/3 proteoliposomes, showing membrane staining of $A_{2A}R$, which has been previously labeled with ALEXA FLUOR® 488 dye.
Figure 13A:
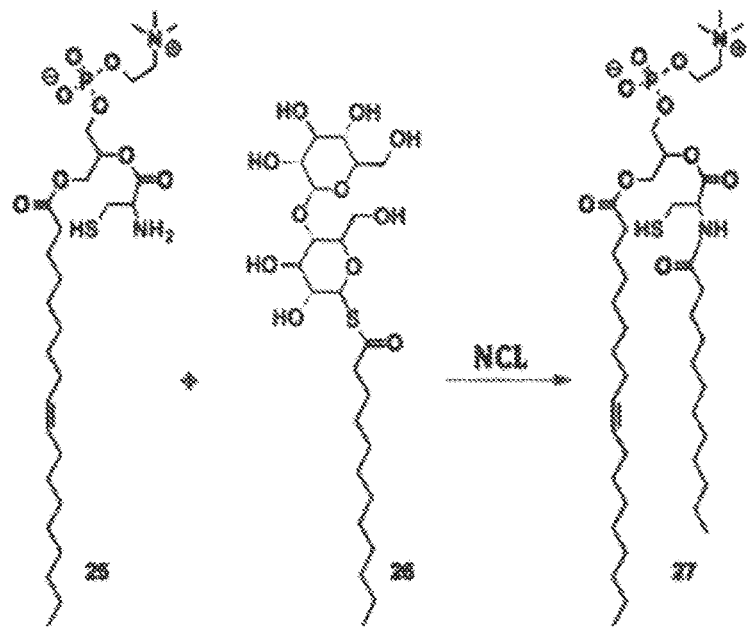
Figure 13A:
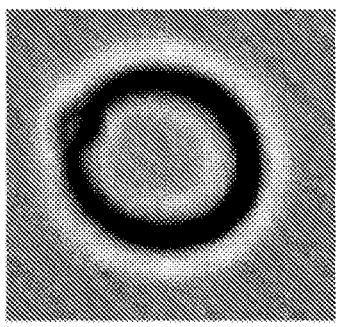
Figure 13A:
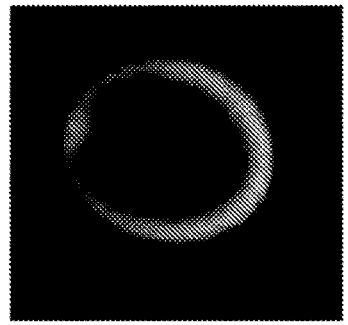
Figure 13A:
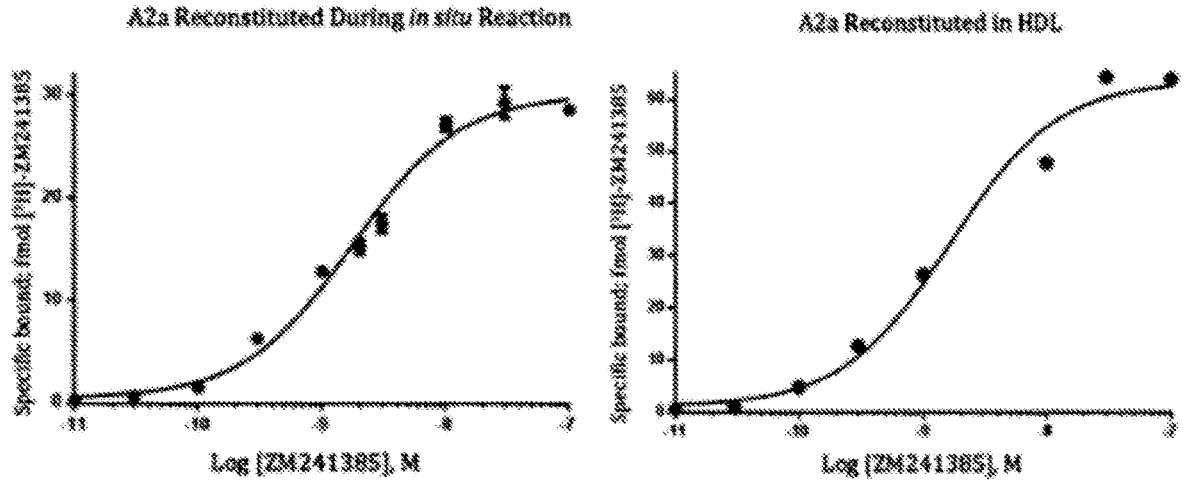

In embodiments, the synthetic phospholipid has the formula:

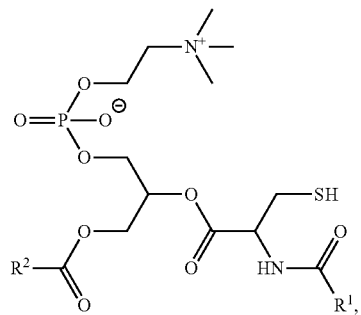

wherein R¹ is a substituted or unsubstituted alkyl. In embodiments, the synthetic phospholipid is the result of a reaction between the maltoside surfactant and the phosphatidylcholine compound as depicted in FIG. 1B or FIG. 10, also referred to herein as native chemical ligation. For example, the synthetic phospholipid is formed via the following reaction, wherein the leaving groups, side products, and counterions are omitted for clarity:

and a hydrophobic alkyl chain (e.g., $C_{10}$ to $C_{30}$ alkyl chain). Typically, variation in the alkyl chain confers a range of properties (e.g., critical micelle concentration and solubility). In embodiments, the first surfactant is n-dodecyl-β-D-maltoside.

In embodiments, the first solution includes dithiothreitol (DDT). In embodiments, the first solution includes tris(2-carboxyethylphosphine) hydrochloride (TCEP-HCl). In embodiments, the first solution includes water. In embodiments, the first solution includes a buffer (e.g., BIS-TRIS (2,2-Bis(hydroxymethyl)-2,2',2"-nitrilotriethanol, 2-Bis(2-hydroxyethyl)amino-2-(hydroxymethyl)-1,3-propanediol, Bis(2-hydroxyethyl)amino-tris(hydroxymethyl)methane), MOPS (3-(N-morpholino)propanesulfonic acid), carbonate, phosphate, HEPES (4-(2-hydroxyethyl)-1-piperazineethanesulfonic acid), or tricine). In embodiments, the first solution includes water. In embodiments, the first solution includes $NaH_2PO_4$. In embodiments, the second solution includes dithiothreitol (DDT). In embodiments, the second solution includes tris(2-carboxyethylphosphine) hydrochloride (TCEP-HCl). In embodiments, the second solution includes water. In embodiments, the second solution includes a buffer (e.g., BIS-TRIS (2,2-Bis(hydroxymethyl)-2,2',2"-nitrilotriethanol, 2-Bis(2-hydroxyethyl)amino-2-(hydroxymethyl)-1,3-propanediol, Bis(2-hydroxyethyl)amino-tris(hydroxymethyl)methane), MOPS (3-(N-morpholino)propanesulfonic acid), carbonate, phosphate, HEPES (4-(2-hydroxyethyl)-1-piperazineethanesulfonic acid), or tricine). In embodiments, the second solution includes $NaH_2PO_4$.

In embodiments, the first solution has a pH of about 6.5 to 7.5. In embodiments, the first solution has a pH of about 7.1 to 7.4. In embodiments, the first solution has a pH of about 6.8 to 7.3. In embodiments, the first solution has a pH of about 6.9 to 7.1. In embodiments, the first solution has a pH of about 6.9. In embodiments, the first solution has a pH of about 7.0. In embodiments, the first solution has a pH of about 7.1. In embodiments, the first solution has a pH of about 7.2. In embodiments, the first solution has a pH of about 7.3. In embodiments, the first solution has a pH of about 7.4. In embodiments, the first solution has a pH of about 7.5.

In embodiments, the second solution has a pH of about 6.5 to 7.5. In embodiments, the second solution has a pH of about 7.1 to 7.4. In embodiments, the second solution has a pH of about 6.8 to 7.3. In embodiments, the second solution

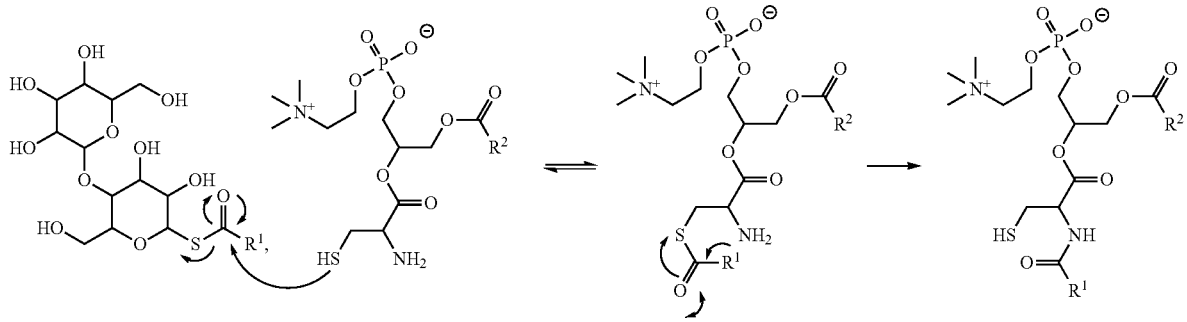

In embodiments, the first surfactant is SDS, Triton X-100, X-114, CHAPS, DOC, NP-40, octyl thioglucoside, octyl glucoside, or dodecyl maltoside. In embodiments, the first surfactant is an alkyl maltoside. Alkyl maltosides represent a class of surfactants which include a hydrophilic maltose has a pH of about 6.9 to 7.1. In embodiments, the second solution has a pH of about 6.9. In embodiments, the second solution has a pH of about 7.0. In embodiments, the second solution has a pH of about 7.1. In embodiments, the second solution has a pH of about 7.2. In embodiments, the second solution has a pH of about 7.3. In embodiments, the second solution has a pH of about 7.4. In embodiments, the second solution has a pH of about 7.5.

In embodiments, the first solution includes water and a buffer (e.g., $NaH_2PO_4$). In embodiments, following the addition of a phosphatidylcholine compound to the second solution, the second solution is stirred under $N_2$ at room temperature (e.g., 20-25° C.). In embodiments, following the addition of a phosphatidylcholine compound to the second solution, the second solution is stirred under $N_2$ at room temperature for about 30 minutes. In embodiments, following the addition of a phosphatidylcholine compound to the second solution, the second solution is stirred under $N_2$ at room temperature for at least 30 minutes. In embodiments, following step (iii) the solution is purified using high performance liquid chromatography (HPLC).

In embodiments, $R^1$ is a substituted or unsubstituted $C_4$-$C_{30}$ alkyl. In embodiments, $R^1$ is a substituted or unsubstituted $C_4$-$C_{20}$ alkyl. In embodiments, $R^1$ is a substituted or unsubstituted $C_6$-$C_{18}$ alkyl. In embodiments, $R^1$ is a substituted or unsubstituted $C_{10}$-$C_{20}$ alkyl. In embodiments, $R^1$ is a substituted or unsubstituted $C_{10}$-$C_{18}$ alkyl. In embodiments, $R^1$ is a substituted or unsubstituted $C_{12}$-$C_{16}$ alkyl. In embodiments, $R^1$ is a substituted or unsubstituted $C_6$-$C_{18}$ alkyl. In embodiments, $R^1$ is a substituted or unsubstituted $C_{10}$-$C_{14}$ alkyl. In embodiments, $R^1$ is a substituted or unsubstituted $C_{16}$-$C_{20}$ alkyl. In embodiments, $R^1$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^1$ is a substituted $C_4$-$C_{30}$ alkyl. In embodiments, $R^1$ is a substituted $C_4$-$C_{20}$ alkyl. In embodiments, $R^1$ is a substituted $C_6$-$C_{18}$ alkyl. In embodiments, $R^1$ is a substituted $C_{10}$-$C_{20}$ alkyl. In embodiments, $R^1$ is a substituted $C_{10}$-$C_{18}$ alkyl. In embodiments, $R^1$ is a substituted $C_{12}$-$C_{16}$ alkyl. In embodiments, $R^1$ is a substituted $C_6$-$C_{18}$ alkyl. In embodiments, $R^1$ is a substituted $C_{10}$-$C_{14}$ alkyl. In embodiments, $R^1$ is a substituted $C_{16}$-$C_{20}$ alkyl. In embodiments, $R^1$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^1$ is an unsubstituted $C_4$-$C_{30}$ alkyl. In embodiments, $R^1$ is an unsubstituted $C_4$-$C_{20}$ alkyl. In embodiments, $R^1$ is an unsubstituted $C_6$-$C_{18}$ alkyl. In embodiments, $R^1$ is an unsubstituted $C_{10}$-$C_{20}$ alkyl. In embodiments, $R^1$ is an unsubstituted $C_{10}$-$C_{18}$ alkyl. In embodiments, $R^1$ is an unsubstituted $C_{12}$-$C_{16}$ alkyl. In embodiments, $R^1$ is an unsubstituted $C_6$-$C_{18}$ alkyl. In embodiments, $R^1$ is an unsubstituted $C_{10}$-$C_{14}$ alkyl. In embodiments, $R^1$ is an unsubstituted $C_{16}$-$C_{20}$ alkyl. In embodiments, $R^1$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^1$ is a substituted or unsubstituted $C_4$-$C_{30}$ alkenyl. In embodiments, $R^1$ is a substituted or unsubstituted $C_4$-$C_{20}$ alkenyl. In embodiments, $R^1$ is a substituted or unsubstituted $C_6$-$C_{18}$ alkenyl. In embodiments, $R^1$ is a substituted or unsubstituted $C_{10}$-$C_{20}$ alkenyl. In embodiments, $R^1$ is a substituted or unsubstituted $C_{10}$-$C_{18}$ alkenyl. In embodiments, $R^1$ is a substituted or unsubstituted $C_{12}$-$C_{16}$ alkenyl. In embodiments, $R^1$ is a substituted or unsubstituted $C_6$-$C_{18}$ alkenyl. In embodiments, $R^1$ is a substituted or unsubstituted $C_{10}$-$C_{14}$ alkenyl. In embodiments, $R^1$ is a substituted or unsubstituted $C_{16}$-$C_{20}$ alkenyl. In embodiments, $R^1$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^1$ is a substituted $C_4$-$C_{30}$ alkenyl. In embodiments, $R^1$ is a substituted $C_4$-$C_{20}$ alkenyl. In embodiments, $R^1$ is a substituted $C_6$-$C_{18}$ alkenyl. In embodiments, $R^1$ is a substituted $C_{10}$-$C_{20}$ alkenyl. In embodiments, $R^1$ is a substituted $C_{10}$-$C_{18}$ alkenyl. In embodiments, $R^1$ is a substituted $C_{12}$-$C_{16}$ alkenyl. In embodiments, $R^1$ is a substituted $C_6$-$C_{18}$ alkenyl. In embodiments, $R^1$ is a substituted $C_{10}$-$C_{14}$ alkenyl. In embodiments, $R^1$ is a substituted $C_{16}$-$C_{20}$ alkenyl. In embodiments, $R^1$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^1$ is an unsubstituted $C_4$-$C_{30}$ alkenyl. In embodiments, $R^1$ is an unsubstituted $C_4$-$C_{20}$ alkenyl. In embodiments, $R^1$ is an unsubstituted $C_6$-$C_{18}$ alkenyl. In embodiments, $R^1$ is an unsubstituted $C_{10}$-$C_{20}$ alkenyl. In embodiments, $R^1$ is an unsubstituted $C_{10}$-$C_{18}$ alkenyl. In embodiments, $R^1$ is an unsubstituted $C_{12}$-$C_{16}$ alkenyl. In embodiments, $R^1$ is an unsubstituted $C_6$-$C_{18}$ alkenyl. In embodiments, $R^1$ is an unsubstituted $C_{10}$-$C_{14}$ alkenyl. In embodiments, $R^1$ is an unsubstituted $C_{16}$-$C_{20}$ alkenyl. In embodiments, $R^1$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^1$ is substituted (e.g., substituted with a substituent group, a size-limited substituent group, or lower substituent group) or unsubstituted alkyl. In embodiments, $R^1$ is unsubstituted alkyl. In embodiments, $R^1$ is an alkyl substituted with a substituent group. In embodiments, $R^1$ is an alkyl substituted with a size-limited substituent group. In embodiments, $R^1$ is an alkyl substituted with a lower substituent group. In embodiments, $R^1$ is unsubstituted alkyl.

In embodiments, $R^1$ is substituted (e.g., substituted with a substituent group, a size-limited substituent group, or lower substituent group) or unsubstituted alkyl. In embodiments, $R^1$ is substituted (e.g., substituted with a substituent group, a size-limited substituent group, or lower substituent group) alkyl. In embodiments, $R^1$ is unsubstituted alkyl. In embodiments, $R^1$ is substituted or unsubstituted alkyl (e.g., $C_6$-$C_{30}$, $C_6$-$C_{24}$, $C_6$-$C_{18}$, or $C_6$-$C_{12}$). In embodiments, $R^1$ is substituted alkyl (e.g., $C_6$-$C_{30}$, $C_6$-$C_{24}$, $C_6$-$C_{18}$, or $C_6$-$C_{12}$). In embodiments, $R^1$ is unsubstituted alkyl (e.g., $C_6$-$C_{30}$, $C_6$-$C_{24}$, $C_6$-$C_{18}$, or $C_6$-$C_{12}$).

In embodiments, $R^1$ is substituted (e.g., substituted with a substituent group, a size-limited substituent group, or lower substituent group) or unsubstituted $C_6$-$C_{30}$ alkyl. In embodiments, $R^1$ is substituted (e.g., substituted with a substituent group, a size-limited substituent group, or lower substituent group) or unsubstituted $C_6$-$C_{30}$ alkyl. In embodiments, $R^1$ is substituted (e.g., substituted with a substituent group, a size-limited substituent group, or lower substituent group) or unsubstituted $C_6$-$C_{24}$ alkyl. In embodiments, $R^1$ is substituted (e.g., substituted with a substituent group, a size-limited substituent group, or lower substituent group) or unsubstituted $C_6$-$C_{18}$ alkyl. In embodiments, $R^1$ is substituted (e.g., substituted with a substituent group, a size-limited substituent group, or lower substituent group) or unsubstituted $C_6$-$C_{12}$ alkyl. In embodiments, $R^1$ is substituted (e.g., substituted with a substituent group, a size-limited substituent group, or lower substituent group) $C_6$-$C_{30}$ alkyl. In embodiments, $R^1$ is substituted (e.g., substituted with a substituent group, a size-limited substituent group, or lower substituent group) $C_6$-$C_{30}$ alkyl. In embodiments, $R^1$ is substituted (e.g., substituted with a substituent group, a size-limited substituent group, or lower substituent group) $C_6$-$C_{24}$ alkyl. In embodiments, $R^1$ is substituted (e.g., substituted with a substituent group, a size-limited substituent group, or lower substituent group) $C_6$-$C_{18}$ alkyl. In embodiments, $R^1$ is substituted (e.g., substituted with a substituent group, a size-limited substituent group, or lower substituent group) $C_6$-$C_{12}$ alkyl. In embodiments, $R^1$ is an unsubstituted $C_6$-$C_{30}$ alkyl. In embodiments, $R^1$ is an unsubstituted $C_6$-$C_{30}$ alkyl. In embodiments, $R^1$ is an unsubstituted $C_6$-$C_{24}$ alkyl. In embodiments, $R^1$ is an unsubstituted $C_6$-$C_{18}$ alkyl. In embodiments, $R^1$ is an unsubstituted $C_6$-$C_{12}$ alkyl.

In embodiments, $R^1$ is a substituted or unsubstituted $C_1$ alkyl. In embodiments, $R^1$ is a substituted or unsubstituted $C_2$ alkyl. In embodiments, $R^1$ is a substituted or unsubstituted $C_3$ alkyl. In embodiments, $R^1$ is a substituted or unsubstituted $C_4$ alkyl. In embodiments, $R^1$ is a substituted or unsubstituted $C_5$ alkyl. In embodiments, $R^1$ is a substituted or unsubstituted $C_6$ alkyl. In embodiments, $R^1$ is a substituted or unsubstituted $C_7$ alkyl. In embodiments, $R^1$ is a substituted or unsubstituted $C_8$ alkyl. In embodiments, $R^1$ is a substituted or unsubstituted $C_9$ alkyl. In embodiments, $R^1$ is a substituted or unsubstituted $C_{10}$ alkyl. In embodiments, $R^1$ is a substituted or unsubstituted $C_{11}$ alkyl. In embodiments, $R^1$ is a substituted or unsubstituted $C_{12}$ alkyl. In embodiments, $R^1$ is a substituted or unsubstituted $C_{13}$ alkyl. In embodiments, $R^1$ is a substituted or unsubstituted $C_{14}$ alkyl. In embodiments, $R^1$ is a substituted or unsubstituted $C_{15}$ alkyl. In embodiments, $R^1$ is a substituted or unsubstituted $C_{16}$ alkyl. In embodiments, $R^1$ is a substituted or unsubstituted $C_{17}$ alkyl. In embodiments, $R^1$ is a substituted or unsubstituted $C_{18}$ alkyl. In embodiments, $R^1$ is a substituted or unsubstituted $C_{19}$ alkyl. In embodiments, $R^1$ is a substituted or unsubstituted $C_{20}$ alkyl. In embodiments, $R^1$ is a substituted or unsubstituted $C_{21}$ alkyl. In embodiments, $R^1$ is a substituted or unsubstituted $C_{22}$ alkyl. In embodiments, $R^1$ is a substituted or unsubstituted $C_{23}$ alkyl. In embodiments, $R^1$ is a substituted or unsubstituted $C_{24}$ alkyl. In embodiments, $R^1$ is a substituted or unsubstituted $C_{25}$ alkyl. In embodiments, $R^1$ is a substituted or unsubstituted $C_{26}$ alkyl. In embodiments, $R^1$ is a substituted or unsubstituted $C_{27}$ alkyl. In embodiments, $R^1$ is a substituted or unsubstituted $C_{28}$ alkyl. In embodiments, $R^1$ is a substituted or unsubstituted $C_{29}$ alkyl. In embodiments, $R^1$ is a substituted or unsubstituted $C_{30}$ alkyl.

In embodiments, $R^1$ is a substituted $C_1$ alkyl. In embodiments, $R^1$ is a substituted $C_2$ alkyl. In embodiments, $R^1$ is a substituted $C_3$ alkyl. In embodiments, $R^1$ is a substituted $C_4$ alkyl. In embodiments, $R^1$ is a substituted $C_5$ alkyl. In embodiments, $R^1$ is a substituted $C_6$ alkyl. In embodiments, $R^1$ is a substituted $C_7$ alkyl. In embodiments, $R^1$ is a substituted $C_8$ alkyl. In embodiments, $R^1$ is a substituted $C_9$ alkyl. In embodiments, $R^1$ is a substituted $C_{10}$ alkyl. In embodiments, $R^1$ is a substituted $C_{11}$ alkyl. In embodiments, $R^1$ is a substituted $C_{12}$ alkyl. In embodiments, $R^1$ is a substituted $C_{13}$ alkyl. In embodiments, $R^1$ is a substituted $C_{14}$ alkyl. In embodiments, $R^1$ is a substituted $C_{15}$ alkyl. In embodiments, $R^1$ is a substituted $C_{16}$ alkyl. In embodiments, $R^1$ is a substituted $C_{17}$ alkyl. In embodiments, $R^1$ is a substituted $C_{18}$ alkyl. In embodiments, $R^1$ is a substituted $C_{19}$ alkyl. In embodiments, $R^1$ is a substituted $C_{20}$ alkyl. In embodiments, $R^1$ is a substituted $C_{21}$ alkyl. In embodiments, $R^1$ is a substituted $C_{22}$ alkyl. In embodiments, $R^1$ is a substituted $C_{23}$ alkyl. In embodiments, $R^1$ is a substituted $C_{24}$ alkyl. In embodiments, $R^1$ is a substituted $C_{25}$ alkyl. In embodiments, $R^1$ is a substituted $C_{26}$ alkyl. In embodiments, $R^1$ is a substituted $C_{27}$ alkyl. In embodiments, $R^1$ is a substituted $C_{28}$ alkyl. In embodiments, $R^1$ is a substituted $C_{29}$ alkyl. In embodiments, $R^1$ is a substituted $C_{30}$ alkyl. In embodiments, $R^1$ is an unsubstituted $C_1$ alkyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl. In embodiments, $R^1$ is an unsubstituted $C_9$ alkyl. In embodiments, $R^1$ is an unsubstituted $C_{10}$ alkyl. In embodiments, $R^1$ is an unsubstituted $C_{11}$ alkyl. In embodiments, $R^1$ is an unsubstituted $C_{12}$ alkyl. In embodiments, $R^1$ is an unsubstituted $C_{13}$ alkyl. In embodiments, $R^1$ is an unsubstituted $C_{14}$ alkyl. In embodiments, $R^1$ is an unsubstituted $C_{15}$ alkyl. In embodiments, $R^1$ is an unsubstituted $C_{16}$ alkyl. In embodiments, $R^1$ is an unsubstituted $C_{17}$ alkyl. In embodiments, $R^1$ is an unsubstituted $C_{18}$ alkyl. In embodiments, $R^1$ is an unsubstituted $C_{19}$ alkyl. In embodiments, $R^1$ is an unsubstituted $C_{20}$ alkyl. In embodiments, $R^1$ is an unsubstituted $C_{21}$ alkyl. In embodiments, $R^1$ is an unsubstituted $C_{22}$ alkyl. In embodiments, $R^1$ is an unsubstituted $C_{23}$ alkyl. In embodiments, $R^1$ is an unsubstituted $C_{24}$ alkyl. In embodiments, $R^1$ is an unsubstituted $C_{25}$ alkyl. In embodiments, $R^1$ is an unsubstituted $C_{26}$ alkyl. In embodiments, $R^1$ is an unsubstituted $C_{27}$ alkyl. In embodiments, $R^1$ is an unsubstituted $C_{28}$ alkyl. In embodiments, $R^1$ is an unsubstituted $C_{29}$ alkyl. In embodiments, $R^1$ is an unsubstituted $C_{30}$ alkyl.

In embodiments, $R^1$ is substituted or unsubstituted alkenyl (e.g., $C_1$-$C_{30}$, $C_1$-$C_{24}$, $C_1$-$C_{18}$, or $C_1$-$C_{12}$). In embodiments, $R^1$ is substituted or unsubstituted alkenyl (e.g., $C_6$-$C_{30}$, $C_6$-$C_{24}$, $C_6$-$C_{18}$, or $C_6$-$C_{12}$). In embodiments, $R^1$ is substituted (e.g., substituted with a substituent group, a size-limited substituent group, or lower substituent group) or unsubstituted alkenyl. In embodiments, $R^1$ is unsubstituted alkenyl. In embodiments, $R^1$ is substituted (e.g., substituted with a substituent group, a size-limited substituent group, or lower substituent group) or unsubstituted alkenyl. In embodiments, $R^1$ is an alkenyl substituted with a substituent group. In embodiments, $R^1$ is an alkenyl substituted with a size-limited substituent group. In embodiments, $R^1$ is an alkenyl substituted with a lower substituent group. In embodiments, $R^1$ is unsubstituted alkenyl.

In embodiments, $R^1$ is substituted (e.g., substituted with a substituent group, a size-limited substituent group, or lower substituent group) or unsubstituted alkenyl. In embodiments, $R^1$ is substituted (e.g., substituted with a substituent group, a size-limited substituent group, or lower substituent group) alkenyl. In embodiments, $R^1$ is unsubstituted alkenyl. In embodiments, $R^1$ is substituted or unsubstituted alkenyl (e.g., $C_6$-$C_{30}$, $C_6$-$C_{24}$, $C_6$-$C_{18}$, or $C_6$-$C_{12}$). In embodiments, $R^1$ is substituted alkenyl (e.g., $C_6$-$C_{30}$, $C_6$-$C_{24}$, $C_6$-$C_{18}$, or $C_6$-$C_{12}$). In embodiments, $R^1$ is unsubstituted alkenyl (e.g., $C_6$-$C_{30}$, $C_6$-$C_{24}$, $C_6$-$C_{18}$, or $C_6$-$C_{12}$).

In embodiments, $R^1$ is substituted (e.g., substituted with a substituent group, a size-limited substituent group, or lower substituent group) or unsubstituted $C_6$-$C_{30}$ alkenyl. In embodiments, $R^1$ is substituted (e.g., substituted with a substituent group, a size-limited substituent group, or lower substituent group) or unsubstituted $C_6$-$C_{30}$ alkenyl. In embodiments, $R^1$ is substituted (e.g., substituted with a substituent group, a size-limited substituent group, or lower substituent group) or unsubstituted $C_6$-$C_{24}$ alkenyl. In embodiments, $R^1$ is substituted (e.g., substituted with a substituent group, a size-limited substituent group, or lower substituent group) or unsubstituted $C_6$-$C_{18}$ alkenyl. In embodiments, $R^1$ is substituted (e.g., substituted with a substituent group, a size-limited substituent group, or lower substituent group) or unsubstituted $C_6$-$C_{12}$ alkenyl. In embodiments, $R^1$ is substituted (e.g., substituted with a substituent group, a size-limited substituent group, or lower substituent group) $C_6$-$C_{30}$ alkenyl. In embodiments, $R^1$ is substituted (e.g., substituted with a substituent group, a size-limited substituent group, or lower substituent group)

$C_6$-$C_{30}$ alkenyl. In embodiments, $R^1$ is substituted (e.g., substituted with a substituent group, a size-limited substituent group, or lower substituent group) $C_6$-$C_{24}$ alkenyl. In embodiments, $R^1$ is substituted (e.g., substituted with a substituent group, a size-limited substituent group, or lower substituent group) $C_6$-$C_{18}$ alkenyl. In embodiments, $R^1$ is substituted (e.g., substituted with a substituent group, a size-limited substituent group, or lower substituent group) $C_6$-$C_{12}$ alkenyl. In embodiments, $R^1$ is an unsubstituted $C_6$-$C_{30}$ alkenyl. In embodiments, $R^1$ is an unsubstituted $C_6$-$C_{30}$ alkenyl. In embodiments, $R^1$ is an unsubstituted $C_6$-$C_{24}$ alkenyl. In embodiments, $R^1$ is an unsubstituted $C_6$-$C_{18}$ alkenyl. In embodiments, $R^1$ is an unsubstituted $C_6$-$C_{12}$ alkenyl.

In embodiments, $R^1$ is a substituted or unsubstituted $C_1$ alkenyl. In embodiments, $R^1$ is a substituted or unsubstituted $C_2$ alkenyl. In embodiments, $R^1$ is a substituted or unsubstituted $C_3$ alkenyl. In embodiments, $R^1$ is a substituted or unsubstituted $C_4$ alkenyl. In embodiments, $R^1$ is a substituted or unsubstituted $C_5$ alkenyl. In embodiments, $R^1$ is a substituted or unsubstituted $C_6$ alkenyl. In embodiments, $R^1$ is a substituted or unsubstituted $C_7$ alkenyl. In embodiments, $R^1$ is a substituted or unsubstituted $C_8$ alkenyl. In embodiments, $R^1$ is a substituted or unsubstituted $C_9$ alkenyl. In embodiments, $R^1$ is a substituted or unsubstituted $C_{10}$ alkenyl. In embodiments, $R^1$ is a substituted or unsubstituted $C_{11}$ alkenyl. In embodiments, $R^1$ is a substituted or unsubstituted $C_{12}$ alkenyl. In embodiments, $R^1$ is a substituted or unsubstituted $C_{13}$ alkenyl. In embodiments, $R^1$ is a substituted or unsubstituted $C_{14}$ alkenyl. In embodiments, $R^1$ is a substituted or unsubstituted $C_{15}$ alkenyl. In embodiments, $R^1$ is a substituted or unsubstituted $C_{16}$ alkenyl. In embodiments, $R^1$ is a substituted or unsubstituted $C_{17}$ alkenyl. In embodiments, $R^1$ is a substituted or unsubstituted $C_{18}$ alkenyl. In embodiments, $R^1$ is a substituted or unsubstituted $C_{19}$ alkenyl. In embodiments, $R^1$ is a substituted or unsubstituted $C_{20}$ alkenyl. In embodiments, $R^1$ is a substituted or unsubstituted $C_{21}$ alkenyl. In embodiments, $R^1$ is a substituted or unsubstituted $C_{22}$ alkenyl. In embodiments, $R^1$ is a substituted or unsubstituted $C_{23}$ alkenyl. In embodiments, $R^1$ is a substituted or unsubstituted $C_{24}$ alkenyl. In embodiments, $R^1$ is a substituted or unsubstituted $C_{25}$ alkenyl. In embodiments, $R^1$ is a substituted or unsubstituted $C_{26}$ alkenyl. In embodiments, $R^1$ is a substituted or unsubstituted $C_{27}$ alkenyl. In embodiments, $R^1$ is a substituted or unsubstituted $C_{28}$ alkenyl. In embodiments, $R^1$ is a substituted or unsubstituted $C_{29}$ alkenyl. In embodiments, $R^1$ is a substituted or unsubstituted $C_{30}$ alkenyl.

In embodiments, $R^1$ is a substituted $C_1$ alkenyl. In embodiments, $R^1$ is a substituted $C_2$ alkenyl. In embodiments, $R^1$ is a substituted $C_3$ alkenyl. In embodiments, $R^1$ is a substituted $C_4$ alkenyl. In embodiments, $R^1$ is a substituted $C_5$ alkenyl. In embodiments, $R^1$ is a substituted $C_6$ alkenyl. In embodiments, $R^1$ is a substituted $C_7$ alkenyl. In embodiments, $R^1$ is a substituted $C_8$ alkenyl. In embodiments, $R^1$ is a substituted $C_9$ alkenyl. In embodiments, $R^1$ is a substituted $C_{10}$ alkenyl. In embodiments, $R^1$ is a substituted $C_{11}$ alkenyl. In embodiments, $R^1$ is a substituted $C_{12}$ alkenyl. In embodiments, $R^1$ is a substituted $C_{13}$ alkenyl. In embodiments, $R^1$ is a substituted $C_{14}$ alkenyl. In embodiments, $R^1$ is a substituted $C_{15}$ alkenyl. In embodiments, $R^1$ is a substituted $C_{16}$ alkenyl. In embodiments, $R^1$ is a substituted $C_{17}$ alkenyl. In embodiments, $R^1$ is a substituted $C_{18}$ alkenyl. In embodiments, $R^1$ is a substituted $C_{19}$ alkenyl. In embodiments, $R^1$ is a substituted $C_{20}$ alkenyl. In embodiments, $R^1$ is a substituted $C_{21}$ alkenyl. In embodiments, $R^1$ is a substituted $C_{22}$ alkenyl. In embodiments, $R^1$ is a substituted $C_{23}$ alkenyl. In embodiments, $R^1$ is a substituted $C_{24}$ alkenyl. In embodiments, $R^1$ is a substituted $C_{25}$ alkenyl. In embodiments, $R^1$ is a substituted $C_{26}$ alkenyl. In embodiments, $R^1$ is a substituted $C_{27}$ alkenyl. In embodiments, $R^1$ is a substituted $C_{28}$ alkenyl. In embodiments, $R^1$ is a substituted $C_{29}$ alkenyl. In embodiments, $R^1$ is a substituted $C_{30}$ alkenyl. In embodiments, $R^1$ is an unsubstituted $C_1$ alkenyl. In embodiments, $R^1$ is an unsubstituted $C_2$ alkenyl. In embodiments, $R^1$ is an unsubstituted $C_3$ alkenyl. In embodiments, $R^1$ is an unsubstituted $C_4$ alkenyl. In embodiments, $R^1$ is an unsubstituted $C_5$ alkenyl. In embodiments, $R^1$ is an unsubstituted $C_6$ alkenyl. In embodiments, $R^1$ is an unsubstituted $C_7$ alkenyl. In embodiments, $R^1$ is an unsubstituted $C_8$ alkenyl. In embodiments, $R^1$ is an unsubstituted $C_9$ alkenyl. In embodiments, $R^1$ is an unsubstituted $C_{10}$ alkenyl. In embodiments, $R^1$ is an unsubstituted $C_{11}$ alkenyl. In embodiments, $R^1$ is an unsubstituted $C_{12}$ alkenyl. In embodiments, $R^1$ is an unsubstituted $C_{13}$ alkenyl. In embodiments, $R^1$ is an unsubstituted $C_{14}$ alkenyl. In embodiments, $R^1$ is an unsubstituted $C_{15}$ alkenyl. In embodiments, $R^1$ is an unsubstituted $C_{16}$ alkenyl. In embodiments, $R^1$ is an unsubstituted $C_{17}$ alkenyl. In embodiments, $R^1$ is an unsubstituted $C_{18}$ alkenyl. In embodiments, $R^1$ is an unsubstituted $C_{19}$ alkenyl. In embodiments, $R^1$ is an unsubstituted $C_{20}$ alkenyl. In embodiments, $R^1$ is an unsubstituted $C_{21}$ alkenyl. In embodiments, $R^1$ is an unsubstituted $C_{22}$ alkenyl. In embodiments, $R^1$ is an unsubstituted $C_{23}$ alkenyl. In embodiments, $R^1$ is an unsubstituted $C_{24}$ alkenyl. In embodiments, $R^1$ is an unsubstituted $C_{25}$ alkenyl. In embodiments, $R^1$ is an unsubstituted $C_{26}$ alkenyl. In embodiments, $R^1$ is an unsubstituted $C_{27}$ alkenyl. In embodiments, $R^1$ is an unsubstituted $C_{28}$ alkenyl. In embodiments, $R^1$ is an unsubstituted $C_{29}$ alkenyl. In embodiments, $R^1$ is an unsubstituted $C_{30}$ alkenyl.

In embodiments, $R^1$ is a substituted or unsubstituted $C_4$-$C_{30}$ alkyl. In embodiments, $R^1$ is an unsubstituted $C_4$-$C_{20}$ alkyl. In embodiments, $R^1$ is an unsubstituted $C_6$-$C_{18}$ alkyl. In embodiments, $R^1$ is an unsubstituted $C_{10}$-$C_{18}$ alkyl. In embodiments, $R^1$ is an unsubstituted $C_6$-$C_{18}$ alkenyl. In embodiments, $R^1$ is a substituted $C_1$ alkyl. In embodiments, $R^1$ is a substituted $C_{17}$ alkyl. In embodiments, $R^1$ is an unsubstituted $C_{11}$ alkyl. In embodiments, $R^1$ is an unsubstituted $C_{17}$ alkyl.

In embodiments, $R^1$ is substituted or unsubstituted alkyl (e.g., $C_1$-$C_{30}$, $C_1$-$C_{24}$, $C_1$-$C_{18}$, or $C_1$-$C_{12}$). In embodiments, $R^1$ is substituted or unsubstituted alkyl (e.g., $C_6$-$C_{30}$, $C_6$-$C_{24}$, $C_6$-$C_{18}$, or $C_6$-$C_{12}$). In embodiments, $R^1$ is substituted (e.g., substituted with a substituent group, a size-limited substituent group, or lower substituent group) or unsubstituted alkyl. In embodiments, $R^1$ is unsubstituted alkyl. In embodiments, $R^1$ is substituted (e.g., substituted with a substituent group, a size-limited substituent group, or lower substituent group) or unsubstituted alkyl. In embodiments, $R^1$ is an alkyl substituted with a substituent group. In embodiments, $R^1$ is an alkyl substituted with a size-limited substituent group. In embodiments, $R^1$ is an alkyl substituted with a lower substituent group. In embodiments, $R^1$ is unsubstituted alkyl.

In embodiments, $R^1$ is substituted (e.g., substituted with a substituent group, a size-limited substituent group, or lower substituent group) or unsubstituted alkyl. In embodiments, $R^1$ is substituted (e.g., substituted with a substituent group, a size-limited substituent group, or lower substituent group) alkyl. In embodiments, $R^1$ is unsubstituted alkyl. In embodiments, $R^1$ is substituted or unsubstituted alkyl (e.g., $C_6$-$C_{30}$, $C_6$-$C_{24}$, $C_6$-$C_{18}$, or $C_6$-$C_{12}$). In embodiments, $R^1$ is substituted alkyl (e.g., $C_6$-$C_{30}$, $C_6$-$C_{24}$, $C_6$-$C_{18}$, or $C_6$-$C_{12}$). In embodiments, $R^1$ is unsubstituted alkyl (e.g., $C_6$-$C_{30}$, $C_6$-$C_{24}$, $C_6$-$C_{18}$, or $C_6$-$C_{12}$).

In embodiments, $R^1$ is substituted (e.g., substituted with a substituent group, a size-limited substituent group, or lower substituent group) or unsubstituted $C_6$-$C_{30}$ alkyl. In embodiments, $R^1$ is substituted (e.g., substituted with a substituent group, a size-limited substituent group, or lower substituent group) or unsubstituted $C_6$-$C_{30}$ alkyl. In embodiments, $R^1$ is substituted (e.g., substituted with a substituent group, a size-limited substituent group, or lower substituent group) or unsubstituted $C_6$-$C_{24}$ alkyl. In embodiments, $R^1$ is substituted (e.g., substituted with a substituent group, a size-limited substituent group, or lower substituent group) or unsubstituted $C_6$-$C_{18}$ alkyl. In embodiments, $R^1$ is substituted (e.g., substituted with a substituent group, a size-limited substituent group, or lower substituent group) or unsubstituted $C_6$-$C_{12}$ alkyl. In embodiments, $R^1$ is substituted (e.g., substituted with a substituent group, a size-limited substituent group, or lower substituent group) $C_6$-$C_{30}$ alkyl. In embodiments, $R^1$ is substituted (e.g., substituted with a substituent group, a size-limited substituent group, or lower substituent group) $C_6$-$C_{30}$ alkyl. In embodiments, $R^1$ is substituted (e.g., substituted with a substituent group, a size-limited substituent group, or lower substituent group) $C_6$-$C_{24}$ alkyl. In embodiments, $R^1$ is substituted (e.g., substituted with a substituent group, a size-limited substituent group, or lower substituent group) $C_6$-$C_{18}$ alkyl. In embodiments, $R^1$ is substituted (e.g., substituted with a substituent group, a size-limited substituent group, or lower substituent group) $C_6$-$C_{12}$ alkyl. In embodiments, $R^1$ is an unsubstituted $C_6$-$C_{30}$ alkyl. In embodiments, $R^1$ is an unsubstituted $C_6$-$C_{30}$ alkyl. In embodiments, $R^1$ is an unsubstituted $C_6$-$C_{24}$ alkyl. In embodiments, $R^1$ is an unsubstituted $C_6$-$C_{18}$ alkyl. In embodiments, $R^1$ is an unsubstituted $C_6$-$C_{12}$ alkyl.

In embodiments, $R^1$ is a substituted or unsubstituted $C_1$ alkyl. In embodiments, $R^1$ is a substituted or unsubstituted $C_2$ alkyl. In embodiments, $R^1$ is a substituted or unsubstituted $C_3$ alkyl. In embodiments, $R^1$ is a substituted or unsubstituted $C_4$ alkyl. In embodiments, $R^1$ is a substituted or unsubstituted $C_5$ alkyl. In embodiments, $R^1$ is a substituted or unsubstituted $C_6$ alkyl. In embodiments, $R^1$ is a substituted or unsubstituted $C_7$ alkyl. In embodiments, $R^1$ is a substituted or unsubstituted $C_8$ alkyl. In embodiments, $R^1$ is a substituted or unsubstituted $C_9$ alkyl. In embodiments, $R^1$ is a substituted or unsubstituted $C_{10}$ alkyl. In embodiments, $R^1$ is a substituted or unsubstituted $C_{11}$ alkyl. In embodiments, $R^1$ is a substituted or unsubstituted $C_{12}$ alkyl. In embodiments, $R^1$ is a substituted or unsubstituted $C_{13}$ alkyl. In embodiments, $R^1$ is a substituted or unsubstituted $C_{14}$ alkyl. In embodiments, $R^1$ is a substituted or unsubstituted $C_{15}$ alkyl. In embodiments, $R^1$ is a substituted or unsubstituted $C_{16}$ alkyl. In embodiments, $R^1$ is a substituted or unsubstituted $C_{17}$ alkyl. In embodiments, $R^1$ is a substituted or unsubstituted $C_{18}$ alkyl. In embodiments, $R^1$ is a substituted or unsubstituted $C_{19}$ alkyl. In embodiments, $R^1$ is a substituted or unsubstituted $C_{20}$ alkyl. In embodiments, $R^1$ is a substituted or unsubstituted $C_{21}$ alkyl. In embodiments, $R^1$ is a substituted or unsubstituted $C_{22}$ alkyl. In embodiments, $R^1$ is a substituted or unsubstituted $C_{23}$ alkyl. In embodiments, $R^1$ is a substituted or unsubstituted $C_{24}$ alkyl. In embodiments, $R^1$ is a substituted or unsubstituted $C_{25}$ alkyl. In embodiments, $R^1$ is a substituted or unsubstituted $C_{26}$ alkyl. In embodiments, $R^1$ is a substituted or unsubstituted $C_{27}$ alkyl. In embodiments, $R^1$ is a substituted or unsubstituted $C_{28}$ alkyl. In embodiments, $R^1$ is a substituted or unsubstituted $C_{29}$ alkyl. In embodiments, $R^1$ is a substituted or unsubstituted $C_{30}$ alkyl.

In embodiments, $R^1$ is a substituted $C_1$ alkyl. In embodiments, $R^1$ is a substituted $C_2$ alkyl. In embodiments, $R^1$ is a substituted $C_3$ alkyl. In embodiments, $R^1$ is a substituted $C_4$ alkyl. In embodiments, $R^1$ is a substituted $C_5$ alkyl. In embodiments, $R^1$ is a substituted $C_6$ alkyl. In embodiments, $R^1$ is a substituted $C_7$ alkyl. In embodiments, $R^1$ is a substituted $C_8$ alkyl. In embodiments, $R^1$ is a substituted $C_9$ alkyl. In embodiments, $R^1$ is a substituted $C_{10}$ alkyl. In embodiments, $R^1$ is a substituted $C_{11}$ alkyl. In embodiments, $R^1$ is a substituted $C_{12}$ alkyl. In embodiments, $R^1$ is a substituted $C_{13}$ alkyl. In embodiments, $R^1$ is a substituted $C_{14}$ alkyl. In embodiments, $R^1$ is a substituted $C_{15}$ alkyl. In embodiments, $R^1$ is a substituted $C_{16}$ alkyl. In embodiments, $R^1$ is a substituted $C_{17}$ alkyl. In embodiments, $R^1$ is a substituted $C_{18}$ alkyl. In embodiments, $R^1$ is a substituted $C_{19}$ alkyl. In embodiments, $R^1$ is a substituted $C_{20}$ alkyl. In embodiments, $R^1$ is a substituted $C_{21}$ alkyl. In embodiments, $R^1$ is a substituted $C_{22}$ alkyl. In embodiments, $R^1$ is a substituted $C_{23}$ alkyl. In embodiments, $R^1$ is a substituted $C_{24}$ alkyl. In embodiments, $R^1$ is a substituted $C_{25}$ alkyl. In embodiments, $R^1$ is a substituted $C_{26}$ alkyl. In embodiments, $R^1$ is a substituted $C_{27}$ alkyl. In embodiments, $R^1$ is a substituted $C_{28}$ alkyl. In embodiments, $R^1$ is a substituted $C_{29}$ alkyl. In embodiments, $R^1$ is a substituted $C_{30}$ alkyl. In embodiments, $R^1$ is an unsubstituted $C_1$ alkyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl. In embodiments, $R^1$ is an unsubstituted $C_9$ alkyl. In embodiments, $R^1$ is an unsubstituted $C_{10}$ alkyl. In embodiments, $R^1$ is an unsubstituted $C_{11}$ alkyl. In embodiments, $R^1$ is an unsubstituted $C_{12}$ alkyl. In embodiments, $R^1$ is an unsubstituted $C_{13}$ alkyl. In embodiments, $R^1$ is an unsubstituted $C_{14}$ alkyl. In embodiments, $R^1$ is an unsubstituted $C_{15}$ alkyl. In embodiments, $R^1$ is an unsubstituted $C_{16}$ alkyl. In embodiments, $R^1$ is an unsubstituted $C_{17}$ alkyl. In embodiments, $R^1$ is an unsubstituted $C_{18}$ alkyl. In embodiments, $R^1$ is an unsubstituted $C_{19}$ alkyl. In embodiments, $R^1$ is an unsubstituted $C_{20}$ alkyl. In embodiments, $R^1$ is an unsubstituted $C_{21}$ alkyl. In embodiments, $R^1$ is an unsubstituted $C_{22}$ alkyl. In embodiments, $R^1$ is an unsubstituted $C_{23}$ alkyl. In embodiments, $R^1$ is an unsubstituted $C_{24}$ alkyl. In embodiments, $R^1$ is an unsubstituted $C_{25}$ alkyl. In embodiments, $R^1$ is an unsubstituted $C_{26}$ alkyl. In embodiments, $R^1$ is an unsubstituted $C_{27}$ alkyl. In embodiments, $R^1$ is an unsubstituted $C_{28}$ alkyl. In embodiments, $R^1$ is an unsubstituted $C_{29}$ alkyl. In embodiments, $R^1$ is an unsubstituted $C_{30}$ alkyl.

In embodiments, $R^1$ is substituted or unsubstituted alkenyl (e.g., $C_1$-$C_{30}$, $C_1$-$C_{24}$, $C_1$-$C_{18}$, or $C_1$-$C_{12}$). In embodiments, $R^1$ is substituted or unsubstituted alkenyl (e.g., $C_6$-$C_{30}$, $C_6$-$C_{24}$, $C_6$-$C_{18}$, or $C_6$-$C_{12}$). In embodiments, $R^1$ is substituted (e.g., substituted with a substituent group, a size-limited substituent group, or lower substituent group) or unsubstituted alkenyl. In embodiments, $R^1$ is unsubstituted alkenyl. In embodiments, $R^1$ is substituted (e.g., substituted with a substituent group, a size-limited substituent group, or lower substituent group) or unsubstituted alkenyl. In embodiments, $R^1$ is an alkenyl substituted with a substituent group. In embodiments, $R^1$ is an alkenyl substituted with a size-limited substituent group. In embodiments, $R^1$ is an alkenyl substituted with a lower substituent group. In embodiments, $R^1$ is unsubstituted alkenyl.

In embodiments, $R^1$ is substituted (e.g., substituted with a substituent group, a size-limited substituent group, or lower substituent group) or unsubstituted alkenyl. In embodiments, $R^1$ is substituted (e.g., substituted with a substituent group, a size-limited substituent group, or lower substituent group) alkenyl. In embodiments, $R^1$ is unsubstituted alkenyl. In embodiments, $R^1$ is substituted or unsubstituted alkenyl (e.g., $C_6$-$C_{30}$, $C_6$-$C_{24}$, $C_6$-$C_{18}$, or $C_6$-$C_{12}$). In embodiments, $R^1$ is substituted alkenyl (e.g., $C_6$-$C_{30}$, $C_6$-$C_{24}$, $C_6$-$C_{18}$, or $C_6$-$C_{12}$). In embodiments, $R^1$ is unsubstituted alkenyl (e.g., $C_6$-$C_{30}$, $C_6$-$C_{24}$, $C_6$-$C_{18}$, or $C_6$-$C_{12}$).

In embodiments, $R^1$ is substituted (e.g., substituted with a substituent group, a size-limited substituent group, or lower substituent group) or unsubstituted $C_6$-$C_{30}$ alkenyl. In embodiments, $R^1$ is substituted (e.g., substituted with a substituent group, a size-limited substituent group, or lower substituent group) or unsubstituted $C_6$-$C_{30}$ alkenyl. In embodiments, $R^1$ is substituted (e.g., substituted with a substituent group, a size-limited substituent group, or lower substituent group) or unsubstituted $C_6$-$C_{24}$ alkenyl. In embodiments, $R^1$ is substituted (e.g., substituted with a substituent group, a size-limited substituent group, or lower substituent group) or unsubstituted $C_6$-$C_{18}$ alkenyl. In embodiments, $R^1$ is substituted (e.g., substituted with a substituent group, a size-limited substituent group, or lower substituent group) or unsubstituted $C_6$-$C_{12}$ alkenyl. In embodiments, $R^1$ is substituted (e.g., substituted with a substituent group, a size-limited substituent group, or lower substituent group) $C_6$-$C_{30}$ alkenyl. In embodiments, $R^1$ is substituted (e.g., substituted with a substituent group, a size-limited substituent group, or lower substituent group) $C_6$-$C_{30}$ alkenyl. In embodiments, $R^1$ is substituted (e.g., substituted with a substituent group, a size-limited substituent group, or lower substituent group) $C_6$-$C_{24}$ alkenyl. In embodiments, $R^1$ is substituted (e.g., substituted with a substituent group, a size-limited substituent group, or lower substituent group) $C_6$-$C_{18}$ alkenyl. In embodiments, $R^1$ is substituted (e.g., substituted with a substituent group, a size-limited substituent group, or lower substituent group) $C_6$-$C_{12}$ alkenyl. In embodiments, $R^1$ is an unsubstituted $C_6$-$C_{30}$ alkenyl. In embodiments, $R^1$ is an unsubstituted $C_6$-$C_{30}$ alkenyl. In embodiments, $R^1$ is an unsubstituted $C_6$-$C_{24}$ alkenyl. In embodiments, $R^1$ is an unsubstituted $C_6$-$C_{18}$ alkenyl. In embodiments, $R^1$ is an unsubstituted $C_6$-$C_{12}$ alkenyl.

In embodiments, $R^1$ is a substituted or unsubstituted $C_1$ alkenyl. In embodiments, $R^1$ is a substituted or unsubstituted $C_2$ alkenyl. In embodiments, $R^1$ is a substituted or unsubstituted $C_3$ alkenyl. In embodiments, $R^1$ is a substituted or unsubstituted $C_4$ alkenyl. In embodiments, $R^1$ is a substituted or unsubstituted $C_5$ alkenyl. In embodiments, $R^1$ is a substituted or unsubstituted $C_6$ alkenyl. In embodiments, $R^1$ is a substituted or unsubstituted $C_7$ alkenyl. In embodiments, $R^1$ is a substituted or unsubstituted $C_8$ alkenyl. In embodiments, $R^1$ is a substituted or unsubstituted $C_9$ alkenyl. In embodiments, $R^1$ is a substituted or unsubstituted $C_{10}$ alkenyl. In embodiments, $R^1$ is a substituted or unsubstituted $C_{11}$ alkenyl. In embodiments, $R^1$ is a substituted or unsubstituted $C_{12}$ alkenyl. In embodiments, $R^1$ is a substituted or unsubstituted $C_{13}$ alkenyl. In embodiments, $R^1$ is a substituted or unsubstituted $C_{14}$ alkenyl. In embodiments, $R^1$ is a substituted or unsubstituted $C_{15}$ alkenyl. In embodiments, $R^1$ is a substituted or unsubstituted $C_{16}$ alkenyl. In embodiments, $R^1$ is a substituted or unsubstituted $C_{17}$ alkenyl. In embodiments, $R^1$ is a substituted or unsubstituted $C_{18}$ alkenyl. In embodiments, $R^1$ is a substituted or unsubstituted $C_{19}$ alkenyl. In embodiments, $R^1$ is a substituted or unsubstituted $C_{20}$ alkenyl. In embodiments, $R^1$ is a substituted or unsubstituted $C_{21}$ alkenyl. In embodiments, $R^1$ is a substituted or unsubstituted $C_{22}$ alkenyl. In embodiments, $R^1$ is a substituted or unsubstituted $C_{23}$ alkenyl. In embodiments, $R^1$ is a substituted or unsubstituted $C_{24}$ alkenyl. In embodiments, $R^1$ is a substituted or unsubstituted $C_{25}$ alkenyl. In embodiments, $R^1$ is a substituted or unsubstituted $C_{26}$ alkenyl. In embodiments, $R^1$ is a substituted or unsubstituted $C_{27}$ alkenyl. In embodiments, $R^1$ is a substituted or unsubstituted $C_{28}$ alkenyl. In embodiments, $R^1$ is a substituted or unsubstituted $C_{29}$ alkenyl. In embodiments, $R^1$ is a substituted or unsubstituted $C_{30}$ alkenyl.

In embodiments, $R^1$ is a substituted $C_1$ alkenyl. In embodiments, $R^1$ is a substituted $C_2$ alkenyl. In embodiments, $R^1$ is a substituted $C_3$ alkenyl. In embodiments, $R^1$ is a substituted $C_4$ alkenyl. In embodiments, $R^1$ is a substituted $C_5$ alkenyl. In embodiments, $R^1$ is a substituted $C_6$ alkenyl. In embodiments, $R^1$ is a substituted $C_7$ alkenyl. In embodiments, $R^1$ is a substituted $C_8$ alkenyl. In embodiments, $R^1$ is a substituted $C_9$ alkenyl. In embodiments, $R^1$ is a substituted $C_{10}$ alkenyl. In embodiments, $R^1$ is a substituted $C_{11}$ alkenyl. In embodiments, $R^1$ is a substituted $C_{12}$ alkenyl. In embodiments, $R^1$ is a substituted $C_{13}$ alkenyl. In embodiments, $R^1$ is a substituted $C_{14}$ alkenyl. In embodiments, $R^1$ is a substituted $C_{15}$ alkenyl. In embodiments, $R^1$ is a substituted $C_{16}$ alkenyl. In embodiments, $R^1$ is a substituted $C_{17}$ alkenyl. In embodiments, $R^1$ is a substituted $C_{18}$ alkenyl. In embodiments, $R^1$ is a substituted $C_{19}$ alkenyl. In embodiments, $R^1$ is a substituted $C_{20}$ alkenyl. In embodiments, $R^1$ is a substituted $C_{21}$ alkenyl. In embodiments, $R^1$ is a substituted $C_{22}$ alkenyl. In embodiments, $R^1$ is a substituted $C_{23}$ alkenyl. In embodiments, $R^1$ is a substituted $C_{24}$ alkenyl. In embodiments, $R^1$ is a substituted $C_{25}$ alkenyl. In embodiments, $R^1$ is a substituted $C_{26}$ alkenyl. In embodiments, $R^1$ is a substituted $C_{27}$ alkenyl. In embodiments, $R^1$ is a substituted $C_{28}$ alkenyl. In embodiments, $R^1$ is a substituted $C_{29}$ alkenyl. In embodiments, $R^1$ is a substituted $C_{30}$ alkenyl. In embodiments, $R^1$ is an unsubstituted $C_1$ alkenyl. In embodiments, $R^1$ is an unsubstituted $C_2$ alkenyl. In embodiments, $R^1$ is an unsubstituted $C_3$ alkenyl. In embodiments, $R^1$ is an unsubstituted $C_4$ alkenyl. In embodiments, $R^1$ is an unsubstituted $C_5$ alkenyl. In embodiments, $R^1$ is an unsubstituted $C_6$ alkenyl. In embodiments, $R^1$ is an unsubstituted $C_7$ alkenyl. In embodiments, $R^1$ is an unsubstituted $C_8$ alkenyl. In embodiments, $R^1$ is an unsubstituted $C_9$ alkenyl. In embodiments, $R^1$ is an unsubstituted $C_{10}$ alkenyl. In embodiments, $R^1$ is an unsubstituted $C_{11}$ alkenyl. In embodiments, $R^1$ is an unsubstituted $C_{12}$ alkenyl. In embodiments, $R^1$ is an unsubstituted $C_{13}$ alkenyl. In embodiments, $R^1$ is an unsubstituted $C_{14}$ alkenyl. In embodiments, $R^1$ is an unsubstituted $C_{15}$ alkenyl. In embodiments, $R^1$ is an unsubstituted $C_{16}$ alkenyl. In embodiments, $R^1$ is an unsubstituted $C_{17}$ alkenyl. In embodiments, $R^1$ is an unsubstituted $C_{18}$ alkenyl. In embodiments, $R^1$ is an unsubstituted $C_{19}$ alkenyl. In embodiments, $R^1$ is an unsubstituted $C_{20}$ alkenyl. In embodiments, $R^1$ is an unsubstituted $C_{21}$ alkenyl. In embodiments, $R^1$ is an unsubstituted $C_{22}$ alkenyl. In embodiments, $R^1$ is an unsubstituted $C_{23}$ alkenyl. In embodiments, $R^1$ is an unsubstituted $C_{24}$ alkenyl. In embodiments, $R^1$ is an unsubstituted $C_{25}$ alkenyl. In embodiments, $R^1$ is an unsubstituted $C_{26}$ alkenyl. In embodiments, $R^1$ is an unsubstituted $C_{27}$ alkenyl. In embodiments, $R^1$ is an unsubstituted $C_{28}$ alkenyl. In embodiments, $R^1$ is an unsubstituted $C_{29}$ alkenyl. In embodiments, $R^1$ is an unsubstituted $C_{30}$ alkenyl.

In embodiments, $R^2$ is a substituted or unsubstituted $C_4$-$C_{30}$ alkyl. In embodiments, $R^2$ is a substituted or unsubstituted $C_4$-$C_{20}$ alkyl. In embodiments, $R^2$ is a substituted or unsubstituted $C_6$-$C_{18}$ alkyl. In embodiments, $R^2$ is a substituted or unsubstituted $C_{10}$-$C_{20}$ alkyl. In embodiments, $R^2$ is a substituted or unsubstituted $C_{10}$-$C_{18}$ alkyl. In embodiments, $R^2$ is a substituted or unsubstituted $C_{12}$-$C_{16}$ alkyl. In embodiments, $R^2$ is a substituted or unsubstituted $C_6$-$C_{18}$ alkyl. In embodiments, $R^2$ is a substituted or unsubstituted $C_{10}$-$C_{14}$ alkyl. In embodiments, $R^2$ is a substituted or unsubstituted $C_{16}$-$C_{20}$ alkyl. In embodiments, $R^2$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^2$ is a substituted $C_4$-$C_{30}$ alkyl. In embodiments, $R^2$ is a substituted $C_4$-$C_{20}$ alkyl. In embodiments, $R^2$ is a substituted $C_6$-$C_{18}$ alkyl. In embodiments, $R^2$ is a substituted $C_{10}$-$C_{20}$ alkyl. In embodiments, $R^2$ is a substituted $C_{10}$-$C_{18}$ alkyl. In embodiments, $R^2$ is a substituted $C_{12}$-$C_{16}$ alkyl. In embodiments, $R^2$ is a substituted $C_6$-$C_{18}$ alkyl. In embodiments, $R^2$ is a substituted $C_{10}$-$C_{14}$ alkyl. In embodiments, $R^2$ is a substituted $C_{16}$-$C_{20}$ alkyl. In embodiments, $R^2$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^2$ is an unsubstituted $C_4$-$C_{30}$ alkyl. In embodiments, $R^2$ is an unsubstituted $C_4$-$C_{20}$ alkyl. In embodiments, $R^2$ is an unsubstituted $C_6$-$C_{18}$ alkyl. In embodiments, $R^2$ is an unsubstituted $C_{10}$-$C_{20}$ alkyl. In embodiments, $R^2$ is an unsubstituted $C_{10}$-$C_{18}$ alkyl. In embodiments, $R^2$ is an unsubstituted $C_{12}$-$C_{16}$ alkyl. In embodiments, $R^2$ is an unsubstituted $C_6$-$C_{18}$ alkyl. In embodiments, $R^2$ is an unsubstituted $C_{10}$-$C_{14}$ alkyl. In embodiments, $R^2$ is an unsubstituted $C_{16}$-$C_{20}$ alkyl. In embodiments, $R^2$ is a $C_6$ alkyl; a $C_8$ alkyl; a $C_{10}$ alkyl; a $C_{12}$ alkyl; a $C_{14}$ alkyl; a $C_{16}$ alkyl; a $C_{18}$ alkyl; or a $C_{20}$ alkyl.

In embodiments, $R^2$ is a substituted or unsubstituted $C_4$-$C_{30}$ alkenyl. In embodiments, $R^2$ is a substituted or unsubstituted $C_4$-$C_{20}$ alkenyl. In embodiments, $R^2$ is a substituted or unsubstituted $C_6$-$C_{18}$ alkenyl. In embodiments, $R^2$ is a substituted or unsubstituted $C_{10}$-$C_{20}$ alkenyl. In embodiments, $R^2$ is a substituted or unsubstituted $C_{10}$-$C_{18}$ alkenyl. In embodiments, $R^2$ is a substituted or unsubstituted $C_{12}$-$C_{16}$ alkenyl. In embodiments, $R^2$ is a substituted or unsubstituted $C_6$-$C_{18}$ alkenyl. In embodiments, $R^2$ is a substituted or unsubstituted $C_{10}$-$C_{14}$ alkenyl. In embodiments, $R^2$ is a substituted or unsubstituted $Cl_6$—$C_{20}$ alkenyl. In embodiments, $R^2$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^2$ is a substituted $C_4$-$C_{30}$ alkenyl. In embodiments, $R^2$ is a substituted $C_4$-$C_{20}$ alkenyl. In embodiments, $R^2$ is a substituted $C_6$-$C_{18}$ alkenyl. In embodiments, $R^2$ is a substituted $C_{10}$-$C_{20}$ alkenyl. In embodiments, $R^2$ is a substituted $C_{10}$-$C_{18}$ alkenyl. In embodiments, $R^2$ is a substituted $C_{12}$-$C_{16}$ alkenyl. In embodiments, $R^2$ is a substituted $C_6$-$C_{18}$ alkenyl. In embodiments, $R^2$ is a substituted $C_{10}$-$C_{14}$ alkenyl. In embodiments, $R^2$ is a substituted $C_{16}$-$C_{20}$ alkenyl. In embodiments, $R^2$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^2$ is an unsubstituted $C_4$-$C_{30}$ alkenyl. In embodiments, $R^2$ is an unsubstituted $C_4$-$C_{20}$ alkenyl. In embodiments, $R^2$ is an unsubstituted $C_6$-$C_{18}$ alkenyl. In embodiments, $R^2$ is an unsubstituted $C_{10}$-$C_{20}$ alkenyl. In embodiments, $R^2$ is an unsubstituted $C_{10}$-$C_{18}$ alkenyl. In embodiments, $R^2$ is an unsubstituted $C_{12}$-$C_{16}$ alkenyl. In embodiments, $R^2$ is an unsubstituted $C_6$-$C_{18}$ alkenyl. In embodiments, $R^2$ is an unsubstituted $C_{10}$-$C_{14}$ alkenyl. In embodiments, $R^2$ is an unsubstituted $C_{16}$-$C_{20}$ alkenyl. In embodiments, $R^2$ is a $C_6$ alkenyl; a $C_8$ alkenyl; a $C_{10}$ alkenyl; a $C_{12}$ alkenyl; a $C_{14}$ alkenyl; a $C_{16}$ alkenyl; a $C_{18}$ alkenyl; or a $C_{20}$ alkenyl.

In embodiments, $R^2$ is substituted (e.g., substituted with a substituent group, a size-limited substituent group, or lower substituent group) or unsubstituted alkyl. In embodiments, $R^2$ is unsubstituted alkyl. In embodiments, $R^2$ is an alkyl substituted with a substituent group. In embodiments, $R^2$ is an alkyl substituted with a size-limited substituent group. In embodiments, $R^2$ is an alkyl substituted with a lower substituent group. In embodiments, $R^2$ is unsubstituted alkyl.

In embodiments, $R^2$ is substituted (e.g., substituted with a substituent group, a size-limited substituent group, or lower substituent group) or unsubstituted alkyl. In embodiments, $R^2$ is substituted (e.g., substituted with a substituent group, a size-limited substituent group, or lower substituent group) alkyl. In embodiments, $R^2$ is unsubstituted alkyl. In embodiments, $R^2$ is substituted or unsubstituted alkyl (e.g., $C_6$-$C_{30}$, $C_6$-$C_{24}$, $C_6$-$C_{18}$, or $C_6$-$C_{12}$). In embodiments, $R^2$ is substituted alkyl (e.g., $C_6$-$C_{30}$, $C_6$-$C_{24}$, $C_6$-$C_{18}$, or $C_6$-$C_{12}$). In embodiments, $R^2$ is unsubstituted alkyl (e.g., $C_6$-$C_{30}$, $C_6$-$C_{24}$, $C_6$-$C_{18}$, or $C_6$-$C_{12}$).

In embodiments, $R^2$ is substituted (e.g., substituted with a substituent group, a size-limited substituent group, or lower substituent group) or unsubstituted $C_6$-$C_{30}$ alkyl. In embodiments, $R^2$ is substituted (e.g., substituted with a substituent group, a size-limited substituent group, or lower substituent group) or unsubstituted $C_6$-$C_{30}$ alkyl. In embodiments, $R^2$ is substituted (e.g., substituted with a substituent group, a size-limited substituent group, or lower substituent group) or unsubstituted $C_6$-$C_{24}$ alkyl. In embodiments, $R^2$ is substituted (e.g., substituted with a substituent group, a size-limited substituent group, or lower substituent group) or unsubstituted $C_6$-$C_{18}$ alkyl. In embodiments, $R^2$ is substituted (e.g., substituted with a substituent group, a size-limited substituent group, or lower substituent group) or unsubstituted $C_6$-$C_{12}$ alkyl. In embodiments, $R^2$ is substituted (e.g., substituted with a substituent group, a size-limited substituent group, or lower substituent group) $C_6$-$C_{30}$ alkyl. In embodiments, $R^2$ is substituted (e.g., substituted with a substituent group, a size-limited substituent group, or lower substituent group) $C_6$-$C_{30}$ alkyl. In embodiments, $R^2$ is substituted (e.g., substituted with a substituent group, a size-limited substituent group, or lower substituent group) $C_6$-$C_{24}$ alkyl. In embodiments, $R^2$ is substituted (e.g., substituted with a substituent group, a size-limited substituent group, or lower substituent group) $C_6$-$C_{18}$ alkyl. In embodiments, $R^2$ is substituted (e.g., substituted with a substituent group, a size-limited substituent group, or lower substituent group) $C_6$-$C_{12}$ alkyl. In embodiments, $R^2$ is an unsubstituted $C_6$-$C_{30}$ alkyl. In embodiments, $R^2$ is an unsubstituted $C_6$-$C_{30}$ alkyl. In embodiments, $R^2$ is an unsubstituted $C_6$-$C_{24}$ alkyl. In embodiments, $R^2$ is an unsubstituted $C_6$-$C_{18}$ alkyl. In embodiments, $R^2$ is an unsubstituted $C_6$-$C_{12}$ alkyl.

In embodiments, $R^2$ is a substituted or unsubstituted $C_1$ alkyl. In embodiments, $R^2$ is a substituted or unsubstituted $C_2$ alkyl. In embodiments, $R^2$ is a substituted or unsubstituted $C_3$ alkyl. In embodiments, $R^2$ is a substituted or unsubstituted $C_4$ alkyl. In embodiments, $R^2$ is a substituted or unsubstituted $C_5$ alkyl. In embodiments, $R^2$ is a substituted or unsubstituted $C_6$ alkyl. In embodiments, $R^2$ is a substituted or unsubstituted $C_7$ alkyl. In embodiments, $R^2$ is a substituted or unsubstituted $C_8$ alkyl. In embodiments, $R^2$ is a substituted or unsubstituted $C_9$ alkyl. In embodiments, $R^2$ is a substituted or unsubstituted $C_{10}$ alkyl. In embodiments, $R^2$ is a substituted or unsubstituted $C_{11}$ alkyl. In embodiments, $R^2$ is a substituted or unsubstituted $C_{12}$ alkyl. In embodiments, $R^2$ is a substituted or unsubstituted $C_{13}$ alkyl. In embodiments, $R^2$ is a substituted or unsubstituted $C_{14}$ alkyl. In embodiments, $R^2$ is a substituted or unsubstituted $C_{15}$ alkyl. In embodiments, $R^2$ is a substituted or unsubstituted $C_{16}$ alkyl. In embodiments, $R^2$ is a substituted or unsubstituted $C_{17}$ alkyl. In embodiments, $R^2$ is a substituted or unsubstituted $C_{18}$ alkyl. In embodiments, $R^2$ is a substituted or unsubstituted $C_{19}$ alkyl. In embodiments, $R^2$ is a substituted or unsubstituted $C_{20}$ alkyl. In embodiments, $R^2$ is a substituted or unsubstituted $C_{21}$ alkyl. In embodiments, $R^2$ is a substituted or unsubstituted $C_{22}$ alkyl. In embodiments, $R^2$ is a substituted or unsubstituted $C_{23}$ alkyl. In embodiments, $R^2$ is a substituted or unsubstituted $C_{24}$ alkyl. In embodiments, $R^2$ is a substituted or unsubstituted $C_{25}$ alkyl. In embodiments, $R^2$ is a substituted or unsubstituted $C_{26}$ alkyl. In embodiments, $R^2$ is a substituted or unsubstituted $C_{27}$ alkyl. In embodiments, $R^2$ is a substituted or unsubstituted $C_{28}$ alkyl. In embodiments, $R^2$ is a substituted or unsubstituted $C_{29}$ alkyl. In embodiments, $R^2$ is a substituted or unsubstituted $C_{30}$ alkyl.

In embodiments, $R^2$ is a substituted $C_1$ alkyl. In embodiments, $R^2$ is a substituted $C_2$ alkyl. In embodiments, $R^2$ is a substituted $C_3$ alkyl. In embodiments, $R^2$ is a substituted $C_4$ alkyl. In embodiments, $R^2$ is a substituted $C_5$ alkyl. In embodiments, $R^2$ is a substituted $C_6$ alkyl. In embodiments, $R^2$ is a substituted $C_7$ alkyl. In embodiments, $R^2$ is a substituted $C_8$ alkyl. In embodiments, $R^2$ is a substituted $C_9$ alkyl. In embodiments, $R^2$ is a substituted $C_{10}$ alkyl. In embodiments, $R^2$ is a substituted $C_{11}$ alkyl. In embodiments, $R^2$ is a substituted $C_{12}$ alkyl. In embodiments, $R^2$ is a substituted $C_{13}$ alkyl. In embodiments, $R^2$ is a substituted $C_{14}$ alkyl. In embodiments, $R^2$ is a substituted $C_{15}$ alkyl. In embodiments, $R^2$ is a substituted $C_{16}$ alkyl. In embodiments, $R^2$ is a substituted $C_{17}$ alkyl. In embodiments, $R^2$ is a substituted Cis alkyl. In embodiments, $R^2$ is a substituted $C_{19}$ alkyl. In embodiments, $R^2$ is a substituted $C_{20}$ alkyl. In embodiments, $R^2$ is a substituted $C_{21}$ alkyl. In embodiments, $R^2$ is a substituted $C_{22}$ alkyl. In embodiments, $R^2$ is a substituted $C_{23}$ alkyl. In embodiments, $R^2$ is a substituted $C_{24}$ alkyl. In embodiments, $R^2$ is a substituted $C_{25}$ alkyl. In embodiments, $R^2$ is a substituted $C_{26}$ alkyl. In embodiments, $R^2$ is a substituted $C_{27}$ alkyl. In embodiments, $R^2$ is a substituted $C_{28}$ alkyl. In embodiments, $R^2$ is a substituted $C_{29}$ alkyl. In embodiments, $R^2$ is a substituted $C_{30}$ alkyl. In embodiments, $R^2$ is an unsubstituted $C_1$ alkyl. In embodiments, $R^2$ is an unsubstituted $C_2$ alkyl. In embodiments, $R^2$ is an unsubstituted $C_3$ alkyl. In embodiments, $R^2$ is an unsubstituted $C_4$ alkyl. In embodiments, $R^2$ is an unsubstituted $C_5$ alkyl. In embodiments, $R^2$ is an unsubstituted $C_6$ alkyl. In embodiments, $R^2$ is an unsubstituted $C_7$ alkyl. In embodiments, $R^2$ is an unsubstituted $C_8$ alkyl. In embodiments, $R^2$ is an unsubstituted $C_9$ alkyl. In embodiments, $R^2$ is an unsubstituted $C_{10}$ alkyl. In embodiments, $R^2$ is an unsubstituted $C_{11}$ alkyl. In embodiments, $R^2$ is an unsubstituted $C_{12}$ alkyl. In embodiments, $R^2$ is an unsubstituted $C_{13}$ alkyl. In embodiments, $R^2$ is an unsubstituted $C_{14}$ alkyl. In embodiments, $R^2$ is an unsubstituted $C_{15}$ alkyl. In embodiments, $R^2$ is an unsubstituted $C_{16}$ alkyl. In embodiments, $R^2$ is an unsubstituted $C_{17}$ alkyl. In embodiments, $R^2$ is an unsubstituted $C_{18}$ alkyl. In embodiments, $R^2$ is an unsubstituted $C_{19}$ alkyl. In embodiments, $R^2$ is an unsubstituted $C_{20}$ alkyl. In embodiments, $R^2$ is an unsubstituted $C_{21}$ alkyl. In embodiments, $R^2$ is an unsubstituted $C_{22}$ alkyl. In embodiments, $R^2$ is an unsubstituted $C_{23}$ alkyl. In embodiments, $R^2$ is an unsubstituted $C_{24}$ alkyl. In embodiments, $R^2$ is an unsubstituted $C_{25}$ alkyl. In embodiments, $R^2$ is an unsubstituted $C_{26}$ alkyl. In embodiments, $R^2$ is an unsubstituted $C_{27}$ alkyl. In embodiments, $R^2$ is an unsubstituted $C_{28}$ alkyl. In embodiments, $R^2$ is an unsubstituted $C_{29}$ alkyl. In embodiments, $R^2$ is an unsubstituted $C_{30}$ alkyl.

In embodiments, $R^2$ is substituted or unsubstituted alkenyl (e.g., $C_1$-$C_{30}$, $C_1$-$C_{24}$, $C_1$-$C_{18}$, or $C_1$-$C_{12}$). In embodiments, $R^2$ is substituted or unsubstituted alkenyl (e.g., $C_6$-$C_{30}$, $C_6$-$C_{24}$, $C_6$-$C_{18}$, or $C_6$-$C_{12}$). In embodiments, $R^2$ is substituted (e.g., substituted with a substituent group, a size-limited substituent group, or lower substituent group) or unsubstituted alkenyl. In embodiments, $R^2$ is unsubstituted alkenyl. In embodiments, $R^2$ is substituted (e.g., substituted with a substituent group, a size-limited substituent group, or lower substituent group) or unsubstituted alkenyl. In embodiments, $R^2$ is an alkenyl substituted with a substituent group. In embodiments, $R^2$ is an alkenyl substituted with a size-limited substituent group. In embodiments, $R^2$ is an alkenyl substituted with a lower substituent group. In embodiments, $R^2$ is unsubstituted alkenyl.

In embodiments, $R^2$ is substituted (e.g., substituted with a substituent group, a size-limited substituent group, or lower substituent group) or unsubstituted alkenyl. In embodiments, $R^2$ is substituted (e.g., substituted with a substituent group, a size-limited substituent group, or lower substituent group) alkenyl. In embodiments, $R^2$ is unsubstituted alkenyl. In embodiments, $R^2$ is substituted or unsubstituted alkenyl (e.g., $C_6$-$C_{30}$, $C_6$-$C_{24}$, $C_6$-$C_{18}$, or $C_6$-$C_{12}$). In embodiments, $R^2$ is substituted alkenyl (e.g., $C_6$-$C_{30}$, $C_6$-$C_{24}$, $C_6$-$C_{18}$, or $C_6$-$C_{12}$). In embodiments, $R^2$ is unsubstituted alkenyl (e.g., $C_6$-$C_{30}$, $C_6$-$C_{24}$, $C_6$-$C_{18}$, or $C_6$-$C_{12}$).

In embodiments, $R^2$ is substituted (e.g., substituted with a substituent group, a size-limited substituent group, or lower substituent group) or unsubstituted $C_6$-$C_{30}$ alkenyl. In embodiments, $R^2$ is substituted (e.g., substituted with a substituent group, a size-limited substituent group, or lower substituent group) or unsubstituted $C_6$-$C_{30}$ alkenyl. In embodiments, $R^2$ is substituted (e.g., substituted with a substituent group, a size-limited substituent group, or lower substituent group) or unsubstituted $C_6$-$C_{24}$ alkenyl. In embodiments, $R^2$ is substituted (e.g., substituted with a substituent group, a size-limited substituent group, or lower substituent group) or unsubstituted $C_6$-$C_{18}$ alkenyl. In embodiments, $R^2$ is substituted (e.g., substituted with a substituent group, a size-limited substituent group, or lower substituent group) or unsubstituted $C_6$-$C_{12}$ alkenyl. In embodiments, $R^2$ is substituted (e.g., substituted with a substituent group, a size-limited substituent group, or lower substituent group) $C_6$-$C_{30}$ alkenyl. In embodiments, $R^2$ is substituted (e.g., substituted with a substituent group, a size-limited substituent group, or lower substituent group) $C_6$-$C_{30}$ alkenyl. In embodiments, $R^2$ is substituted (e.g., substituted with a substituent group, a size-limited substituent group, or lower substituent group) $C_6$-$C_{24}$ alkenyl. In embodiments, $R^2$ is substituted (e.g., substituted with a substituent group, a size-limited substituent group, or lower substituent group) $C_6$-$C_{18}$ alkenyl. In embodiments, $R^2$ is substituted (e.g., substituted with a substituent group, a size-limited substituent group, or lower substituent group) $C_6$-$C_{12}$ alkenyl. In embodiments, $R^2$ is an unsubstituted $C_6$-$C_{30}$ alkenyl. In embodiments, $R^2$ is an unsubstituted $C_6$-$C_{30}$ alkenyl. In embodiments, $R^2$ is an unsubstituted $C_6$-$C_{24}$ alkenyl. In embodiments, $R^2$ is an unsubstituted $C_6$-$C_{18}$ alkenyl. In embodiments, $R^2$ is an unsubstituted $C_6$-$C_{12}$ alkenyl.

In embodiments, $R^2$ is a substituted or unsubstituted $C_1$ alkenyl. In embodiments, $R^2$ is a substituted or unsubstituted $C_2$ alkenyl. In embodiments, $R^2$ is a substituted or unsubstituted $C_3$ alkenyl. In embodiments, $R^2$ is a substituted or unsubstituted $C_4$ alkenyl. In embodiments, $R^2$ is a substituted or unsubstituted $C_5$ alkenyl. In embodiments, $R^2$ is a substituted or unsubstituted $C_6$ alkenyl. In embodiments, $R^2$ is a substituted or unsubstituted $C_7$ alkenyl. In embodiments, $R^2$ is a substituted or unsubstituted $C_8$ alkenyl. In embodiments, $R^2$ is a substituted or unsubstituted $C_9$ alkenyl. In embodiments, $R^2$ is a substituted or unsubstituted $C_{10}$ alkenyl. In embodiments, $R^2$ is a substituted or unsubstituted $C_{11}$ alkenyl. In embodiments, $R^2$ is a substituted or unsubstituted $C_{12}$ alkenyl. In embodiments, $R^2$ is a substituted or unsubstituted $C_{13}$ alkenyl. In embodiments, $R^2$ is a substituted or unsubstituted $C_{14}$ alkenyl. In embodiments, $R^2$ is a substituted or unsubstituted $C_{15}$ alkenyl. In embodiments, $R^2$ is a substituted or unsubstituted $C_{16}$ alkenyl. In embodiments, $R^2$ is a substituted or unsubstituted $C_{17}$ alkenyl. In embodiments, $R^2$ is a substituted or unsubstituted $C_{18}$ alkenyl. In embodiments, $R^2$ is a substituted or unsubstituted $C_{19}$ alkenyl. In embodiments, $R^2$ is a substituted or unsubstituted $C_{20}$ alkenyl. In embodiments, $R^2$ is a substituted or unsubstituted $C_{21}$ alkenyl. In embodiments, $R^2$ is a substituted or unsubstituted $C_{22}$ alkenyl. In embodiments, $R^2$ is a substituted or unsubstituted $C_{23}$ alkenyl. In embodiments, $R^2$ is a substituted or unsubstituted $C_{24}$ alkenyl. In embodiments, $R^2$ is a substituted or unsubstituted $C_{25}$ alkenyl. In embodiments, $R^2$ is a substituted or unsubstituted $C_{26}$ alkenyl. In embodiments, $R^2$ is a substituted or unsubstituted $C_{27}$ alkenyl. In embodiments, $R^2$ is a substituted or unsubstituted $C_{28}$ alkenyl. In embodiments, $R^2$ is a substituted or unsubstituted $C_{29}$ alkenyl. In embodiments, $R^2$ is a substituted or unsubstituted $C_{30}$ alkenyl.

In embodiments, $R^2$ is a substituted $C_1$ alkenyl. In embodiments, $R^2$ is a substituted $C_2$ alkenyl. In embodiments, $R^2$ is a substituted $C_3$ alkenyl. In embodiments, $R^2$ is a substituted $C_4$ alkenyl. In embodiments, $R^2$ is a substituted $C_5$ alkenyl. In embodiments, $R^2$ is a substituted $C_6$ alkenyl. In embodiments, $R^2$ is a substituted $C_7$ alkenyl. In embodiments, $R^2$ is a substituted $C_8$ alkenyl. In embodiments, $R^2$ is a substituted $C_9$ alkenyl. In embodiments, $R^2$ is a substituted $C_{10}$ alkenyl. In embodiments, $R^2$ is a substituted $C_{11}$ alkenyl. In embodiments, $R^2$ is a substituted $C_{12}$ alkenyl. In embodiments, $R^2$ is a substituted $C_{13}$ alkenyl. In embodiments, $R^2$ is a substituted $C_{14}$ alkenyl. In embodiments, $R^2$ is a substituted $C_{15}$ alkenyl. In embodiments, $R^2$ is a substituted $C_{16}$ alkenyl. In embodiments, $R^2$ is a substituted $C_{17}$ alkenyl. In embodiments, $R^2$ is a substituted $C_{18}$ alkenyl. In embodiments, $R^2$ is a substituted $C_{19}$ alkenyl. In embodiments, $R^2$ is a substituted $C_{20}$ alkenyl. In embodiments, $R^2$ is a substituted $C_{21}$ alkenyl. In embodiments, $R^2$ is a substituted $C_{22}$ alkenyl. In embodiments, $R^2$ is a substituted $C_{23}$ alkenyl. In embodiments, $R^2$ is a substituted $C_{24}$ alkenyl. In embodiments, $R^2$ is a substituted $C_{25}$ alkenyl. In embodiments, $R^2$ is a substituted $C_{26}$ alkenyl. In embodiments, $R^2$ is a substituted $C_{27}$ alkenyl. In embodiments, $R^2$ is a substituted $C_{28}$ alkenyl. In embodiments, $R^2$ is a substituted $C_{29}$ alkenyl. In embodiments, $R^2$ is a substituted $C_{30}$ alkenyl. In embodiments, $R^2$ is an unsubstituted $C_1$ alkenyl. In embodiments, $R^2$ is an unsubstituted $C_2$ alkenyl. In embodiments, $R^2$ is an unsubstituted $C_3$ alkenyl. In embodiments, $R^2$ is an unsubstituted $C_4$ alkenyl. In embodiments, $R^2$ is an unsubstituted $C_5$ alkenyl. In embodiments, $R^2$ is an unsubstituted $C_6$ alkenyl. In embodiments, $R^2$ is an unsubstituted $C_7$ alkenyl. In embodiments, $R^2$ is an unsubstituted $C_8$ alkenyl. In embodiments, $R^2$ is an unsubstituted $C_9$ alkenyl. In embodiments, $R^2$ is an unsubstituted $C_{10}$ alkenyl. In embodiments, $R^2$ is an unsubstituted $C_{11}$ alkenyl. In embodiments, $R^2$ is an unsubstituted $C_{12}$ alkenyl. In embodiments, $R^2$ is an unsubstituted $C_{13}$ alkenyl. In embodiments, $R^2$ is an unsubstituted $C_{14}$ alkenyl. In embodiments, $R^2$ is an unsubstituted $C_{15}$ alkenyl. In embodiments, $R^2$ is an unsubstituted $C_{16}$ alkenyl. In embodiments, $R^2$ is an unsubstituted $C_{17}$ alkenyl. In embodiments, $R^2$ is an unsubstituted $C_{18}$ alkenyl. In embodiments, $R^2$ is an unsubstituted $C_{19}$ alkenyl. In embodiments, $R^2$ is an unsubstituted $C_{20}$ alkenyl. In embodiments, $R^2$ is an unsubstituted $C_{21}$ alkenyl. In embodiments, $R^2$ is an unsubstituted $C_{22}$ alkenyl. In embodiments, $R^2$ is an unsubstituted $C_{23}$ alkenyl. In embodiments, $R^2$ is an unsubstituted $C_{24}$ alkenyl. In embodiments, $R^2$ is an unsubstituted $C_{25}$ alkenyl. In embodiments, $R^2$ is an unsubstituted $C_{26}$ alkenyl. In embodiments, $R^2$ is an unsubstituted $C_{27}$ alkenyl. In embodiments, $R^2$ is an unsubstituted $C_{28}$ alkenyl. In embodiments, $R^2$ is an unsubstituted $C_{29}$ alkenyl. In embodiments, $R^2$ is an unsubstituted $C_{30}$ alkenyl.

In embodiments, $R^2$ is a substituted or unsubstituted $C_4$-$C_{30}$ alkyl. In embodiments, $R^2$ is a substituted or unsubstituted $C_4$-$C_{28}$ alkyl. In embodiments, $R^2$ is a substituted or unsubstituted $C_4$-$C_{26}$ alkyl. In embodiments, $R^2$ is a substituted or unsubstituted $C_4$-$C_{24}$ alkyl. In embodiments, $R^2$ is a substituted or unsubstituted $C_4$-$C_{22}$ alkyl. In embodiments, $R^2$ is an unsubstituted $C_4$-$C_{20}$ alkyl. In embodiments, $R^2$ is an unsubstituted $C_6$-$C_{18}$ alkyl. In embodiments, $R^2$ is an unsubstituted $C_{10}$-$C_{18}$ alkyl. In embodiments, $R^2$ is an unsubstituted $C_6$-$C_{18}$ alkyl. In embodiments, $R^2$ is a substituted $C_{15}$ alkyl. In embodiments, $R^2$ is a substituted $C_{17}$ alkyl. In embodiments, $R^2$ is an unsubstituted $C_{15}$ alkyl. In embodiments, $R^2$ is an unsubstituted $C_{17}$ alkyl.

In embodiments, $R^1$ is an unsubstituted $C_{10}$ alkyl and $R^2$ is an unsubstituted $C_{10}$ alkyl. In embodiments, $R^1$ is an unsubstituted $C_{10}$ alkyl and $R^2$ is an unsubstituted $C_{11}$ alkyl. In embodiments, $R^1$ is an unsubstituted $C_{10}$ alkyl and $R^2$ is an unsubstituted $C_{12}$ alkyl. In embodiments, $R^1$ is an unsubstituted $C_{10}$ alkyl and $R^2$ is an unsubstituted $C_{13}$ alkyl. In embodiments, $R^1$ is an unsubstituted $C_{10}$ alkyl and $R^2$ is an unsubstituted $C_{14}$ alkyl. In embodiments, $R^1$ is an unsubstituted $C_{10}$ alkyl and $R^2$ is an unsubstituted $C_{15}$ alkyl. In embodiments, $R^1$ is an unsubstituted $C_{10}$ alkyl and $R^2$ is an unsubstituted $C_{16}$ alkyl. In embodiments, $R^1$ is an unsubstituted $C_{10}$ alkyl and $R^2$ is an unsubstituted $C_{17}$ alkyl. In embodiments, $R^1$ is an unsubstituted $C_{10}$ alkyl and $R^2$ is an unsubstituted $C_{18}$ alkyl. In embodiments, $R^1$ is an unsubstituted $C_{10}$ alkyl and $R^2$ is an unsubstituted $C_{19}$ alkyl. In embodiments, $R^1$ is an unsubstituted $C_{10}$ alkyl and $R^2$ is an unsubstituted $C_{20}$ alkyl. In embodiments, $R^1$ is an unsubstituted $C_{10}$ alkyl and $R^2$ is an unsubstituted $C_{21}$ alkyl. In embodiments, $R^1$ is an unsubstituted $C_{10}$ alkyl and $R^2$ is an unsubstituted $C_{22}$ alkyl. In embodiments, $R^1$ is an unsubstituted $C_{10}$ alkyl and $R^2$ is an unsubstituted $C_{23}$ alkyl. In embodiments, $R^1$ is an unsubstituted $C_{11}$ alkyl and $R^2$ is an unsubstituted $C_{10}$ alkyl. In embodiments, $R^1$ is an unsubstituted $C_{11}$ alkyl and $R^2$ is an unsubstituted $C_{11}$ alkyl. In embodiments, $R^1$ is an unsubstituted $C_{11}$ alkyl and $R^2$ is an unsubstituted $C_{12}$ alkyl. In embodiments, $R^1$ is an unsubstituted $C_{11}$ alkyl and $R^2$ is an unsubstituted $C_{13}$ alkyl. In embodiments, $R^1$ is an unsubstituted $C_{11}$ alkyl and $R^2$ is an unsubstituted $C_{14}$ alkyl. In embodiments, $R^1$ is an unsubstituted $C_{11}$ alkyl and $R^2$ is an unsubstituted $C_{15}$ alkyl. In embodiments, $R^1$ is an unsubstituted $C_{11}$ alkyl and $R^2$ is an unsubstituted $C_{16}$ alkyl. In embodiments, $R^1$ is an unsubstituted $C_{11}$ alkyl and $R^2$ is an unsubstituted $C_{17}$ alkyl. In embodiments, $R^1$ is an unsubstituted $C_{11}$ alkyl and $R^2$ is an unsubstituted $C_{18}$ alkyl. In embodiments, $R^1$ is an unsubstituted $C_{11}$ alkyl and $R^2$ is an unsubstituted $C_{19}$ alkyl. In embodiments, $R^1$ is an unsubstituted $C_{11}$ alkyl and $R^2$ is an unsubstituted $C_{20}$ alkyl. In embodiments, $R^1$ is an unsubstituted $C_{11}$ alkyl and $R^2$ is an unsubstituted $C_{21}$ alkyl. In embodiments, $R^1$ is an unsubstituted $C_{11}$ alkyl and $R^2$ is an unsubstituted $C_{22}$ alkyl. In embodiments, $R^1$ is an unsubstituted $C_{11}$ alkyl and $R^2$ is an unsubstituted $C_{23}$ alkyl. In embodiments, $R^1$ is an unsubstituted $C_{12}$ alkyl and $R^2$ is an unsubstituted $C_{10}$ alkyl. In embodiments, $R^1$ is an unsubstituted $C_{12}$ alkyl and $R^2$ is an unsubstituted $C_{11}$ alkyl. In embodiments, $R^1$ is an unsubstituted $C_{12}$ alkyl and $R^2$ is an unsubstituted $C_{12}$ alkyl. In embodiments, $R^1$ is an unsubstituted $C_{12}$ alkyl and $R^2$ is an unsubstituted $C_{13}$ alkyl. In embodiments, $R^1$ is an unsubstituted $C_{12}$ alkyl and $R^2$ is an unsubstituted $C_{14}$ alkyl. In embodiments, $R^1$ is an unsubstituted $C_{12}$ alkyl and $R^2$ is an unsubstituted $C_{15}$ alkyl. In embodiments, $R^1$ is an unsubstituted $C_{12}$ alkyl and $R^2$ is an unsubstituted $C_{16}$ alkyl. In embodiments, $R^1$ is an unsubstituted $C_{12}$ alkyl and $R^2$ is an unsubstituted $C_{17}$ alkyl. In embodiments, $R^1$ is an unsubstituted $C_{12}$ alkyl and $R^2$ is an unsubstituted $C_{18}$ alkyl. In embodiments, $R^1$ is an unsubstituted $C_{12}$ alkyl and $R^2$ is an unsubstituted $C_{19}$ alkyl. In embodiments, $R^1$ is an unsubstituted $C_{12}$ alkyl and $R^2$ is an unsubstituted $C_{20}$ alkyl. In embodiments, $R^1$ is an unsubstituted $C_{12}$ alkyl and $R^2$ is an unsubstituted $C_{21}$ alkyl. In embodiments, $R^1$ is an unsubstituted $C_{12}$ alkyl and $R^2$ is an unsubstituted $C_{22}$ alkyl. In embodiments, $R^1$ is an unsubstituted $C_{12}$ alkyl and $R^2$ is an unsubstituted $C_{23}$ alkyl. In embodiments, $R^1$ is an unsubstituted $C_{13}$ alkyl and $R^2$ is an unsubstituted $C_{10}$ alkyl. In embodiments, $R^1$ is an unsubstituted $C_{13}$ alkyl and $R^2$ is an unsubstituted $C_{11}$ alkyl. In embodiments, $R^1$ is an unsubstituted $C_{13}$ alkyl and $R^2$ is an unsubstituted $C_{12}$ alkyl. In embodiments, $R^1$ is an unsubstituted $C_{13}$ alkyl and $R^2$ is an unsubstituted $C_{13}$ alkyl. In embodiments, $R^1$ is an unsubstituted $C_{13}$ alkyl and $R^2$ is an unsubstituted $C_{14}$ alkyl. In embodiments, $R^1$ is an unsubstituted $C_{13}$ alkyl and $R^2$ is an unsubstituted $C_{15}$ alkyl. In embodiments, $R^1$ is an unsubstituted $C_{13}$ alkyl and $R^2$ is an unsubstituted $C_{16}$ alkyl. In embodiments, $R^1$ is an unsubstituted $C_{13}$ alkyl and $R^2$ is an unsubstituted $C_{17}$ alkyl. In embodiments, $R^1$ is an unsubstituted $C_{13}$ alkyl and $R^2$ is an unsubstituted $C_{18}$ alkyl. In embodiments, $R^1$ is an unsubstituted $C_{13}$ alkyl and $R^2$ is an unsubstituted $C_{19}$ alkyl. In embodiments, $R^1$ is an unsubstituted $C_{13}$ alkyl and $R^2$ is an unsubstituted $C_{20}$ alkyl. In embodiments, $R^1$ is an unsubstituted $C_{13}$ alkyl and $R^2$ is an unsubstituted $C_{21}$ alkyl. In embodiments, $R^1$ is an unsubstituted $C_{13}$ alkyl and $R^2$ is an unsubstituted $C_{22}$ alkyl. In embodiments, $R^1$ is an unsubstituted $C_{13}$ alkyl and $R^2$ is an unsubstituted $C_{23}$ alkyl. In embodiments, $R^1$ is an unsubstituted $C_{14}$ alkyl and $R^2$ is an unsubstituted $C_{10}$ alkyl. In embodiments, $R^1$ is an unsubstituted $C_{14}$ alkyl and $R^2$ is an unsubstituted $C_{11}$ alkyl. In embodiments, $R^1$ is an unsubstituted $C_{14}$ alkyl and $R^2$ is an unsubstituted $C_{12}$ alkyl. In embodiments, $R^1$ is an unsubstituted $C_{14}$ alkyl and $R^2$ is an unsubstituted $C_{13}$ alkyl. In embodiments, $R^1$ is an unsubstituted $C_{14}$ alkyl and $R^2$ is an unsubstituted $C_{14}$ alkyl. In embodiments, $R^1$ is an unsubstituted $C_{14}$ alkyl and $R^2$ is an unsubstituted $C_{15}$ alkyl. In embodiments, $R^1$ is an unsubstituted $C_{14}$ alkyl and $R^2$ is an unsubstituted $C_{16}$ alkyl. In embodiments, $R^1$ is an unsubstituted $C_{14}$ alkyl and $R^2$ is an unsubstituted $C_{17}$ alkyl. In embodiments, $R^1$ is an unsubstituted $C_{14}$ alkyl and $R^2$ is an unsubstituted $C_{18}$ alkyl. In embodiments, $R^1$ is an unsubstituted $C_{14}$ alkyl and $R^2$ is an unsubstituted $C_{19}$ alkyl. In embodiments, $R^1$ is an unsubstituted $C_{14}$ alkyl and $R^2$ is an unsubstituted $C_{20}$ alkyl. In embodiments, $R^1$ is an unsubstituted $C_{14}$ alkyl and $R^2$ is an unsubstituted $C_{21}$ alkyl. In embodiments, $R^1$ is an unsubstituted $C_{14}$ alkyl and $R^2$ is an unsubstituted $C_{22}$ alkyl. In embodiments, $R^1$ is an unsubstituted $C_{14}$ alkyl and $R^2$ is an unsubstituted $C_{23}$ alkyl. In embodiments, $R^1$ is an unsubstituted $C_{15}$ alkyl and $R^2$ is an unsubstituted $C_{10}$ alkyl. In embodiments, $R^1$ is an unsubstituted $C_{15}$ alkyl and $R^2$ is an unsubstituted $C_{11}$ alkyl. In embodiments, $R^1$ is an unsubstituted $C_{15}$ alkyl and $R^2$ is an unsubstituted $C_{12}$ alkyl. In embodiments, $R^1$ is an unsubstituted $C_{15}$ alkyl and $R^2$ is an unsubstituted $C_{13}$ alkyl. In embodiments, $R^1$ is an unsubstituted $C_{15}$ alkyl and $R^2$ is an unsubstituted $C_{14}$ alkyl. In embodiments, $R^1$ is an unsubstituted $C_{15}$ alkyl and $R^2$ is an unsubstituted $C_{15}$ alkyl. In embodiments, $R^1$ is an unsubstituted $C_{15}$ alkyl and $R^2$ is an unsubstituted $C_{16}$ alkyl. In embodiments, $R^1$ is an unsubstituted $C_{15}$ alkyl and $R^2$ is an unsubstituted $C_{17}$ alkyl. In embodiments, $R^1$ is an unsubstituted $C_{15}$ alkyl and $R^2$ is an unsubstituted $C_{18}$ alkyl. In embodiments, $R^1$ is an unsubstituted $C_{15}$ alkyl and $R^2$ is an unsubstituted $C_{19}$ alkyl. In embodiments, $R^1$ is an unsubstituted $C_{15}$ alkyl and $R^2$ is an unsubstituted $C_{20}$ alkyl. In embodiments, $R^1$ is an unsubstituted $C_{15}$ alkyl and $R^2$ is an unsubstituted $C_{21}$ alkyl. In embodiments, $R^1$ is an unsubstituted $C_{15}$ alkyl and $R^2$ is an unsubstituted $C_{22}$ alkyl. In embodiments, $R^1$ is an unsubstituted $C_{15}$ alkyl and $R^2$ is an unsubstituted $C_{23}$ alkyl. In embodiments, $R^1$ is an unsubstituted $C_{16}$ alkyl and $R^2$ is an unsubstituted $C_{10}$ alkyl. In embodiments, $R^1$ is an unsubstituted $C_{16}$ alkyl and $R^2$ is an unsubstituted $C_{11}$ alkyl. In embodiments, $R^1$ is an unsubstituted $C_{16}$ alkyl and $R^2$ is an unsubstituted $C_{12}$ alkyl. In embodiments, $R^1$ is an unsubstituted $C_{16}$ alkyl and $R^2$ is an unsubstituted $C_{13}$ alkyl. In embodiments, $R^1$ is an unsubstituted $C_{16}$ alkyl and $R^2$ is an unsubstituted $C_{14}$ alkyl. In embodiments, $R^1$ is an unsubstituted $C_{16}$ alkyl and $R^2$ is an unsubstituted $C_{15}$ alkyl. In embodiments, $R^1$ is an unsubstituted $C_{16}$ alkyl and $R^2$ is an unsubstituted $C_{16}$ alkyl. In embodiments, $R^1$ is an unsubstituted $C_{16}$ alkyl and $R^2$ is an unsubstituted $C_{17}$ alkyl. In embodiments, $R^1$ is an unsubstituted $C_{16}$ alkyl and $R^2$ is an unsubstituted $C_{18}$ alkyl. In embodiments, $R^1$ is an unsubstituted $C_{16}$ alkyl and $R^2$ is an unsubstituted $C_{19}$ alkyl. In embodiments, $R^1$ is an unsubstituted $C_{16}$ alkyl and $R^2$ is an unsubstituted $C_{20}$ alkyl. In embodiments, $R^1$ is an unsubstituted $C_{16}$ alkyl and $R^2$ is an unsubstituted $C_{21}$ alkyl. In embodiments, $R^1$ is an unsubstituted $C_{16}$ alkyl and $R^2$ is an unsubstituted $C_{22}$ alkyl. In embodiments, $R^1$ is an unsubstituted $C_{16}$ alkyl and $R^2$ is an unsubstituted $C_{23}$ alkyl. In embodiments, $R^1$ is an unsubstituted $C_{17}$ alkyl and $R^2$ is an unsubstituted $C_{10}$ alkyl. In embodiments, $R^1$ is an unsubstituted $C_{17}$ alkyl and $R^2$ is an unsubstituted $C_{11}$ alkyl. In embodiments, $R^1$ is an unsubstituted $C_{17}$ alkyl and $R^2$ is an unsubstituted $C_{12}$ alkyl. In embodiments, $R^1$ is an unsubstituted $C_{17}$ alkyl and $R^2$ is an unsubstituted $C_{13}$ alkyl. In embodiments, $R^1$ is an unsubstituted $C_{17}$ alkyl and $R^2$ is an unsubstituted $C_{14}$ alkyl. In embodiments, $R^1$ is an unsubstituted $C_{17}$ alkyl and $R^2$ is an unsubstituted $Cl_5$ alkyl. In embodiments, $R^1$ is an unsubstituted $C_{17}$ alkyl and $R^2$ is an unsubstituted $C_{16}$ alkyl. In embodiments, $R^1$ is an unsubstituted $C_{17}$ alkyl and $R^2$ is an unsubstituted $C_{17}$ alkyl. In embodiments, $R^1$ is an unsubstituted $C_{17}$ alkyl and $R^2$ is an unsubstituted $C_{18}$ alkyl. In embodiments, $R^1$ is an unsubstituted $C_{17}$ alkyl and $R^2$ is an unsubstituted $C_{19}$ alkyl. In embodiments, $R^1$ is an unsubstituted $C_{17}$ alkyl and $R^2$ is an unsubstituted $C_{20}$ alkyl. In embodiments, $R^1$ is an unsubstituted $C_{17}$ alkyl and $R^2$ is an unsubstituted $C_{21}$ alkyl. In embodiments, $R^1$ is an unsubstituted $C_{17}$ alkyl and $R^2$ is an unsubstituted $C_{22}$ alkyl. In embodiments, $R^1$ is an unsubstituted $C_{17}$ alkyl and $R^2$ is an unsubstituted $C_{23}$ alkyl. In embodiments, $R^1$ is an unsubstituted $C_{18}$ alkyl and $R^2$ is an unsubstituted $C_{10}$ alkyl. In embodiments, $R^1$ is an unsubstituted $C_{18}$ alkyl and $R^2$ is an unsubstituted $C_{11}$ alkyl. In embodiments, $R^1$ is an unsubstituted $C_{18}$ alkyl and $R^2$ is an unsubstituted $C_{12}$ alkyl. In embodiments, $R^1$ is an unsubstituted $C_{18}$ alkyl and $R^2$ is an unsubstituted $C_{13}$ alkyl. In embodiments, $R^1$ is an unsubstituted $C_{18}$ alkyl and $R^2$ is an unsubstituted $C_{14}$ alkyl. In embodiments, $R^1$ is an unsubstituted $C_{18}$ alkyl and $R^2$ is an unsubstituted $C_{15}$ alkyl. In embodiments, $R^1$ is an unsubstituted $C_{18}$ alkyl and $R^2$ is an unsubstituted $C_{16}$ alkyl. In embodiments, $R^1$ is an unsubstituted $C_{18}$ alkyl and $R^2$ is an unsubstituted $C_{17}$ alkyl. In embodiments, $R^1$ is an unsubstituted $C_{18}$ alkyl and $R^2$ is an unsubstituted $C_{18}$ alkyl. In embodiments, $R^1$ is an unsubstituted $C_{18}$ alkyl and $R^2$ is an unsubstituted $C_{19}$ alkyl. In embodiments, $R^1$ is an unsubstituted $C_{18}$ alkyl and $R^2$ is an unsubstituted $C_{20}$ alkyl. In embodiments, $R^1$ is an unsubstituted $C_{18}$ alkyl and $R^2$ is an unsubstituted $C_{21}$ alkyl. In embodiments, $R^1$ is an unsubstituted $C_{18}$ alkyl and $R^2$ is an unsubstituted $C_{22}$ alkyl. In embodiments, $R^1$ is an unsubstituted $C_{18}$ alkyl and $R^2$ is an unsubstituted $C_{23}$ alkyl. In embodiments, $R^1$ is an unsubstituted $C_{19}$ alkyl and $R^2$ is an unsubstituted $C_{10}$ alkyl. In embodiments, $R^1$ is an unsubstituted $C_{19}$ alkyl and $R^2$ is an unsubstituted $C_{11}$ alkyl. In embodiments, $R^1$ is an unsubstituted $C_{19}$ alkyl and $R^2$ is an unsubstituted $C_{12}$ alkyl. In embodiments, $R^1$ is an unsubstituted $C_{19}$ alkyl and $R^2$ is an unsubstituted $C_{13}$ alkyl. In embodiments, $R^1$ is an unsubstituted $C_{19}$ alkyl and $R^2$ is an unsubstituted $C_{14}$ alkyl. In embodiments, $R^1$ is an unsubstituted $C_{19}$ alkyl and $R^2$ is an unsubstituted $C_{15}$ alkyl. In embodiments, $R^1$ is an unsubstituted $C_{19}$ alkyl and $R^2$ is an unsubstituted $C_{16}$ alkyl. In embodiments, $R^1$ is an unsubstituted $C_{19}$ alkyl and $R^2$ is an unsubstituted $C_{17}$ alkyl. In embodiments, $R^1$ is an unsubstituted $C_{19}$ alkyl and $R^2$ is an unsubstituted $C_{18}$ alkyl. In embodiments, $R^1$ is an unsubstituted $C_{19}$ alkyl and $R^2$ is an unsubstituted $C_{19}$ alkyl. In embodiments, $R^1$ is an unsubstituted $C_{19}$ alkyl and $R^2$ is an unsubstituted $C_{20}$ alkyl. In embodiments, $R^1$ is an unsubstituted $C_{19}$ alkyl and $R^2$ is an unsubstituted $C_{21}$ alkyl. In embodiments, $R^1$ is an unsubstituted $C_{19}$ alkyl and $R^2$ is an unsubstituted $C_{22}$ alkyl. In embodiments, $R^1$ is an unsubstituted $C_{19}$ alkyl and $R^2$ is an unsubstituted $C_{23}$ alkyl. In embodiments, $R^1$ is an unsubstituted $C_{20}$ alkyl and $R^2$ is an unsubstituted $C_{10}$ alkyl. In embodiments, $R^1$ is an unsubstituted $C_{20}$ alkyl and $R^2$ is an unsubstituted $C_{11}$ alkyl. In embodiments, $R^1$ is an unsubstituted $C_{20}$ alkyl and $R^2$ is an unsubstituted $C_{12}$ alkyl. In embodiments, $R^1$ is an unsubstituted $C_{20}$ alkyl and $R^2$ is an unsubstituted $C_{13}$ alkyl. In embodiments, $R^1$ is an unsubstituted $C_{20}$ alkyl and $R^2$ is an unsubstituted $C_{14}$ alkyl. In embodiments, $R^1$ is an unsubstituted $C_{20}$ alkyl and $R^2$ is an unsubstituted $C_{15}$ alkyl. In embodiments, $R^1$ is an unsubstituted $C_{20}$ alkyl and $R^2$ is an unsubstituted $C_{16}$ alkyl. In embodiments, $R^1$ is an unsubstituted $C_{20}$ alkyl and $R^2$ is an unsubstituted $C_{17}$ alkyl. In embodiments, $R^1$ is an unsubstituted $C_{20}$ alkyl and $R^2$ is an unsubstituted $C_{18}$ alkyl. In embodiments, $R^1$ is an unsubstituted $C_{20}$ alkyl and $R^2$ is an unsubstituted $C_{19}$ alkyl. In embodiments, $R^1$ is an unsubstituted $C_{20}$ alkyl and $R^2$ is an unsubstituted $C_{20}$ alkyl. In embodiments, $R^1$ is an unsubstituted $C_{20}$ alkyl and $R^2$ is an unsubstituted $C_{21}$ alkyl. In embodiments, $R^1$ is an unsubstituted $C_{20}$ alkyl and $R^2$ is an unsubstituted $C_{22}$ alkyl. In embodiments, $R^1$ is an unsubstituted $C_{20}$ alkyl and $R^2$ is an unsubstituted $C_{23}$ alkyl. In embodiments, $R^1$ is an unsubstituted $C_{21}$ alkyl and $R^2$ is an unsubstituted $C_{10}$ alkyl. In embodiments, $R^1$ is an unsubstituted $C_{21}$ alkyl and $R^2$ is an unsubstituted $C_{11}$ alkyl. In embodiments, $R^1$ is an unsubstituted $C_{21}$ alkyl and $R^2$ is an unsubstituted $C_{12}$ alkyl. In embodiments, $R^1$ is an unsubstituted $C_{21}$ alkyl and $R^2$ is an unsubstituted $C_{13}$ alkyl. In embodiments, $R^1$ is an unsubstituted $C_{21}$ alkyl and $R^2$ is an unsubstituted $C_{14}$ alkyl. In embodiments, $R^1$ is an unsubstituted $C_{21}$ alkyl and $R^2$ is an unsubstituted $C_{15}$ alkyl. In embodiments, $R^1$ is an unsubstituted $C_{21}$ alkyl and $R^2$ is an unsubstituted $C_{16}$ alkyl. In embodiments, $R^1$ is an unsubstituted $C_{21}$ alkyl and $R^2$ is an unsubstituted $C_{17}$ alkyl. In embodiments, $R^1$ is an unsubstituted $C_{21}$ alkyl and $R^2$ is an unsubstituted $C_{18}$ alkyl. In embodiments, $R^1$ is an unsubstituted $C_{21}$ alkyl and $R^2$ is an unsubstituted $C_{19}$ alkyl. In embodiments, $R^1$ is an unsubstituted $C_{21}$ alkyl and $R^2$ is an unsubstituted $C_{20}$ alkyl. In embodiments, $R^1$ is an unsubstituted $C_{21}$ alkyl and $R^2$ is an unsubstituted $C_{21}$ alkyl. In embodiments, $R^1$ is an unsubstituted $C_{21}$ alkyl and $R^2$ is an unsubstituted $C_{22}$ alkyl. In embodiments, $R^1$ is an unsubstituted $C_{21}$ alkyl and $R^2$ is an unsubstituted $C_{23}$ alkyl. In embodiments, $R^1$ is an unsubstituted $C_{22}$ alkyl and $R^2$ is an unsubstituted $C_{10}$ alkyl. In embodiments, $R^1$ is an unsubstituted $C_{22}$ alkyl and $R^2$ is an unsubstituted $C_{11}$ alkyl. In embodiments, $R^1$ is an unsubstituted $C_{22}$ alkyl and $R^2$ is an unsubstituted $C_{12}$ alkyl. In embodiments, $R^1$ is an unsubstituted $C_{22}$ alkyl and $R^2$ is an unsubstituted $C_{13}$ alkyl. In embodiments, $R^1$ is an unsubstituted $C_{22}$ alkyl and $R^2$ is an unsubstituted $C_{14}$ alkyl. In embodiments, $R^1$ is an unsubstituted $C_{22}$ alkyl and $R^2$ is an unsubstituted $C_{15}$ alkyl. In embodiments, $R^1$ is an unsubstituted $C_{22}$ alkyl and $R^2$ is an unsubstituted $C_{16}$ alkyl. In embodiments, $R^1$ is an unsubstituted $C_{22}$ alkyl and $R^2$ is an unsubstituted $C_{17}$ alkyl. In embodiments, $R^1$ is an unsubstituted $C_{22}$ alkyl and $R^2$ is an unsubstituted $C_{18}$ alkyl. In embodiments, $R^1$ is an unsubstituted $C_{22}$ alkyl and $R^2$ is an unsubstituted $C_{19}$ alkyl. In embodiments, $R^1$ is an unsubstituted $C_{22}$ alkyl and $R^2$ is an unsubstituted $C_{20}$ alkyl. In embodiments, $R^1$ is an unsubstituted $C_{22}$ alkyl and $R^2$ is an unsubstituted $C_{21}$ alkyl. In embodiments, $R^1$ is an unsubstituted $C_{22}$ alkyl and $R^2$ is an unsubstituted $C_{22}$ alkyl. In embodiments, $R^1$ is an unsubstituted $C_{22}$ alkyl and $R^2$ is an unsubstituted $C_{23}$ alkyl. In embodiments, $R^1$ is an unsubstituted $C_{23}$ alkyl and $R^2$ is an unsubstituted $C_{10}$ alkyl. In embodiments, $R^1$ is an unsubstituted $C_{23}$ alkyl and $R^2$ is an unsubstituted $C_{11}$ alkyl. In embodiments, $R^1$ is an unsubstituted $C_{23}$ alkyl and $R^2$ is an unsubstituted $C_{12}$ alkyl. In embodiments, $R^1$ is an unsubstituted $C_{23}$ alkyl and $R^2$ is an unsubstituted $C_{13}$ alkyl. In embodiments, $R^1$ is an unsubstituted $C_{23}$ alkyl and $R^2$ is an unsubstituted $C_{14}$ alkyl. In embodiments, $R^1$ is an unsubstituted $C_{23}$ alkyl and $R^2$ is an unsubstituted $C_{15}$ alkyl. In embodiments, $R^1$ is an unsubstituted $C_{23}$ alkyl and $R^2$ is an unsubstituted $C_{16}$ alkyl. In embodiments, $R^1$ is an unsubstituted $C_{23}$ alkyl and $R^2$ is an unsubstituted $C_{17}$ alkyl. In embodiments, $R^1$ is an unsubstituted $C_{23}$ alkyl and $R^2$ is an unsubstituted $C_{18}$ alkyl. In embodiments, $R^1$ is an unsubstituted $C_{23}$ alkyl and $R^2$ is an unsubstituted $C_{19}$ alkyl. In embodiments, $R^1$ is an unsubstituted $C_{23}$ alkyl and $R^2$ is an unsubstituted $C_{20}$ alkyl. In embodiments, $R^1$ is an unsubstituted $C_{23}$ alkyl and $R^2$ is an unsubstituted $C_{21}$ alkyl. In embodiments, $R^1$ is an unsubstituted $C_{23}$ alkyl and $R^2$ is an unsubstituted $C_{22}$ alkyl. In embodiments, $R^1$ is an unsubstituted $C_{23}$ alkyl and $R^2$ is an unsubstituted $C_{23}$ alkyl.

In embodiments, the membrane protein is a G protein-coupled receptor.

In embodiments, the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

In embodiments, the membrane protein is a 5-hydroxytryptamine receptor (e.g., 5-hydroxytryptamine receptor 1A corresponding to Human protein RefSeq NP_000515, 5-hydroxytryptamine receptor 1B corresponding to Human protein RefSeq NP_000854, 5-hydroxytryptamine receptor 1D corresponding to Human protein RefSeq NP_000855, 5-hydroxytryptamine receptor 1E corresponding to Human protein RefSeq NP_000856, 5-hydroxytryptamine receptor 1F corresponding to Human protein RefSeq NP_000857, 5-hydroxytryptamine receptor 2A corresponding to Human protein RefSeq NP_000612, 5-hydroxytryptamine receptor 2B corresponding to Human protein RefSeq NP_000858, 5-hydroxytryptamine receptor 2C corresponding to Human protein RefSeq NP_000859, 5-hydroxytryptamine receptor 4 corresponding to Human protein RefSeq NP_000861, 5-hydroxytryptamine receptor 5A corresponding to Human protein RefSeq NP_076917, 5-hydroxytryptamine receptor 5B, pseudogene corresponding to Human protein RefSeq, 5-hydroxytryptamine receptor 6 corresponding to Human protein RefSeq NP_000862, 5-hydroxytryptamine receptor 7 corresponding to Human protein RefSeq NP_000863).

In embodiments, the membrane protein is an acetylcholine receptor (e.g., cholinergic receptor muscarinic 1 corresponding to Human protein RefSeq NP_000729, cholinergic receptor muscarinic 2 corresponding to Human protein RefSeq NP_000730, cholinergic receptor muscarinic 3 corresponding to Human protein RefSeq NP_000731, cholinergic receptor muscarinic 4 corresponding to Human protein RefSeq NP_000732, cholinergic receptor muscarinic 5 corresponding to Human protein RefSeq NP_036257).

In embodiments, the membrane protein is an adenosine receptor (e.g., adenosine A1 receptor corresponding to Human protein RefSeq NP_000665, adenosine A2a receptor corresponding to Human protein RefSeq NP_000666, adenosine A2b receptor corresponding to Human protein RefSeq NP_000667, adenosine A3 receptor corresponding to Human protein RefSeq NP_000668).

In embodiments, the membrane protein is an angiotensin receptor (e.g., angiotensin II receptor type 1 corresponding to Human protein RefSeq NP_000676, angiotensin II receptor type 2 corresponding to Human protein RefSeq NP_000677).

In embodiments, the membrane protein is an apelin receptor (e.g., apelin receptor corresponding to Human protein RefSeq NP_005152).

In embodiments, the membrane protein is a bile acid receptor (e.g., G protein-coupled bile acid receptor 1 corresponding to Human protein RefSeq NP_001070662).

In embodiments, the membrane protein is a bombesin receptor (e.g., neuromedin B receptor corresponding to Human protein RefSeq NP_002502, gastrin releasing peptide receptor corresponding to Human protein RefSeq NP_005305, bombesin receptor subtype 3 corresponding to Human protein RefSeq NP_001718).

In embodiments, the membrane protein is a bradykinin receptor (e.g., bradykinin receptor B1 corresponding to Human protein RefSeq NP_000701, bradykinin receptor B2 corresponding to Human protein RefSeq NP_000614).

In embodiments, the membrane protein is a cannabinoid receptor (e.g., cannabinoid receptor 1 corresponding to Human protein RefSeq NP_057167, cannabinoid receptor 2 corresponding to Human protein RefSeq NP_001832).

In embodiments, the membrane protein is a chemerin receptor (e.g., chemerin chemokine-like receptor 1 corresponding to Human protein RefSeq NP_004063).

In embodiments, the membrane protein is a chemokine receptor (e.g., C-C motif chemokine receptor 1 corresponding to Human protein RefSeq NP_001286, C-C motif chemokine receptor 2 corresponding to Human protein RefSeq NP_001116513 |NP_001116868, C-C motif chemokine receptor 3 corresponding to Human protein RefSeq NP_001828, C-C motif chemokine receptor 4 corresponding to Human protein RefSeq NP_005499, C-C motif chemokine receptor 5 (gene/pseudogene) corresponding to Human protein RefSeq NP_000570, C-C motif chemokine receptor 6 corresponding to Human protein RefSeq NP_004358, C-C motif chemokine receptor 7 corresponding to Human protein RefSeq NP_001829, C-C motif chemokine receptor 8 corresponding to Human protein RefSeq NP_005192, C-C motif chemokine receptor 9 corresponding to Human protein RefSeq NP_006632, C-C motif chemokine receptor 10 corresponding to Human protein RefSeq NP_057686, C-X-C motif chemokine receptor 1 corresponding to Human protein RefSeq NP_000625, C-X-C motif chemokine receptor 2 corresponding to Human protein RefSeq NP_001548, C-X-C motif chemokine receptor 3 corresponding to Human protein RefSeq NP_001495, C-X-C motif chemokine receptor 4 corresponding to Human protein RefSeq NP_003458, C-X-C motif chemokine receptor 5 corresponding to Human protein RefSeq NP_0017071NP_116743, C-X-C motif chemokine receptor 6 corresponding to Human protein RefSeq NP_006555, C-X3-C motif chemokine receptor 1 corresponding to Human protein RefSeq NP_001328, X-C motif chemokine receptor 1 corresponding to Human protein RefSeq NP_005274, atypical chemokine receptor 1 (Duffy blood group) corresponding to Human protein RefSeq NP_002027, atypical chemokine receptor 2 corresponding to Human protein RefSeq NP_001287, atypical chemokine receptor 3 corresponding to Human protein RefSeq NP_064707, atypical chemokine receptor 4 corresponding to Human protein RefSeq NP_848540, C-C motif chemokine receptor like 2 corresponding to Human protein RefSeq NP_003956).

In embodiments, the membrane protein is a cholecystokinin receptor (e.g., cholecystokinin A receptor corresponding to Human protein RefSeq NP_000721, cholecystokinin B receptor corresponding to Human protein RefSeq NP_795344).

In embodiments, the membrane protein is a Class A Orphan receptor (e.g., G protein-coupled receptor 1 corresponding to Human protein RefSeq NP_005270, G protein-coupled receptor 3 corresponding to Human protein RefSeq NP_005272, bombesin receptor subtype 3 corresponding to Human protein RefSeq NP_001718, G protein-coupled receptor 4 corresponding to Human protein RefSeq NP_005273, G protein-coupled receptor 42 (gene/pseudogene) corresponding to Human protein RefSeq NP_005295, G protein-coupled receptor 6 corresponding to Human protein RefSeq NP_005275, G protein-coupled receptor 12 corresponding to Human protein RefSeq NP_005279, G protein-coupled receptor 15 corresponding to Human protein RefSeq NP_005281, G protein-coupled receptor 17 corresponding to Human protein RefSeq NP_005282, G protein-coupled receptor 18 corresponding to Human protein RefSeq NP_005283, G protein-coupled receptor 19 corresponding to Human protein RefSeq NP_006134, G protein-coupled receptor 20 corresponding to Human protein RefSeq NP_005284, G protein-coupled receptor 21 corresponding to Human protein RefSeq NP_005285, G protein-coupled receptor 22 corresponding to Human protein RefSeq NP_005286, G protein-coupled receptor 25 corresponding to Human protein RefSeq NP_005289, G protein-coupled receptor 26 corresponding to Human protein RefSeq NP_703143, G protein-coupled receptor 27 corresponding to Human protein RefSeq NP_061844, G protein-coupled receptor 31 corresponding to Human protein RefSeq NP_005290, G protein-coupled receptor 32 corresponding to Human protein RefSeq NP_001497, G protein-coupled receptor 33 (gene/pseudogene) corresponding to Human protein RefSeq NP_001184113, G protein-coupled receptor 34 corresponding to Human protein RefSeq NP_005291, G protein-coupled receptor 35 corresponding to Human protein RefSeq NP_005292, G protein-coupled receptor 37 corresponding to Human protein RefSeq NP_005293, G protein-coupled receptor 37 like 1 corresponding to Human protein RefSeq NP_004758, G protein-coupled receptor 39 corresponding to Human protein RefSeq NP_001499, G protein-coupled receptor 45 corresponding to Human protein RefSeq NP_009158, G protein-coupled receptor 50 corresponding to Human protein RefSeq NP_004215, G protein-coupled receptor 52 corresponding to Human protein RefSeq NP_005675, G protein-coupled receptor 55 corresponding to Human protein RefSeq NP_005674, G protein-coupled receptor 61 corresponding to Human protein RefSeq NP_114142, G protein-coupled receptor 62 corresponding to Human protein RefSeq NP_543141, G protein-coupled receptor 63 corresponding to Human protein RefSeq NP_110411, G protein-coupled receptor 65 corresponding to Human protein RefSeq NP_003599, G protein-coupled receptor 68 corresponding to Human protein RefSeq NP_003476, G protein-coupled receptor 75 corresponding to Human protein RefSeq NP_006785, G protein-coupled receptor 78 corresponding to Human protein RefSeq NP_543009, G protein-coupled receptor 79, pseudogene corresponding to Human protein RefSeq, G protein-coupled receptor 82 corresponding to Human protein RefSeq NP_543007, G protein-coupled receptor 83 corresponding to Human protein RefSeq NP_057624, G protein-coupled receptor 84 corresponding to Human protein RefSeq NP_065103, G protein-coupled receptor 85 corresponding to Human protein RefSeq NP_061842, G protein-coupled receptor 87 corresponding to Human protein RefSeq NP_076404, G protein-coupled receptor 88 corresponding to Human protein RefSeq NP_071332, G protein-coupled receptor 101 corresponding to Human protein RefSeq NP_473362, G protein-coupled receptor 119 corresponding to Human protein RefSeq NP_848566, G protein-coupled receptor 132 corresponding to Human protein RefSeq NP_037477, G protein-coupled receptor 135 corresponding to Human protein RefSeq NP_072093, G protein-coupled receptor 139 corresponding to Human protein RefSeq NP_001002911, G protein-coupled receptor 141 corresponding to Human protein RefSeq NP_861456, G protein-coupled receptor 142 corresponding to Human protein RefSeq NP_861455, G protein-coupled receptor 146 corresponding to Human protein RefSeq NP_612454, G protein-coupled receptor 148 corresponding to Human protein RefSeq NP_997247, G protein-coupled receptor 149 corresponding to Human protein RefSeq NP_001033794, G protein-coupled receptor 150 corresponding to Human protein RefSeq NP_954713, G protein-coupled receptor 151 corresponding to Human protein RefSeq NP_919227, G protein-coupled receptor 152 corresponding to Human protein RefSeq NP_996880, G protein-coupled receptor 153 corresponding to Human protein RefSeq NP_997253, G protein-coupled receptor 160 corresponding to Human protein RefSeq NP_055188, G protein-coupled receptor 161 corresponding to Human protein RefSeq NP_722561, G protein-coupled receptor 162 corresponding to Human protein RefSeq NP_062832, G protein-coupled receptor 171 corresponding to Human protein RefSeq NP_013308, G protein-coupled receptor 173 corresponding to Human protein RefSeq NP_061842, G protein-coupled receptor 174 corresponding to Human protein RefSeq NP_115942, G protein-coupled receptor 176 corresponding to Human protein RefSeq NP_009154, G protein-coupled receptor 182 corresponding to Human protein RefSeq NP_009195, G protein-coupled receptor 183 corresponding to Human protein RefSeq NP_004942, leucine rich repeat containing G protein-coupled receptor 4 corresponding to Human protein RefSeq NP_060960, leucine rich repeat containing G protein-coupled receptor 5 corresponding to Human protein RefSeq NP_003658, leucine rich repeat containing G protein-coupled receptor 6 corresponding to Human protein RefSeq NP_067649, MAS 1 proto-oncogene, G protein-coupled receptor corresponding to Human protein RefSeq NP_002368, MAS 1 proto-oncogene like, G protein-coupled receptor corresponding to Human protein RefSeq NP_443199, MAS related GPR family member D corresponding to Human protein RefSeq NP_944605, MAS related GPR family member E corresponding to Human protein RefSeq NP_001034254, MAS related GPR family member F corresponding to Human protein RefSeq NP_659452, MAS related GPR family member G corresponding to Human protein RefSeq NP_001157849, MAS related GPR family member X1 corresponding to Human protein RefSeq NP_671732, MAS related GPR family member X2 corresponding to Human protein RefSeq NP_054030, MAS related GPR family member X3 corresponding to Human protein RefSeq NP_473372, MAS related GPR family member X4 corresponding to Human protein RefSeq NP_473373, P2Y receptor family member 8 corresponding to Human protein RefSeq NP_835230, P2Y receptor family member 10 corresponding to Human protein RefSeq NP_055314, trace amine associated receptor 2 (gene/pseudogene) corresponding to Human protein RefSeq NP_001028252, trace amine associated receptor 3, pseudogene corresponding to Human protein RefSeq, trace amine associated receptor 4, pseudogene corresponding to Human protein RefSeq, trace amine associated receptor 5 corresponding to Human protein RefSeq NP_003958, trace amine associated receptor 6 corresponding to Human protein RefSeq NP_778237, trace amine associated receptor 8 corresponding to Human protein RefSeq NP_444508, trace amine associated receptor 9 (gene/pseudogene) corresponding to Human protein RefSeq NP_778227).

In embodiments, the membrane protein is a Class C Orphan Receptor (e.g., G protein-coupled receptor 156 corresponding to Human protein RefSeq NP_694547, G protein-coupled receptor 158 corresponding to Human protein RefSeq NP_065803, G protein-coupled receptor 179 corresponding to Human protein RefSeq NP_001004334, G protein-coupled receptor class C group 5 member A corresponding to Human protein RefSeq NP_003970, G protein-coupled receptor class C group 5 member B corresponding to Human protein RefSeq NP_057319, G protein-coupled receptor class C group 5 member C corresponding to Human protein RefSeq NP_061123, G protein-coupled receptor class C group 5 member D corresponding to Human protein RefSeq NP_061124, G protein-coupled receptor class C group 6 member A corresponding to Human protein RefSeq NP_683766).

In embodiments, the membrane protein is a dopamine receptor (e.g., dopamine receptor D1 corresponding to Human protein RefSeq NP_000785, dopamine receptor D2 corresponding to Human protein RefSeq NP_000786, dopamine receptor D3 corresponding to Human protein RefSeq NP_000787, dopamine receptor D4 corresponding to Human protein RefSeq NP_000788, dopamine receptor D5 corresponding to Human protein RefSeq NP_000789).

In embodiments, the membrane protein is an endothelin receptor (e.g., endothelin receptor type A corresponding to Human protein RefSeq NP_001948, endothelin receptor type B corresponding to Human protein RefSeq NP_000106).

In embodiments, the membrane protein is a formyl peptide receptor (e.g., formyl peptide receptor 1 corresponding to Human protein RefSeq NP_002020, formyl peptide receptor 2 corresponding to Human protein RefSeq NP_001453, formyl peptide receptor 3 corresponding to Human protein RefSeq NP_002021).

In embodiments, the membrane protein is a free fatty acid receptor (e.g., free fatty acid receptor 1 corresponding to Human protein RefSeq NP_005294, free fatty acid receptor 2 corresponding to Human protein RefSeq NP_005297, free fatty acid receptor 3 corresponding to Human protein RefSeq NP_005295, free fatty acid receptor 4 corresponding to Human protein RefSeq NP_859529, G protein-coupled receptor 42 (gene/pseudogene) corresponding to Human protein RefSeq NP_005295).

In embodiments, the membrane protein is a galanin receptor (e.g., galanin receptor 1 corresponding to Human protein RefSeq NP_001471, galanin receptor 2 corresponding to Human protein RefSeq NP_003848, galanin receptor 3 corresponding to Human protein RefSeq NP_003605).

In embodiments, the membrane protein is a ghrelin receptor (e.g., growth hormone secretagogue receptor corresponding to Human protein RefSeq NP_940799).

In embodiments, the membrane protein is a glycoprotein hormone receptor (e.g., follicle stimulating hormone receptor corresponding to Human protein RefSeq NP_000136, luteinizing hormone/choriogonadotropin receptor corresponding to Human protein RefSeq NP_000224, thyroid stimulating hormone receptor corresponding to Human protein RefSeq NP_000360).

In embodiments, the membrane protein is a gonadotrophin-releasing hormone receptor (e.g., gonadotropin releasing hormone receptor corresponding to Human protein RefSeq NP_000397)).

In embodiments, the membrane protein is a G protein-coupled estrogen receptor (e.g., G protein-coupled estrogen receptor 1 corresponding to Human protein RefSeq NP_001496).

In embodiments, the membrane protein is a histamine receptor (e.g., histamine receptor H1 corresponding to Human protein RefSeq NP_000852, histamine receptor H2 corresponding to Human protein RefSeq NP_071640, histamine receptor H3 corresponding to Human protein RefSeq NP_009163, histamine receptor H4 corresponding to Human protein RefSeq NP_067637).

In embodiments, the membrane protein is a hydroxycarboxylic acid receptor (e.g., hydroxycarboxylic acid receptor 1 corresponding to Human protein RefSeq NP_115943, hydroxycarboxylic acid receptor 2 corresponding to Human protein RefSeq NP_808219, hydroxycarboxylic acid receptor 3 corresponding to Human protein RefSeq NP_006009).

In embodiments, the membrane protein is a kisspeptin receptor (e.g., KISS1 receptor corresponding to Human protein RefSeq NP_115940).

In embodiments, the membrane protein is a leukotriene receptor (e.g., leukotriene B4 receptor corresponding to Human protein RefSeq NP_858043, leukotriene B4 receptor 2 corresponding to Human protein RefSeq NP_062813, cysteinyl leukotriene receptor 1 corresponding to Human protein RefSeq NP_006630, cysteinyl leukotriene receptor 2 corresponding to Human protein RefSeq NP_065110, oxoeicosanoid receptor 1 corresponding to Human protein RefSeq NP_683765, formyl peptide receptor 2 corresponding to Human protein RefSeq NP_001453).

In embodiments, the membrane protein is a lysophospholipid receptor (e.g., lysophosphatidic acid receptor 1 corresponding to Human protein RefSeq NP_001392, lysophosphatidic acid receptor 2 corresponding to Human protein RefSeq NP_004711, lysophosphatidic acid receptor 3 corresponding to Human protein RefSeq NP_036284, lysophosphatidic acid receptor 4 corresponding to Human protein RefSeq NP_005287, lysophosphatidic acid receptor 5 corresponding to Human protein RefSeq NP_065133, lysophosphatidic acid receptor 6 corresponding to Human protein RefSeq NP_005758).

In embodiments, the membrane protein is a lysophospholipid S1P receptor (e.g., sphingosine-1-phosphate receptor 1 corresponding to Human protein RefSeq NP_001391, sphingosine-1-phosphate receptor 2 corresponding to Human protein RefSeq NP_004221, sphingosine-1-phosphate receptor 3 corresponding to Human protein RefSeq NP_005217, sphingosine-1-phosphate receptor 4 corresponding to Human protein RefSeq NP_003766, sphingosine-1-phosphate receptor 5 corresponding to Human protein RefSeq NP_110387).

In embodiments, the membrane protein is a melanin-concentrating hormone receptor (e.g., melanin concentrating hormone receptor 1 corresponding to Human protein RefSeq NP_005288, melanin concentrating hormone receptor 2 corresponding to Human protein RefSeq NP_0010352691NP_115892).

In embodiments, the membrane protein is a melanocortin receptor (e.g., melanocortin 1 receptor corresponding to Human protein RefSeq NP_002377, melanocortin 2 receptor corresponding to Human protein RefSeq NP_000520, melanocortin 3 receptor corresponding to Human protein RefSeq NP_063941, melanocortin 4 receptor corresponding to Human protein RefSeq NP_005903, melanocortin 5 receptor corresponding to Human protein RefSeq NP_005904).

In embodiments, the membrane protein is a melatonin receptor (e.g., melatonin receptor 1A corresponding to Human protein RefSeq NP_005949, melatonin receptor 1B corresponding to Human protein RefSeq NP_005950).

In embodiments, the membrane protein is a motilin receptor (e.g., motilin receptor corresponding to Human protein RefSeq NP_001498).

In embodiments, the membrane protein is a neuromedin U receptor (e.g., neuromedin U receptor 1 corresponding to Human protein RefSeq NP_006047, neuromedin U receptor 2 corresponding to Human protein RefSeq NP_064552).

In embodiments, the membrane protein is a neuropeptide FF/neuropeptide AF receptor (e.g., neuropeptide FF receptor 1 corresponding to Human protein RefSeq NP_071429, neuropeptide FF receptor 2 corresponding to Human protein RefSeq NP_444264, NP_001138228, or NP_004876).

In embodiments, the membrane protein is a neuropeptide S receptor (e.g., neuropeptide S receptor 1 corresponding to Human protein RefSeq NP_997055 or NP_997056).

In embodiments, the membrane protein is a neuropeptide W/neuropeptide B receptor (e.g., neuropeptides B and W receptor 1 corresponding to Human protein RefSeq NP_005276, neuropeptides B and W receptor 2 corresponding to Human protein RefSeq NP_005277).

In embodiments, the membrane protein is a neuropeptide Y receptor (e.g., neuropeptide Y receptor Y1 corresponding to Human protein RefSeq NP_000900, neuropeptide Y receptor Y2 corresponding to Human protein RefSeq NP_000901, neuropeptide Y receptor Y4 corresponding to Human protein RefSeq NP_005963, neuropeptide Y receptor Y5 corresponding to Human protein RefSeq NP_006165, neuropeptide Y receptor Y6 (pseudogene) corresponding to Human protein RefSeq).

In embodiments, the membrane protein is a neurotensin receptor (e.g., neurotensin receptor 1 corresponding to Human protein RefSeq NP_002522, neurotensin receptor 2 corresponding to Human protein RefSeq NP_036476).

In embodiments, the membrane protein is an opioid receptor (e.g., opioid receptor delta 1 corresponding to Human protein RefSeq NP_000902, opioid receptor kappa 1 corresponding to Human protein RefSeq NP_000903, opioid receptor mu 1 corresponding to Human protein RefSeq NP_000905, opioid related nociceptin receptor 1 corresponding to Human protein RefSeq NP_000904).

In embodiments, the membrane protein is an opsin receptor (e.g., opsin 1, long wave sensitive corresponding to Human protein RefSeq NP_064445, opsin 1, medium wave sensitive corresponding to Human protein RefSeq NP_000504, opsin 1, short wave sensitive corresponding to Human protein RefSeq NP_001699, rhodopsin corresponding to Human protein RefSeq NP_000530, opsin 3 corresponding to Human protein RefSeq NP_055137, opsin 4 corresponding to Human protein RefSeq NP_0010251861NP_150598, opsin 5 corresponding to Human protein RefSeq NP_859528).

In embodiments, the membrane protein is an orexin receptor (e.g., hypocretin receptor 1 corresponding to Human protein RefSeq NP_001516, hypocretin receptor 2 corresponding to Human protein RefSeq NP_001517).

In embodiments, the membrane protein is an oxoglutarate receptor (e.g., oxoglutarate receptor 1 corresponding to Human protein RefSeq NP_543008).

In embodiments, the membrane protein is a P2Y receptor (e.g., purinergic receptor P2Y1 corresponding to Human protein RefSeq NP_002554, purinergic receptor P2Y2 corresponding to Human protein RefSeq NP_002555, pyrimidinergic receptor P2Y4 corresponding to Human protein RefSeq NP_002556, pyrimidinergic receptor P2Y6 corresponding to Human protein RefSeq NP_001264133, purinergic receptor P2Y11 corresponding to Human protein RefSeq NP_002557, purinergic receptor P2Y12 corresponding to Human protein RefSeq NP_073625, purinergic receptor P2Y13 corresponding to Human protein RefSeq NP_795713, purinergic receptor P2Y14 corresponding to Human protein RefSeq NP_055694).

In embodiments, the membrane protein is a platelet-activating factor receptor (e.g., platelet activating factor receptor corresponding to Human protein RefSeq NP_000943).

In embodiments, the membrane protein is a prokineticin receptor (e.g., prokineticin receptor 1 corresponding to Human protein RefSeq NP_620414, prokineticin receptor 2 corresponding to Human protein RefSeq NP_658986).

In embodiments, the membrane protein is a prolactin-releasing peptide receptor (e.g., prolactin releasing hormone receptor corresponding to Human protein RefSeq NP_004239).

In embodiments, the membrane protein is a prostanoid receptor (e.g., prostaglandin D2 receptor corresponding to Human protein RefSeq NP_000944, prostaglandin D2 receptor 2 corresponding to Human protein RefSeq NP_004769, prostaglandin E receptor 1 corresponding to Human protein RefSeq NP_000946, prostaglandin E receptor 2 corresponding to Human protein RefSeq NP_000947, prostaglandin E receptor 3 corresponding to Human protein RefSeq NP_001119516, prostaglandin E receptor 4 corresponding to Human protein RefSeq NP_000949, prostaglandin F receptor corresponding to Human protein RefSeq NP_000950, prostaglandin 12 receptor corresponding to Human protein RefSeq NP_000951, thromboxane A2 receptor corresponding to Human protein RefSeq NP_001051).

In embodiments, the membrane protein is a proteinase-activated receptor (e.g., coagulation factor II thrombin receptor corresponding to Human protein RefSeq NP_001983, F2R like trypsin receptor 1 corresponding to Human protein RefSeq NP_005233, coagulation factor II thrombin receptor like 2 corresponding to Human protein RefSeq NP_004092, F2R like thrombin or trypsin receptor 3 corresponding to Human protein RefSeq NP_003941).

In embodiments, the membrane protein is a QRFP receptor (e.g., pyroglutamylated RFamide peptide receptor corresponding to Human protein RefSeq NP_937822).

In embodiments, the membrane protein is a relaxin family peptide receptor (e.g., relaxin/insulin like family peptide receptor 1 corresponding to Human protein RefSeq NP_067647, relaxin/insulin like family peptide receptor 2 corresponding to Human protein RefSeq NP_570718, relaxin/insulin like family peptide receptor 3 corresponding to Human protein RefSeq NP_057652, relaxin/insulin like family peptide receptor 4 corresponding to Human protein RefSeq NP_871001).

In embodiments, the membrane protein is a somatostatin receptor (e.g., somatostatin receptor 1 corresponding to Human protein RefSeq NP_001040, somatostatin receptor 2 corresponding to Human protein RefSeq NP_001041, somatostatin receptor 3 corresponding to Human protein RefSeq NP_001042, somatostatin receptor 4 corresponding to Human protein RefSeq NP_001043, somatostatin receptor 5 corresponding to Human protein RefSeq NP_001044).

In embodiments, the membrane protein is a succinate receptor (e.g., succinate receptor 1 corresponding to Human protein RefSeq NP_149039).

In embodiments, the membrane protein is a tachykinin receptor (e.g., tachykinin receptor 1 corresponding to Human protein RefSeq NP_001049, tachykinin receptor 2 corresponding to Human protein RefSeq NP_001048, tachykinin receptor 3 corresponding to Human protein RefSeq NP_001050).

In embodiments, the membrane protein is a thyrotropin-releasing hormone receptor (e.g., thyrotropin releasing hormone receptor corresponding to Human protein RefSeq NP_003292).

In embodiments, the membrane protein is a trace amine receptor (e.g., trace amine associated receptor 1 corresponding to Human protein RefSeq NP_612200).

In embodiments, the membrane protein is an urotensin receptor (e.g., urotensin 2 receptor corresponding to Human protein RefSeq NP_061822).

In embodiments, the membrane protein is a vasopressin receptor (e.g., arginine vasopressin receptor 1A corresponding to Human protein RefSeq NP_000697, arginine vasopressin receptor 1B corresponding to Human protein RefSeq NP_000698, arginine vasopressin receptor 2 corresponding to Human protein RefSeq NP_000045, oxytocin receptor corresponding to Human protein RefSeq NP_000907).

In embodiments, the membrane protein is or a combination of two or more membrane proteins described herein.

In embodiments, the membrane protein is an adenosine $A_{2A}$ receptor (e.g., adenosine $A_{2A}$ receptor corresponding to Human protein RefSeq NP_000666, NP_001265426, NP 001265427, NP_001265428, or NP_001265429.

In embodiments, the lipid membrane is a liposome or a micelle. In embodiments, the lipid membrane is a liposome. In embodiments, the lipid membrane is a micelle.

In embodiments, the molar ratio of the membrane protein to the synthetic phospholipid is from about 0.1:1 to about 1:1,000. In embodiments, the molar ratio of the membrane protein to the synthetic phospholipid is from about 0.1:1 to about 1:900. In embodiments, the molar ratio of the membrane protein to the synthetic phospholipid is from about 0.1:1 to about 1:800. In embodiments, the molar ratio of the membrane protein to the synthetic phospholipid is from about 0.1:1 to about 1:700. In embodiments, the molar ratio of the membrane protein to the synthetic phospholipid is from about 0.1:1 to about 1:600. In embodiments, the molar ratio of the membrane protein to the synthetic phospholipid is from about 0.1:1 to about 1:500.

In embodiments, the molar ratio of the membrane protein to the synthetic phospholipid is from about 0.1:1 to about 1:600. In embodiments, the molar ratio of the membrane protein to the synthetic phospholipid is about 0.1:550. In embodiments, the molar ratio of the membrane protein to the synthetic phospholipid is about 1:550. In embodiments, the molar ratio of the membrane protein to the synthetic phospholipid is about 1:540. In embodiments, the molar ratio of the membrane protein to the synthetic phospholipid is about 1:530. In embodiments, the molar ratio of the membrane protein to the synthetic phospholipid is about 1:520. In embodiments, the molar ratio of the membrane protein to the synthetic phospholipid is about 1:510. In embodiments, the molar ratio of the membrane protein to the synthetic phospholipid is about 1:500.

In an aspect is a liposome produced by the method as described herein.

In an aspect is a liposome including a membrane protein and a synthetic phospholipid (e.g., a synthetic pholid as described herein). In embodiments, the membrane protein is a G protein-coupled receptor. In embodiments, the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

In embodiments, the membrane protein is an adenosine $A_{2A}$ receptor. In embodiments, the synthetic phospholipid has the formula:

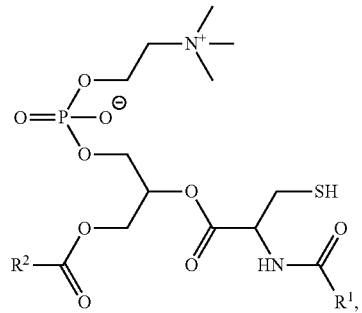

wherein $R^1$ and $R^2$ are as described herein, including embodiments.

In an aspect, is provided a method for reconstituting membrane proteins, the method including: solubilizing a membrane bound protein with a detergent, exchanging the detergent with a n-dodecyl-β-D-maltoside (DDM) thioester analog, forming a protein solubilized micelle, reacting the protein solubilized micelle with a lysophosphatidylcholine, and generating a stable synthetic liposome with an embedded membrane protein.

In one embodiment, the detergent is n-dodecyl-β-D-maltoside. In another embodiment, the DDM thioester analog is dodecyl maltose thioester. In another embodiment, the lyosphosphatidylcholine is cysteine-functionalized oleoyl lyosphosphatidylcholine. In another embodiment, the membrane protein is a G protein-coupled receptor (GPCR). In another embodiment, the G protein-coupled receptor (GPCR) is Adenosine $A_{2A}$ Receptor ($A_{2A}$R).

In embodiments, the maltoside surfactant is

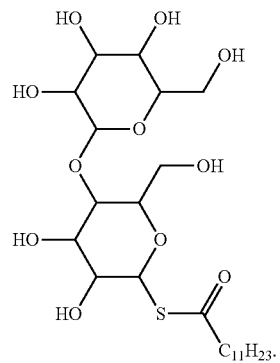

In embodiments, the maltoside surfactant is

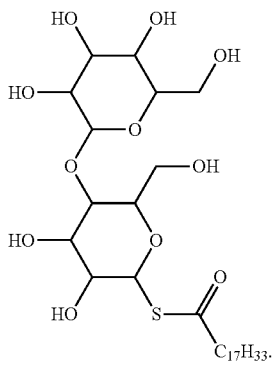

In embodiments, the maltoside surfactant is

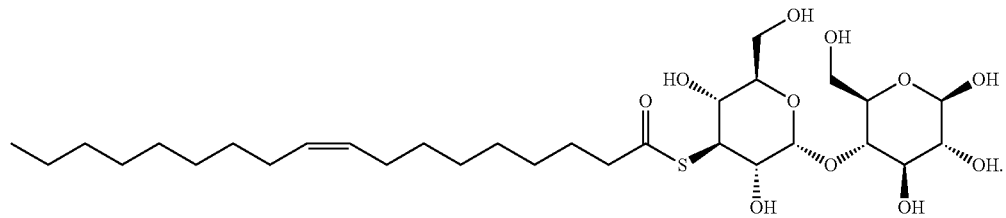 [SMILES: CCCCCCCC/C=C\CCCCCCCC(=O)S[C@@H]1[C@@H](O)[C@@H](O[C@H]2[C@H](O)[C@@H](O)[C@H](O)O[C@@H]2CO)O[C@H](CO)[C@H]1O]

In embodiments, the maltoside surfactant is

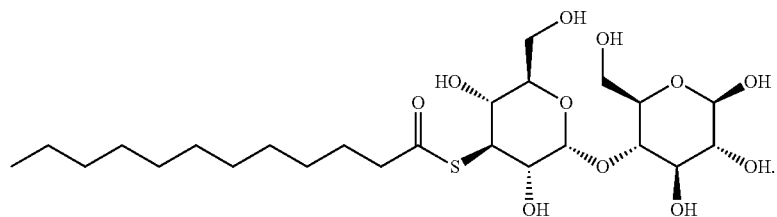 [SMILES: CCCCCCCCCCCC(=O)S[C@@H]1[C@@H](O)[C@@H](O[C@H]2[C@H](O)[C@@H](O)[C@H](O)O[C@@H]2CO)O[C@H](CO)[C@H]1O]

In embodiments, the phosphatidylcholine compound is

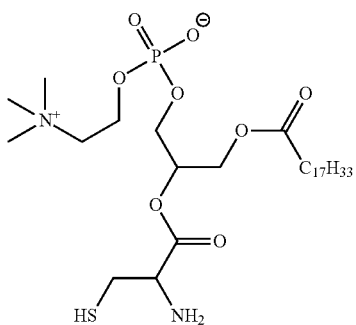

or

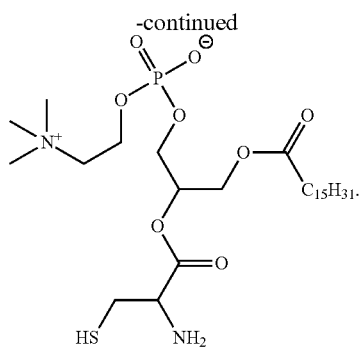

In an aspect is provided a composition comprising a lipid membrane including a membrane protein and a synthetic phospholipid (e.g., a synthetic pholid as described herein). In embodiments, the synthetic phospholipid has the formula:

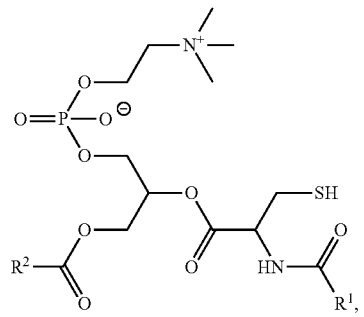

wherein $R^1$ and $R^2$ are independently substituted or unsubstituted alkyl, as described herein, including the embodiments above. In embodiments the lipid membrane is a synthetic lipid membrane.

In another aspect, is provided a composition including a stable synthetic proteoliposome containing a membrane-associated protein and one or more phospholipids. In one embodiment, the protein is a G protein-coupled receptor (GPCR).

In embodiments, the synthetic phospholipid is:

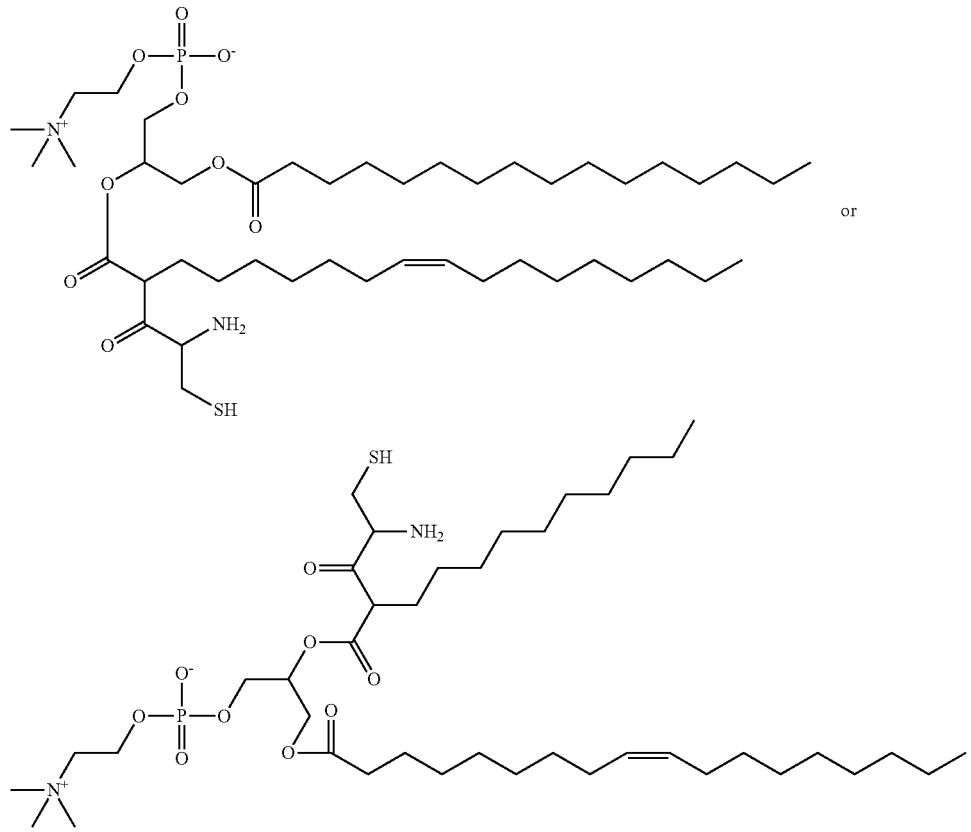

or

In another aspect is provided an aqueous solution including a membrane protein and a reactive surfactant which includes a reactive thioester moiety. In embodiments, the aqueous solution further includes a non-reactive surfactant (e.g., a nonionic alkyl glucoside). In embodiments, the non-reactive surfactant is n-dodecyl-β-D-maltoside. In embodiments, the membrane protein is a G protein-coupled receptor. In embodiments, the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof. In embodiments, the membrane protein is an adenosine $A_{2A}$ receptor. In embodiments, the reactive surfactant including a reactive thioester moiety is a maltoside surfactant as described herein.

Embodiments contemplated herein include the following.

Embodiment P1

A method for reconstituting membrane proteins, said method comprising: solubilizing a membrane bound protein with a detergent; exchanging the detergent with a n-dodecyl-β-D-maltoside (DDM) thioester analog; forming a protein solubilized micelle; reacting said protein solubilized micelle with a lysophosphatidylcholine; and generating a stable synthetic liposome with an embedded membrane protein.

Embodiment P2

The method of embodiment P1, wherein the detergent is n-dodecyl-β-D-maltoside.

Embodiment P3

The method of embodiment P1, wherein the DDM thioester analog is dodecyl maltose thioester.

Embodiment P4

The method of embodiment P1, wherein the lyosphosphatidylcholine is cysteine-functionalized oleoyl lyosphosphatidylcholine.

Embodiment P5

The method of embodiment P1, wherein the membrane protein is a G protein-coupled receptor (GPCR).

Embodiment P6

The method of embodiment P5, wherein the G protein-coupled receptor (GPCR) is Adenosine A2A Receptor (A2AR).

Embodiment P7

A composition comprising a stable synthetic proteoliposome comprising a membrane-associated protein and one or more phospholipids.

Embodiment P8

The composition of embodiment P7, wherein the protein is a G protein-coupled receptor (GPCR).

Embodiment 1

A method for forming a lipid membrane comprising a membrane protein, the method comprising: (i) solubilizing the membrane protein in a first surfactant to form a first solution; (ii) adding a reactive surfactant comprising a reactive thioester moiety to the first solution, thereby forming a second solution which comprises the reactive surfactant and the membrane protein; and (iii) adding a phosphatidylcholine compound to the second solution, thereby forming a synthetic phospholipid; wherein the synthetic phospholipid forms a lipid membrane comprising the membrane protein.

Embodiment 2

The method of embodiment 1, wherein the first surfactant is a nonionic alkyl glucoside.

Embodiment 3

The method of embodiment 1, wherein the first surfactant is n-dodecyl-β-D-maltoside.

Embodiment 4

The method of any one of embodiments 1 to 3, wherein (ii) comprises replacing the first surfactant with the reactive surfactant in forming the second solution.

Embodiment 5

A method for forming a lipid membrane comprising a membrane protein, the method comprising: (i) adding a reactive surfactant comprising a reactive thioester moiety to a first solution which comprises the membrane protein, thereby forming a second solution which comprises the reactive surfactant and the membrane protein; and (ii) adding a phosphatidylcholine compound to the second solution, thereby forming a synthetic phospholipid; wherein the synthetic phospholipid forms a lipid membrane comprising the membrane protein.

Embodiment 6

A method for forming a lipid membrane comprising a membrane protein, the method comprising adding a phosphatidylcholine compound to a solution which comprises a reactive surfactant and a membrane protein, thereby forming a synthetic phospholipid; wherein the synthetic phospholipid forms a lipid membrane comprising the membrane protein.

Embodiment 7

The method of any one of embodiments 1 to 6, wherein the synthetic phospholipid is formed by native chemical ligation.

Embodiment 8

The method of any one of embodiments 1 to 7, wherein the reactive surfactant comprising a reactive thioester moiety is a maltoside surfactant.

Embodiment 9

The method of embodiment 8, wherein the maltoside surfactant has the formula:

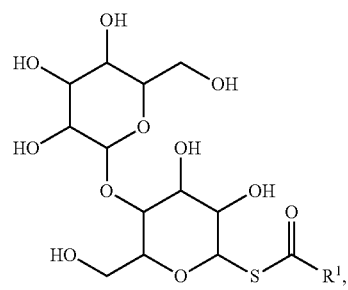

wherein $R^1$ is a substituted or unsubstituted alkyl.

Embodiment 10

The method of any one of embodiments 1 to 9, wherein the phosphatidylcholine compound is a lysophosphatidylcholine compound.

Embodiment 11

The method of any one of embodiments 1 to 9, wherein the phosphatidylcholine compound has the formula:

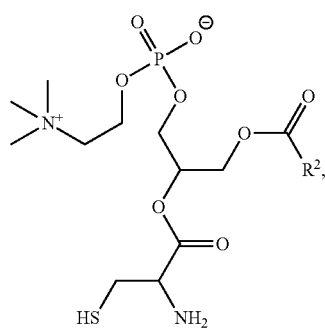

wherein $R^2$ is a substituted or unsubstituted alkyl.

Embodiment 12

The method of any one of embodiments 1 to 11, wherein the synthetic phospholipid has the formula:

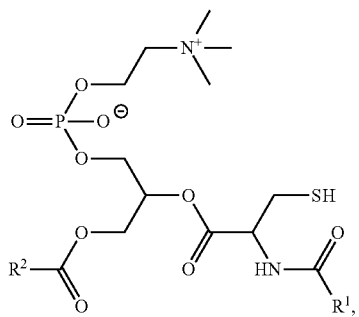

wherein $R^1$ is a substituted or unsubstituted alkyl.

Embodiment 13

The method of embodiment 9 or 12, wherein $R^1$ is a substituted or unsubstituted $C_4$-$C_{30}$ alkyl.

Embodiment 14

The method of embodiment 9 or 12, wherein $R^1$ is an unsubstituted $C_4$-$C_{20}$ alkyl.

Embodiment 15

The method of embodiment 9 or 12, wherein $R^1$ is an unsubstituted $C_6$-$C_{18}$ alkyl.

Embodiment 16

The method of embodiment 9 or 12, wherein $R^1$ is an unsubstituted $C_{10}$-$C_{20}$ alkyl.

Embodiment 17

The method of embodiment 9 or 12, wherein $R^1$ is an unsubstituted $C_{10}$-$C_{18}$ alkyl.

Embodiment 18

The method of embodiment 9 or 12, wherein $R^1$ is an unsubstituted $C_{12}$-$C_{16}$ alkyl.

Embodiment 19

The method of embodiment 9 or 12, wherein $R^1$ is an unsubstituted $C_6$-$C_{18}$ alkenyl.

Embodiment 20

The method of embodiment 9 or 12, wherein $R^1$ is an unsubstituted $C_{10}$-$C_{14}$ alkyl.

Embodiment 21

The method of embodiment 9 or 12, wherein $R^1$ is an unsubstituted $C_{16}$-$C_{20}$ alkyl.

Embodiment 22

The method of embodiment 9 or 12, wherein $R^1$ is a $C_6$ alkyl; a $C_7$ alkyl; a $C_8$ alkyl; a $C_9$ alkyl; a $C_{10}$ alkyl; a $C_{11}$ alkyl; a $C_{12}$ alkyl; a $C_{13}$ alkyl; a $C_{14}$ alkyl; a $C_{15}$ alkyl; a $C_{16}$ alkyl; a $C_{17}$ alkyl; a $C_{18}$ alkyl; a $C_{19}$ alkyl; or a $C_{20}$ alkyl.

Embodiment 23

The method of embodiment 11 or 12, wherein $R^2$ is a substituted or unsubstituted $C_4$-$C_{30}$ alkyl.

Embodiment 24

The method of embodiment 11 or 12, wherein $R^2$ is an unsubstituted $C_4$-$C_{20}$ alkyl.

Embodiment 25

The method of embodiment 11 or 12, wherein $R^2$ is an unsubstituted $C_6$-$C_{18}$ alkyl.

Embodiment 26

The method of embodiment 11 or 12, wherein $R^2$ is an unsubstituted $C_{10}$-$C_{20}$ alkyl.

Embodiment 27

The method of embodiment 11 or 12, wherein $R^2$ is an unsubstituted $C_{10}$-$C_{18}$ alkyl.

Embodiment 28

The method of embodiment 11 or 12, wherein $R^2$ is an unsubstituted $C_{12}$-$C_{16}$ alkyl.

Embodiment 29

The method of embodiment 11 or 12, wherein $R^2$ is an unsubstituted $C_6$-$C_{18}$ alkenyl.

Embodiment 30

The method of embodiment 11 or 12, wherein $R^2$ is an unsubstituted $C_{10}$-$C_{14}$ alkyl.

Embodiment 31

The method of embodiment 11 or 12, wherein $R^2$ is an unsubstituted $C_{16}$-$C_{20}$ alkyl.

Embodiment 32

The method of embodiment 11 or 12, wherein $R^2$ is a $C_6$ alkyl; a $C_7$ alkyl; a $C_8$ alkyl; a $C_9$ alkyl; a $C_{10}$ alkyl; a $C_{11}$ alkyl; a $C_{12}$ alkyl; a $C_{13}$ alkyl; a $C_{14}$ alkyl; a $C_{15}$ alkyl; a $C_{16}$ alkyl; a $C_{17}$ alkyl; a $C_{18}$ alkyl; a $C_{19}$ alkyl; or a $C_{20}$ alkyl.

Embodiment 33

The method of any one of embodiments 1 to 32, wherein the membrane protein is a G protein-coupled receptor.

Embodiment 34

The method of any one of embodiments 1 to 32, wherein the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

Embodiment 35

The method of any one of embodiments 1 to 32, wherein the membrane protein is an adenosine $A_{2A}$ receptor.

Embodiment 36

The method of any one of embodiments 1 to 35, wherein the lipid membrane is a liposome.

Embodiment 37

The method of any one of embodiments 1 to 36, wherein the molar ratio of the membrane protein to the synthetic phospholipid is from about 0.1:1 to about 1:1,000.

Embodiment 38

The method of any one of embodiments 1 to 36, wherein the molar ratio of the membrane protein to the synthetic phospholipid is from about 0.1:1 to about 1:600.

Embodiment 39

The method of any one of embodiments 1 to 36, wherein the molar ratio of the membrane protein to the synthetic phospholipid is about 1:530.

Embodiment 40

A liposome produced by the method of any one of embodiments 1 to 39.

Embodiment 41

A liposome comprising a membrane protein and a synthetic phospholipid.

Embodiment 42

The liposome of embodiment 41, wherein the membrane protein is a G protein-coupled receptor.

Embodiment 43

The liposome of embodiment 41, wherein the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

Embodiment 44

The liposome of embodiment 41, wherein the membrane protein is an adenosine $A_{2A}$ receptor.

Embodiment 45

The liposome of any one of embodiments 41 to 44, wherein the synthetic phospholipid has the formula:

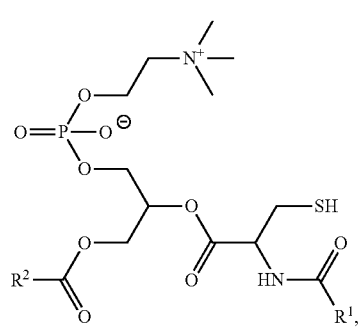

wherein $R^1$ and $R^2$ are independently substituted or unsubstituted alkyl.

Embodiment 46

The liposome of embodiment 45, wherein $R^1$ and $R^2$ are independently a substituted or unsubstituted $C_4$-$C_{30}$ alkyl.

Embodiment 47

The liposome of embodiment 45, wherein $R^1$ and $R^2$ are independently an unsubstituted $C_4$-$C_{20}$ alkyl.

Embodiment 48

The liposome of embodiment 45, wherein $R^1$ and $R^2$ are independently an unsubstituted $C_6$-$C_{18}$ alkyl.

Embodiment 49

The liposome of embodiment 45, wherein $R^1$ and $R^2$ are independently an unsubstituted $C_{10}$-$C_{20}$ alkyl.

Embodiment 50

The liposome of embodiment 45, wherein $R^1$ and $R^2$ are independently an unsubstituted $C_{10}$-$C_{18}$ alkyl.

Embodiment 51

The liposome of embodiment 45, wherein $R^1$ and $R^2$ are independently an unsubstituted $C_{12}$-$C_{16}$ alkyl.

Embodiment 52

The liposome of embodiment 45, wherein $R^1$ and $R^2$ are independently an unsubstituted $C_6$-$C_{18}$ alkenyl.

Embodiment 53

The liposome of embodiment 45, wherein $R^1$ and $R^2$ are independently an unsubstituted $C_{10}$-$C_{14}$ alkyl.

Embodiment 54

The liposome of embodiment 45, wherein $R^1$ and $R^2$ are independently an unsubstituted $C_{16}$-$C_{20}$ alkyl.

Embodiment 55

The liposome of embodiment 45, wherein $R^1$ and $R^2$ are independently a $C_6$ alkyl; a $C_7$ alkyl; a $C_8$ alkyl; a $C_9$ alkyl; a $C_{10}$ alkyl; a $C_{11}$ alkyl; a $C_{12}$ alkyl; a $C_{13}$ alkyl; a $C_{14}$ alkyl; a $C_{15}$ alkyl; a $C_{16}$ alkyl; a $C_{17}$ alkyl; a $C_{18}$ alkyl; a $C_{19}$ alkyl; or a $C_{20}$ alkyl.

Embodiment 56

An aqueous solution comprising a membrane protein and a reactive surfactant which comprises a reactive thioester moiety.

Embodiment 57

The solution of embodiment 56, further comprising a non-reactive surfactant.

Embodiment 58

The solution of embodiment 57, wherein the non-reactive surfactant is a nonionic alkyl glucoside.

Embodiment 59

The solution of embodiment 57, wherein the non-reactive surfactant is n-dodecyl-β-D-maltoside.

Embodiment 60

The solution of any one of embodiments 56 to 59, wherein the membrane protein is a G protein-coupled receptor.

Embodiment 61

The solution of any one of embodiments 56 to 59, wherein the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

Embodiment 62

The solution of any one of embodiments 56 to 59, wherein the membrane protein is an adenosine $A_{2A}$ receptor.

Embodiment 63

The solution of any one of embodiments 56 to 62, wherein the reactive surfactant comprising a reactive thioester moiety is a maltoside surfactant.

Embodiment 64

The solution of embodiment 63, wherein the maltoside surfactant has the formula:

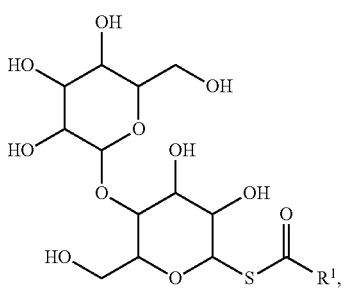

wherein $R^1$ is a substituted or unsubstituted alkyl.

Embodiment 65

The solution of embodiment 64, wherein $R^1$ is a substituted or unsubstituted $C_4$-$C_{30}$ alkyl.

Embodiment 66

The solution of embodiment 64, wherein $R^1$ is an unsubstituted $C_4$-$C_{20}$ alkyl.

Embodiment 67

The solution of embodiment 64, wherein $R^1$ is an unsubstituted $C_6$-$C_{18}$ alkyl.

Embodiment 68

The solution of embodiment 64, wherein $R^1$ is an unsubstituted $C_{10}$-$C_{20}$ alkyl.

Embodiment 69

The solution of embodiment 64, wherein $R^1$ is an unsubstituted $C_{10}$-$C_{18}$ alkyl.

Embodiment 70

The solution of embodiment 64, wherein $R^1$ is an unsubstituted $C_{12}$-$C_{16}$ alkyl.

Embodiment 71

The solution of embodiment 64, wherein $R^1$ is an unsubstituted $C_6$-$C_{18}$ alkenyl.

Embodiment 72

The solution of embodiment 64, wherein $R^1$ is an unsubstituted $C_{10}$-$C_{14}$ alkyl.

Embodiment 73

The solution of embodiment 64, wherein $R^1$ is an unsubstituted $C_{16}$-$C_{20}$ alkyl.

Embodiment 74

The solution of embodiment 64, wherein $R^1$ is a $C_6$ alkyl; a $C_7$ alkyl; a $C_8$ alkyl; a $C_9$ alkyl; a $C_{10}$ alkyl; a $C_{11}$ alkyl; a $C_{12}$ alkyl; a $C_{13}$ alkyl; a $C_{14}$ alkyl; a $C_{15}$ alkyl; a $C_{16}$ alkyl; a $C_{17}$ alkyl; a $C_{18}$ alkyl; a $C_{19}$ alkyl; or a $C_{20}$ alkyl.

Embodiment 75

The solution of any one of embodiments 56 to 74, further comprising a phosphatidylcholine compound.

Embodiment 76

The solution of embodiment 75, wherein the phosphatidylcholine compound has the formula:

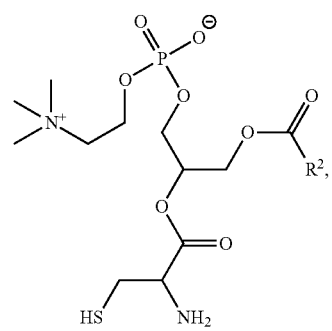

wherein $R^2$ is a substituted or unsubstituted alkyl.

Embodiment 77

The solution of embodiment 76, wherein $R^2$ is a substituted or unsubstituted $C_4$-$C_{30}$ alkyl.

Embodiment 78

The solution of embodiment 76, wherein $R^2$ is an unsubstituted $C_4$-$C_{20}$ alkyl.

Embodiment 79

The solution of embodiment 76, wherein $R^2$ is an unsubstituted $C_6$-$C_{18}$ alkyl.

Embodiment 80

The solution of embodiment 76, wherein $R^2$ is an unsubstituted $C_{10}$-$C_{20}$ alkyl.

Embodiment 81

The solution of embodiment 76, wherein $R^2$ is an unsubstituted $C_{10}$-$C_{18}$ alkyl.

Embodiment 82

The solution of embodiment 76, wherein $R^2$ is an unsubstituted $C_{12}$-$C_{16}$ alkyl.

Embodiment 83

The solution of embodiment 76, wherein $R^2$ is an unsubstituted $C_6$-$C_{18}$ alkenyl.

Embodiment 84

The solution of embodiment 76, wherein $R^2$ is an unsubstituted $C_{10}$-$C_{14}$ alkyl.

Embodiment 85

The solution of embodiment 76, wherein $R^2$ is an unsubstituted $C_{16}$-$C_{20}$ alkyl.

Embodiment 86

The solution of embodiment 76, wherein $R^2$ is a $C_6$ alkyl; a $C_7$ alkyl; a $C_8$ alkyl; a $C_9$ alkyl; a $C_{10}$ alkyl; a $C_{11}$ alkyl; a $C_{12}$ alkyl; a $C_{13}$ alkyl; a $C_{14}$ alkyl; a $C_{15}$ alkyl; a $C_{16}$ alkyl; a $C_{17}$ alkyl; a $C_{18}$ alkyl; a $C_{19}$ alkyl; or a $C_{20}$ alkyl.

EXAMPLES

Example 1—In Situ Reconstitution of the Adenosine A2A Receptor in Spontaneously Formed Synthetic Liposomes Cell transmembrane receptors play a key role in the detection of environmental stimuli and control of intracellular communication. G protein-coupled receptors (GPCRs) constitute the largest transmembrane protein family involved in cell signaling. However, current methods for their functional reconstitution in biomimetic membranes remain both challenging and limited in scope. Herein, we describe the spontaneous reconstitution of adenosine $A_{2A}$ receptor ($A_{2A}R$) during the de novo formation of synthetic liposomes via native chemical ligation (NCL). The approach takes advantage of a non-enzymatic and chemoselective method to rapidly generate $A_{2A}R$ embedded phospholiposomes from receptor solubilized in n-dodecyl-β-D-maltoside (DDM) analogs. In situ lipid synthesis for protein reconstitution technology (INSYRT) proceeds in the absence of dialysis and/or detergent absorbents, and $A_{2A}R$ assimilation into synthetic liposomes can be visualized by microscopy and probed by radio-ligand binding.

G protein-coupled receptors (GPCRs) represent the largest class of transmembrane receptors found in eukaryotes.[1,2] This superfamily functions in signal transduction involved in numerous physiological processes including sensory phenomena and metabolism.[3] GPCRs recognize a wide variety of structurally diverse ligands (agonists and antagonists) such as hormones, peptides, lipids, nucleotides and neurotransmitters.[4] Besides G proteins, GPCRs may couple with multiple intracellular partners (e.g. arrestins) and undergo endocytosis.[5] Thus, the precise conditions under which GPCR-mediated signaling is processed can be difficult to characterize, particularly with respect to signaling bias or allostery. Reductionist strategies are commonly employed to decouple state or structural determinants that elicit a specific ligand induced signal-response. One such strategy is to study the receptor dynamics in monodisperse detergent micelles. Unfortunately, most membrane proteins, including GPCRs, are unstable in detergent bilayers and display altered (compromised) pharmacological and functional properties.[6] To circumvent these detergent effects, membrane proteins may be reconstituted in stable-biomimetic membranes such as vesicles, reconstituted high-density lipoprotein (HDL) (nanodiscs), bicelles or with amphipoles.[7,8] While these approaches are powerful and have uncovered fundamental properties of GPCR function, they are quite methodologically cumbersome, requiring chromatography steps to remove detergents. Moreover, structural features normally found in cell membranes such as curvature and polarity are mostly absent. Interpretations based on these methods may overlook the degree to which GPCR signal scaffolding depends on membrane curvature and composition. In this regard, a rapid and robust reconstitution methodology that better mimics the native chemical environment of a whole-cell embedded GPCR would be highly useful.

Recently, Applicants demonstrated the feasibility of using non-membrane forming surfactants, such as lysophospholipid analogs and fatty acyl thioesters, as reactive precursors to generate liposomes and subsequently reconstitute membrane proteins during de novo phospholipid synthesis.[9] However, the lysophospholipids used for protein solubilization are modest detergents for the purification and isolation of membrane proteins.[10] Lysophospholipid critical micelle concentrations (cmc's) range between 4 to 8 µM, which are relatively low, resulting in a greater propensity to form micelles before the surfactant can fully solubilize a membrane protein.[11] Additional challenges exist with the lysophospholipid head group. When using ionic or zwitterionic detergents, there is an increased possibility of denaturing a protein of interest, and less success of renaturing and restoring the protein's native function.[12] These drawbacks limit the applicability of previous methodology in reconstituting more challenging transmembrane proteins like GPCRs.

With the goal of developing an efficient in situ reconstitution compatible with GPCRs, Applicants describe and exemplify herein the native chemical ligation (NCL)-promoted incorporation of the adenosine $A_{2A}$ receptor ($A_{2A}R$), a subclass of GPCRs, in synthetic liposomes using novel n-dodecyl-β-D-maltoside (DDM) thioester analogs (FIGS. 1A-1B, FIG. 5). In situ lipid synthesis for protein reconstitution technology (INSYRT) provides a rapid and selective method for creating GPCR-containing proteoliposomes.

Figure 6:
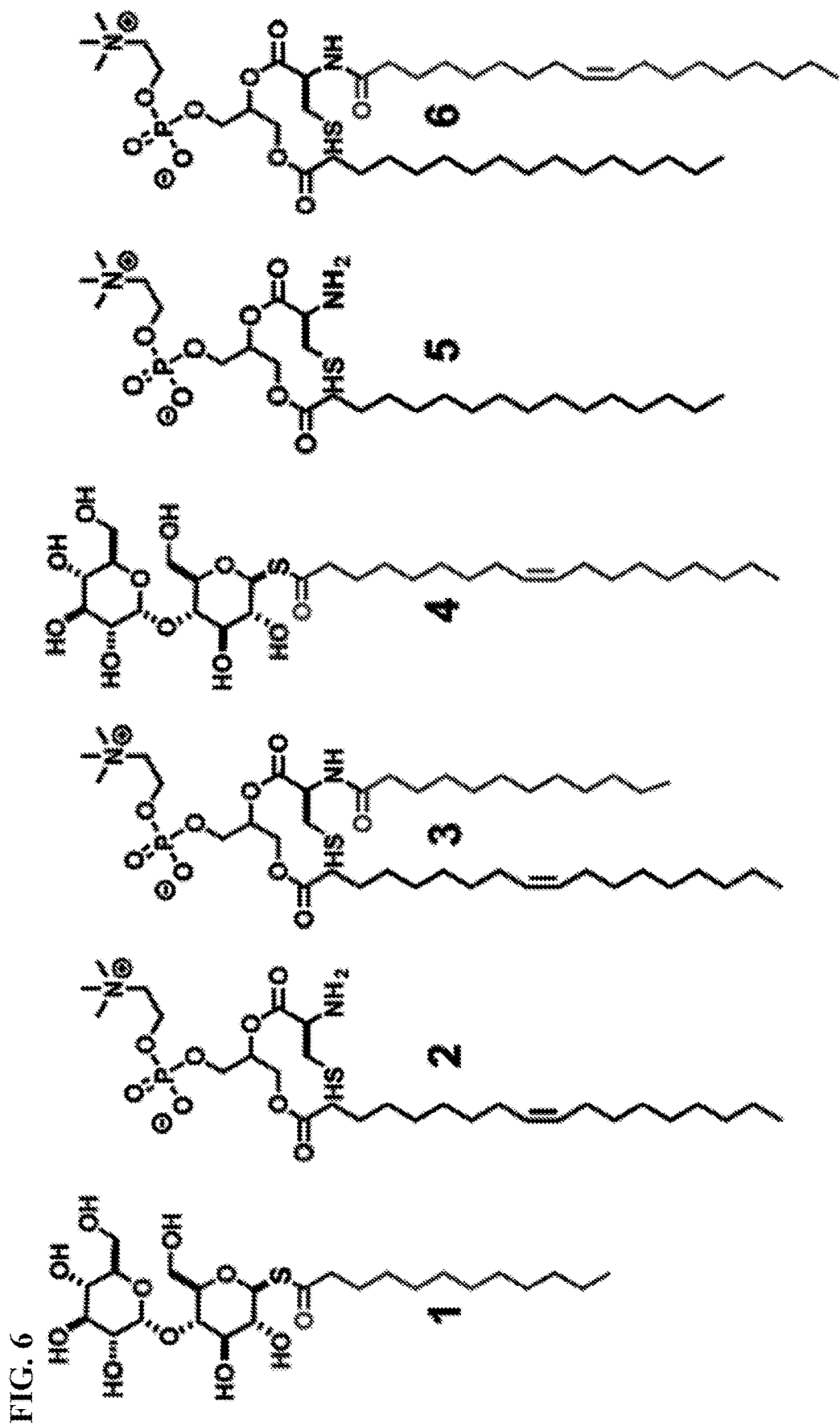
FIG. 6. Chemical structures of compounds disclosed herein.

The standard extraction and solubilization of GPCRs involves the use of nonionic alkyl glucoside detergents, specifically DDM, followed by subsequent detergent depletion in the presence of 1-palmitoyl-2-oleoyl-sn-glycero-3-phosphocholine (POPC) (FIG. 5).[12,13] The maltoside surfactant coaxes the micellar-solubilized receptors into fusing with a stable lipid-system (e.g. liposomal membrane, HDL nanodisc, planar membrane). DDM forms oblate ellipsoid micelles,[14] which stabilize GPCRs by better encapsulating the bilayer environment, while their large micellar size helps in preventing protein-protein aggregation.[15,16] In addition, DDM has a moderate cmc of 170 µM,[17] permitting higher working concentrations than other conventional detergents (e.g. octyl-β-glucopyranoside (OGP) and N,N-dimethyldodecylamine-N-oxide (DDAO)).[18,19] Recognizing the optimal characteristics of DDM, Applicants designed an analog of DDM, the dodecanoyl maltose thioester 1 (FIG. 1B, FIG. 6 and FIG. 7), which can be utilized as both a protein-solubilizing surfactant and a reactive precursor in our NCL reconstitution method (FIG. 5).

INSYRT was initially carried out by exchange of DDM for the dodecyl maltose thioester 1 to form micellar-solubilized $A_{2A}R$ (FIG. 1A). The protein-solubilized micelles were then reacted with an equal molar ratio of the cysteine-functionalized oleoyl lysophosphatidylcholine 2 (FIG. 1B, FIG. 6 and FIG. 8) through native chemical ligation (NCL) (FIG. 9 and FIG. 10).[9,20] The reaction afforded phospholipid 3 (FIG. 1B, FIG. 6 and FIG. 9), a synthetic analog of native 1-oleoyl-2-palmitoyl-sn-glycero-3-phosphocholine (OPPC). Formation of phospholipid 3 subsequently lead to stable liposome generation and concurrent embedding of $A_{2A}R$ in the membrane. The approach benefits from employing non-enzymatic and chemoselective coupling partners (maltose thioester 1 and lysophospholipid 2) that rapidly react while retaining specificity in buffers, with the only byproduct being the eliminated thiomaltose. The de novo formation of phospholipid also opens up the prospect of rapidly reconstituting the $A_{2A}R$ receptor in liposomes with minimum workflow. The in situ NCL reaction is responsible for the concerted depletion of lysophospholipid and the accumulation of phospholipid in approximately 20 minutes without the need for additional post-workups or purifications. The reaction was completed as discerned by liquid chromatography (LC), mass spectrometry (MS), and evaporative light scattering detection (ELSD) (FIG. 2, FIGS. 11A-11F). Applicants also observed that the final molar ratio comprising the resulting $A_{2A}R/3$ proteoliposomes is approximately 1:530 ($A_{2A}R$: Phospholipid 3). Alternatively, analogous INSYRT experiments using the water-soluble precursors oleoyl maltose thioester 4 and cysteine-functionalized palmitoyl lysophosphatidylcholine 5 also allow efficient formation of phospholipid 6 and subsequent incorporation of $A_{2A}R$ (FIG. 1B, FIG. 5 to FIGS. 11A-11F) showing additional versatility for this method.

Figures 3A, 3B, 3C, 3D:
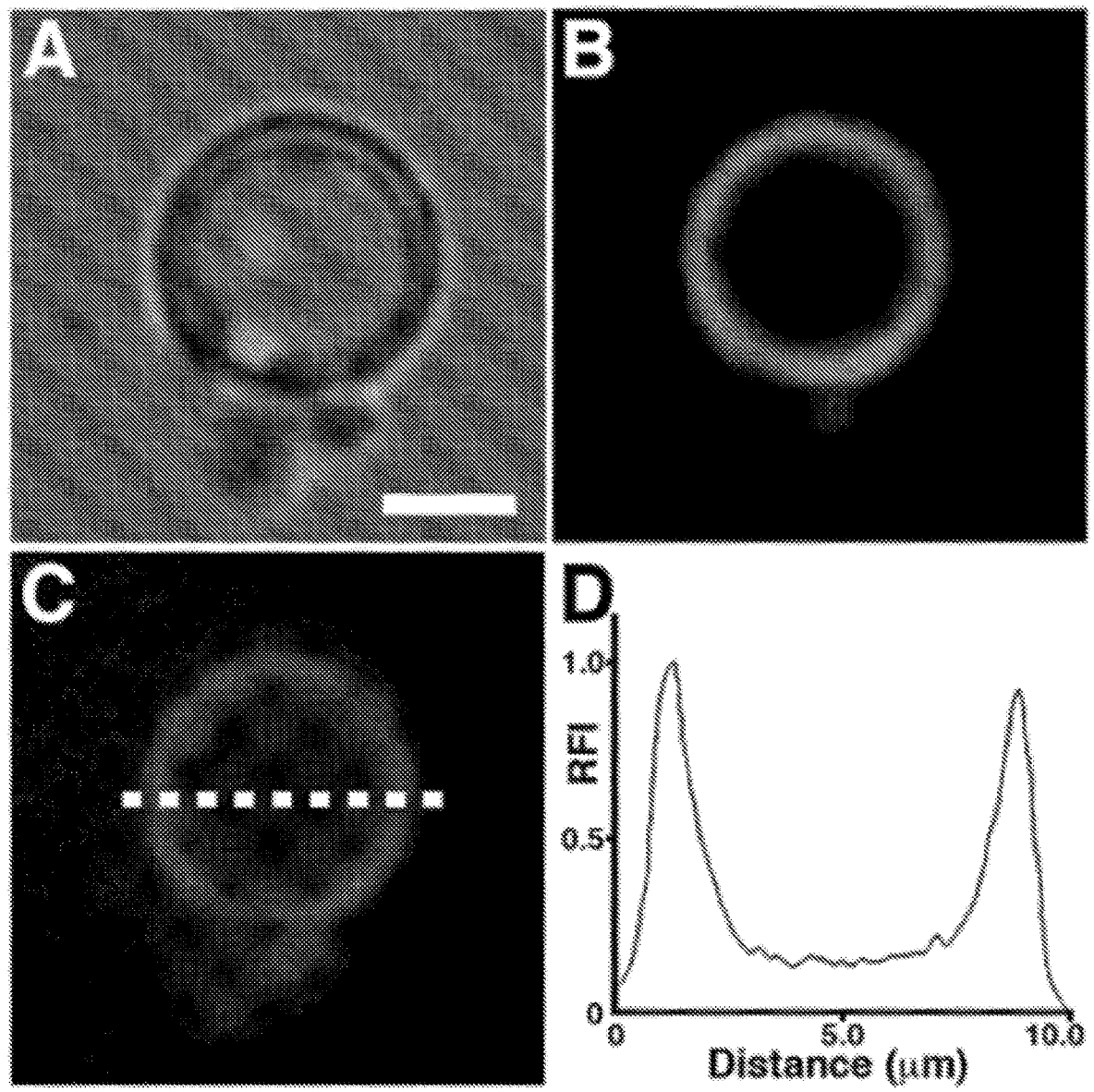
FIGS. 3A-3D. Spinning-disk confocal microscopy of spontaneously reconstituted $A_{2A}R/3$ proteoliposomes.

Applicants next turned to spinning-disk confocal microscopy to visualize liposome morphology and receptor staining using a combination of phase-contrast (FIG. 3A) and fluorescence imaging (FIGS. 3B-3D, FIG. 12). Fluorescence microscopy was initially carried out with the inclusion of the lipid-staining dye Texas Red® DHPE, at a final concentration of 0.5 mol % (FIG. 3B). To confirm $A_{2A}R$ was successfully reconstituted in liposomes we labeled purified $A_{2A}R$ with Alexa Fluor® 488 N-hydroxysuccinimidyl ester (AF-488 NHS) followed by overnight dialysis and three buffer exchanges to stringently remove any unreacted NHS dye. Immediately prior to the reaction, 2.8 µM of fluorophore-modified $A_{2A}R$ was exchanged into 20 mM HEPES buffer, pH 7.4 containing 100 mM NaCl, 20 mM DTT and 1.5 mM dodecanoyl maltose thioester 1. With the addition of lysophospholipid 2, at a final concentration of 1.5 mM, $A_{2A}R/3$ proteoliposome formation was initiated as indicated by the disappearance of both maltose thioester 1 and lysolipid 2, and the formation of phospholipid 3. Applicants observed the co-localization of the fluorescently (AF-488) labeled $A_{2A}R$ with Texas Red® DHPE, thus indicating that $A_{2A}R$ is primarily localized to the synthetic phospholipid membranes of the liposomes (FIG. 3C).

Figure 4A:
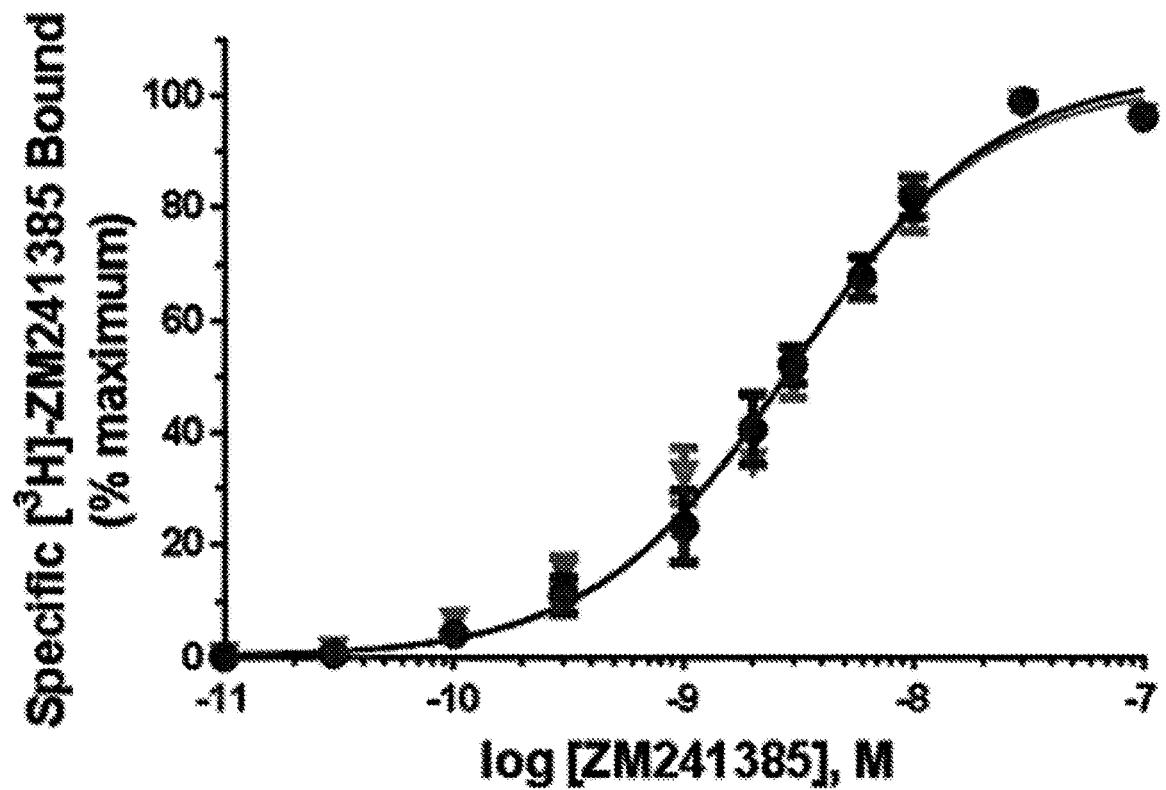
FIGS. 4A-4B. Radiolabeled orthosteric ligand equilibrium experiments with reconstituted $A_{2A}R$.
Figure 4B:
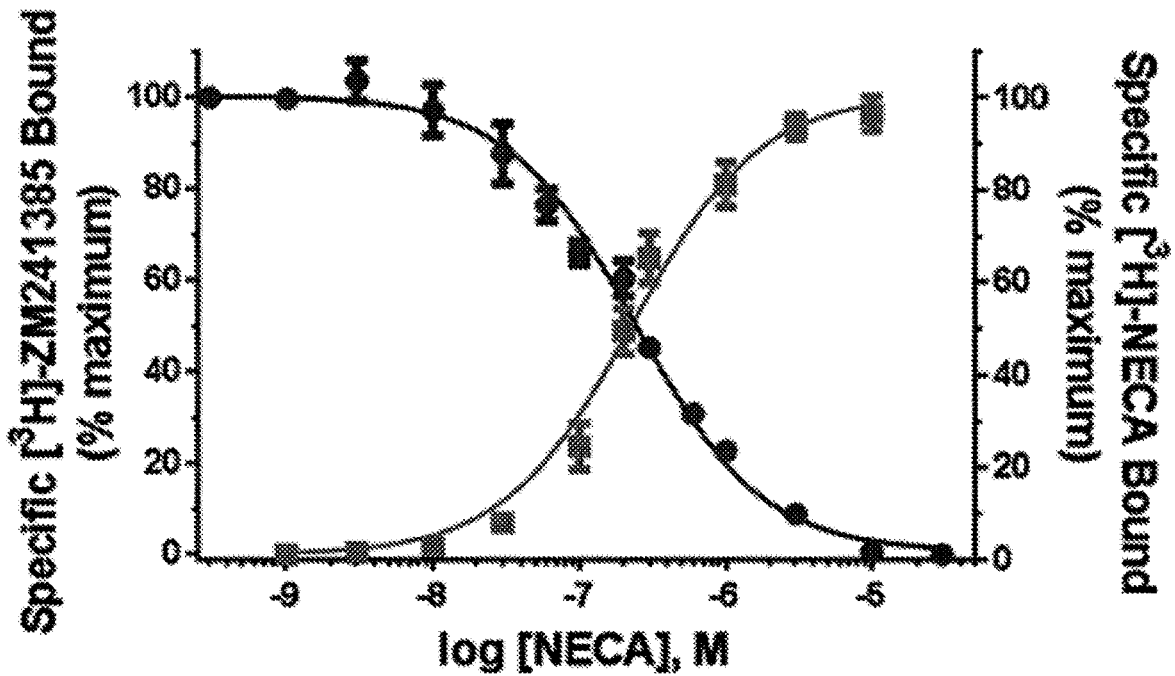

Having shown that $A_{2A}R$ could be spontaneously reconstituted in liposomes, Applicants next sought to determine whether the receptor remains capable of interacting with known orthosteric ligands (FIGS. 4A-4B). This aspect is important when considering that GPCRs in detergent micelles show reduced stability or shifted functional properties and interactions with ligands.[6] Rapid GPCR reconstitution methodologies like the HDL- or nanodisc-based approaches allow for increased stability over detergent solubilized receptors and demonstrate equilibrium affinities for ligands comparable to that as observed in membranes.[21] Currently, HDL-GPCR embedded bi-layers are the prevailing approach for reconstituting GPCRs.[22] Therefore, Applicants compared the activity of $A_{2A}R$ reconstituted in synthetic membranes using both in situ NCL-based liposomes and the HDL methodology. Purified $A_{2A}R$ was efficiently reconstituted during the NCL reaction as described earlier, while the HDL reconstitution method was adapted from a previous β2 adrenergic receptor (β2AR) HDL incorporation protocol.[8] Applicants initially performed radio-ligand binding assays with [$^3$H]-ZM241385, an antagonist of $A_{2A}R$. Saturation experiments carried out with in situ reconstituted $A_{2A}R$ demonstrated a dissociation constant (Kd) of 3.0±0.3 nM (n=3; ±SEM of multiple independent experimental preparations; 2 h incubations at 25° C.) (FIG. 4A), which is in close agreement with dissociation constants observed with $A_{2A}R$ reconstituted in HDL nanodiscs (2.9±0.3 nM (n=4; ±SEM of independent experiments)) (FIG. 4A) and in isolated cellular membranes.[23] Furthermore, Applicants found that the in situ approach yielded a reconstitution efficiency of approximately 30%. Applicants next performed [$^3$H]-ZM241385/5'-(N-ethylcarboxamido)adenosine (NECA) competition and found the inhibitory constant (Ki) to be 150.0±8.7 nM (n=3; ±SEM of multiple independent experimental preparations; 2 h incubations at 25° C.) for the full agonist NECA against in situ reconstituted $A_{2A}R$ (FIG. 4B). Applicants also found a Kd of 227.0±25.0 nM (n=4; ±SEM of independent experiments) for specific [$^3$H]-NECA binding in HDLs (FIG. 4B), which is in close approximation with literature values.[24]

Radiolabeling experiments showed that the reconstitution of $A_{2A}R$ during INSYRT is similar relative to the HDL reconstitution method based on their respective observed Kd and Ki. Therefore, the advantages of these systems would be application-specific, as the in situ NCL reaction provides compartmentalization compared to the accessibility of the HDL reconstitution (i.e. both sides of the receptor are available for binding). However, for studies of protein-protein or protein-lipid interactions, INSYRT would be desirable because it provides a better mimic to study lateral diffusion and kinetics. For instance, Schuler et. al. have recently found that liposomes display lateral thermal expansion coefficients two-fold higher than in their respective HDL counterparts.[25] These differences are attributed to the HDL boundary lipids being unable to adopt the same phase changes as the lipids in the center of the particle.

Experimental

Commercially available 1-oleoyl-2-hydroxy-sn-glycero-3-phosphocholine, 1-palmitoyl-2-hydroxy-sn-glycero-3-phosphocholine and 1-palmitoyl-2-oleoyl-sn-glycero-3-phosphocholine (POPC) were used as obtained from Avanti® Polar Lipids. D-(+)-maltose monohydrate, hydrobromic acid (HBr) solution [33% in glacial acetic acid (AcOH)], potassium ethylxanthate, sodium, dodecanoic acid (DDA), oleic acid (OA), O-(7-azabenzotriazol-1-yl)-1,1,3,3-tetramethyl-uronium hexafluorophosphate (HATU), N,N-diisopropylethylamine (DIEA), N-Boc-L-Cys(Trt)-OH, N,N'-diisopropylcarbo-diimide (DIC), 4-dimethylaminopyridine (DMAP), trifluoroacetic acid (TFA), triethylsilane (TES), sodium phosphate monobasic monohydrate ($NaH_2PO_4 \cdot H_2O$), dithiothreitol (DTT), n-dodecyl-β3-D-maltoside (DDM), 4-(-2-[7-amino-2-{2-furyl} {1,2,4}triazolo{2,3-a} {1,3,5}triazin-5-yl-amino]ethyl)phenol (ZM241385) and 5'-(N-ethylcarboxamido) (NECA) were obtained from Sigma-Aldrich. Texas Red® 1,2-dihexa-decanoyl-sn-glycero-3-phosphoethanolamine, triethylammonium salt (Texas Red® DHPE) and Alexa Fluor® 488 N-hydroxy-succinimide ester (Alexa Fluor® 488 NHS ester) were obtained from Life Technologies. Deuterated chloroform ($CDCl_3$), methanol ($CD_3OD$) and water ($D_2O$) were obtained from Cambridge Isotope Laboratories. All reagents obtained from commercial suppliers were used without further purification unless otherwise noted. Analytical thin-layer chromatography was performed on E. Merck silica gel 60 $F_{254}$ plates. Compounds, which were not UV active, were visualized by dipping the plates in a ninhydrin or potassium permanganate solution and heating. Silica gel flash chromatography was performed using E. Merck silica gel (type 60SDS, 230-400 mesh). Solvent mixtures for chromatography are reported as v/v ratios. HPLC analysis was carried out on an Eclipse Plus $C_8$ analytical column with Phase A/Phase B gradients [Phase A: H$_2$O with 0.1% formic acid; Phase B: MeOH with 0.1% formic acid]. HPLC purification was carried out on Zorbax SB-C18 semipreparative column with Phase A/Phase B gradients [Phase A: H$_2$O with 0.1% formic acid; Phase B: MeOH with 0.1% formic acid]. Proton nuclear magnetic resonance ($^1$H NMR) spectra were recorded on a Varian VX-500 MHz or Jeol Delta ECA-500 MHz spectrometers, and were referenced relative to residual proton resonances in CDCl$_3$ (at 7.24 ppm) or CD$_3$OD (at 4.87 or 3.31 ppm). Chemical shifts were reported in parts per million (ppm, δ) relative to tetramethylsilane (δ 0.00). $^1$H NMR splitting patterns are assigned as singlet (s), doublet (d), triplet (t), quartet (q) or pentuplet (p). All first-order splitting patterns were designated on the basis of the appearance of the multiplet. Splitting patterns that could not be readily interpreted are designated as multiplet (m) or broad (br). Carbon nuclear magnetic resonance ($^{13}$C NMR) spectra were recorded on a Varian VX-500 MHz or Jeol Delta ECA-500 MHz spectrometers, and were referenced relative to residual proton resonances in CDCl$_3$ (at 77.23 ppm) or CD$_3$OD (at 49.15 ppm). Electrospray Ionization-Time of Flight (ESI-TOF) spectra were obtained on an Agilent 6230 Accurate-Mass TOFMS mass spectrometer. Spinning-disk confocal microscopy images were acquired on a Yokagawa spinning disk system (Yokagawa, Japan) built around an Axio Observer Z1motorized inverted microscope (Carl Zeiss Microscopy GmbH, Germany) with a 63×, 1.40 NA oil immersion objective to an Evolve 512×512 EMCCD camera (Photometrics, Canada) using ZEN imaging software (Carl Zeiss Microscopy GmbH, Germany). A condenser/objective with a phase stop of Ph2 was used to obtain the phase contrast images. The fluorophores were excited with a 561 nm, 40 mW DPSS laser (Texas Red®), and a 488 nm, 100 mW OPSL laser (Alexa Fluor® 488). Large vesicles were chosen to highlight the fluorescent membrane stain of the proteins. However, the mixtures consist of a heterogeneously sized population of vesicles with the majority being small vesicles.

Synthesis of Acyl Maltose Thioesters

Hepta-O-acetyl-(i-maltosyl Bromide (Compound No 7 in FIG. 7)[S1]

D-(+)-maltose monohydrate (5.00 g, 14.60 mmol) was treated with hydrobromic acid solution [33% in glacial acetic acid] (50 mL) at rt, and the reaction mixture was stirred for 2 h at rt. Afterwards, the mixture was diluted with chloroform (50 mL) and poured with stirring into ice-H$_2$O (100 mL). The CHCl$_3$ layer was separated and the aqueous layer extracted with CHCl$_3$ (3×75 mL). The CHCl$_3$ extracts were combined, washed with H$_2$O (3×75 mL) and NaHCO$_3$ (sat) (3×75 mL), and dried with Na$_2$SO$_4$. Removal of solvent in vacuo gave 3.80 g of 7 as an off-white foam [69%]. $^1$H NMR (CD$_3$OD, 500.13 MHz, δ): 6.50 (d, J=3.9 Hz, 1H, 1×CH), 5.61 (t, J=9.4 Hz, 3H, 3×CH), 5.41 (d, J=3.9 Hz, 2H, 2×CH), 5.38 (t, J=10.1 Hz, 3H, 3×CH), 5.07 (t, J=9.9 Hz, 3H, 3×CH), 4.86 (dd, J1=10.8 Hz, J2=3.9 Hz, 6H, 6×CH) 4.71 (dd, J1=9.7 Hz, J2=3.9 Hz, 6H, 6×CH), 4.55-4.49 (m, 4H, 2×CH+1×CH$_2$) 4.27-4.21 (m, 4H, 2×CH+1×CH$_2$), 4.08-4.02 (m, 6H, 2×CH+2×CH$_2$), 3.93 (dt, J1=6.9 Hz, J2=3.2 Hz, 3H, 3×CH), 2.13-1.99 (m, 21H, 7×CH$_3$)$^{13}$C NMR (CDCl$_3$, 500 MHz, δ): 170.8, 170.7, 170.0, 170.0, 169.7, 169.6, 95.9, 86.2, 72.7, 72.5, 71.7, 71.2, 70.2, 69.4, 68.8, 68.1, 62.0, 61.5, 60.5, 21.2, 21.0, 20.9, 20.8, 20.8, 20.7, 20.7. MS (ESI-TOF) [m/z (%)]: 697 ([M-H]−, 100).

Figure 7:
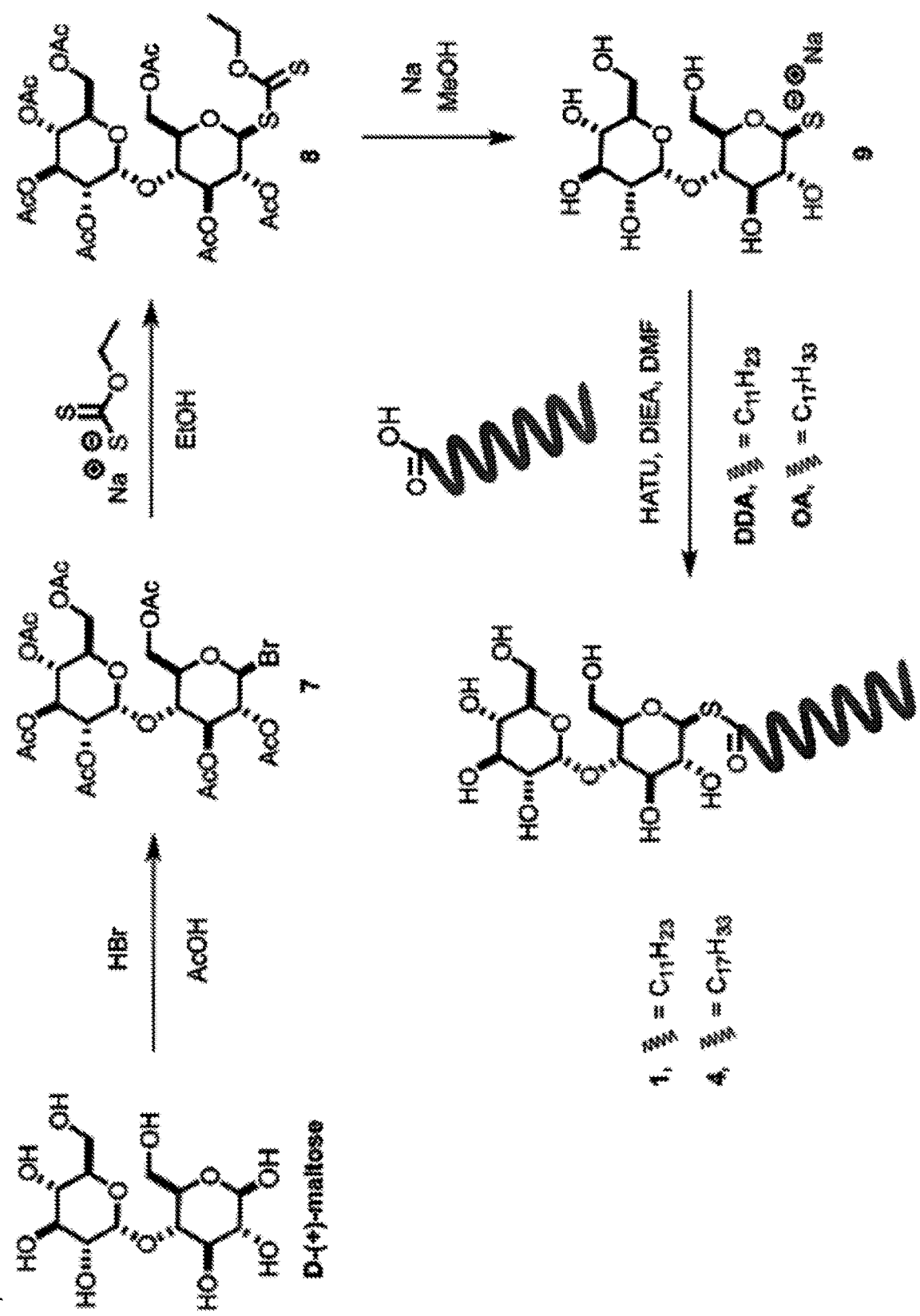
FIG. 7. Synthesis of acyl maltose thioesters [DDA: dodecanoic acid, OA: oleic acid].
Figure 8:
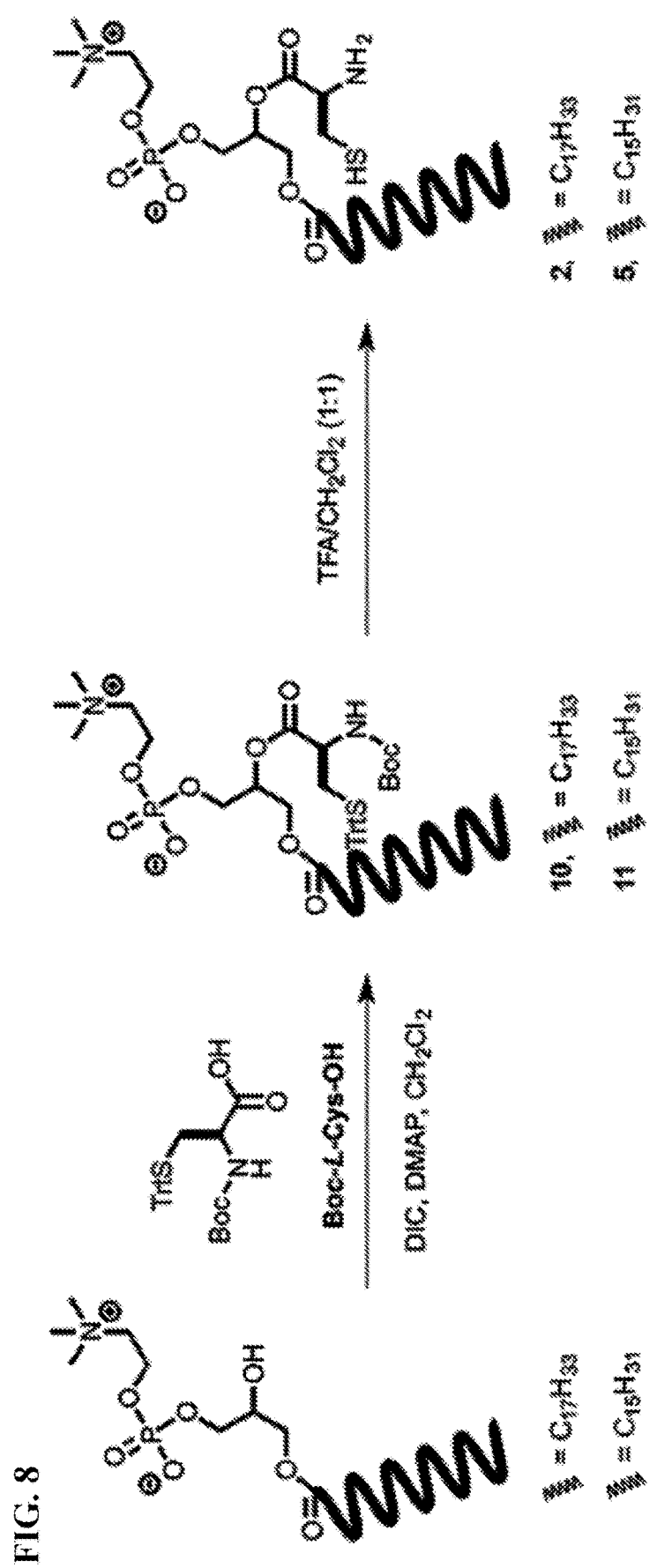
FIG. 8. Synthesis of cysteine-functionalized lysophospholipids.

Hepta-O-acetyl-β-maltosyl ethylxanthate (Compound No. 8 in FIG. 7)

[S2] To a solution of potassium ethylxanthate (1.00 g, 6.25 mmol) in EtOH (15 mL) was added hepta-O-acetyl-β-maltosyl bromide (7, 4.00 g, 5.60 mmol). The mixture was warmed for 5 min on a steam bath (80° C.) to effect dissolution, left to stand for 30 min at rt, and then poured into ice-H$_2$O (150 mL). The resulting powders were collected by filtration and air-dried, affording 1.74 g of 8 as a white foam [71%]. $^1$H NMR (CDCl$_3$, 500.13 MHz, δ): 5.49 (d, J=10.5 Hz, 1H, 1×CH), 5.41-5.31 (m, 3H, 3×CH), 5.09-4.97 (m, 2H, 2×CH), 4.85 (dd, J1=10.5 Hz, J2=4.0 Hz, 1H, 1×CH), 4.65 (q, J=7.1 Hz, 2H, 1×CH2), 4.43 (dd, J1=12.2 Hz, J2=2.7 Hz, 1H, 1×CH), 4.28-4.16 (m, 2H, 2×CH), 4.07-3.91 (m, 3H, 1×CH+1×CH$_2$), 3.86-3.77 (m, 1H, 1×CH), 2.11 (s, 3H, 1×CH$_3$), 2.08 (s, 3H, 1×CH$_3$), 2.04 (s, 3H, 1×CH$_3$), 2.01 (s, 3H, 1×CH$_3$), 2.00 (s, 6H, 2×CH$_3$), 1.99 (s, 3H, 1×CH$_3$), 1.42 (t, J=7.2 Hz, 3H, 1×CH$_3$). MS (ESI-TOF) [m/z (%)]: 739 ([M-H]−, 100).

1-thio-β-maltose Sodium Salt (Compound No. 9 in FIG. 7)[S2]

A solution of hepta-O-acetyl-β-maltosyl ethylxanthate (8, 1.20 g, 1.76 mmol) was cooled to −15° C. and treated, under stirring and cooling, with an equally cold methanolic solution (10 mL) of sodium methoxide containing 0.17 g of Na. The mixture became turbid as the reaction took place. Stirring and cooling were continued for 15 min. The resulting precipitate was collected by filtration, washed with CHCl$_3$, and dried in a vacuum desiccator to afford 0.52 g of 9 as a hygroscopic amorphous yellow powder [88%]. $^1$H NMR (D$_2$O, 500.13 MHz, δ): 5.52-5.35 (m, 1H, 1×CH), 4.48-4.34 (m, 1H, 1×CH), 4.02-3.92 (m, 1H, 1×CH), 3.91-3.82 (m, 1H, 1×CH), 3.82-3.54 (m, 8H, 4×CH+2×CH2), 3.50-3.37 (m, 1H, 1×CH), 3.36-3.25 (m, 1H, 1×CH). $^{13}$C NMR (D$_2$O, 125.77 MHz, δ): 103.0, 99.5, 76.7, 76.2, 74.5, 72.9, 72.6, 71.6, 69.3, 60.7, 60.4, 57.1. MS (ESI-TOF) [m/z (%)]: 357 ([M-H]−, 100). HRMS (ESI-TOF) calculated for C$_{12}$H$_{21}$O$_{10}$S ([M-H]−) 357.0861, found 357.0862.

Dodecanoyl Maltose Thioester (Compound No. 1 in FIGS. 1B, 5, 6, 7, and 9)

A solution of dodecanoic acid (263.3 mg, 131.5 μmol) in DMF (500 μL) was stirred at 0° C. for 10 min, and then HATU (55.0 mg, 144.6 μmol) and DIEA (25.2 μL, 144.6 μmol) were successively added. After 10 min stirring at 0° C., 1-thio-β-maltose sodium salt (9, 50.0 mg, 131.5 μmol) was added. After 1 h stirring at rt, the mixture was concentrated under reduced pressure. The corresponding residue was diluted in MeOH (500 μL), filtered using a 0.2 m syringe-driven filter, and the crude solution was purified by HPLC, affording 45.3 mg of 1 as a white solid [64%, tR=4.7 min (Zorbax SB-C$_{18}$ semipreparative column, 5% Phase A in Phase B, 15.5 min)]. $^1$H NMR (CD$_3$OD, 500.13 MHz, δ): 5.18 (d, J=3.9 Hz, 1H, 1×CH), 5.06 (d, J=10.3 Hz, 1H, 1×CH), 3.87-3.77 (m, 3H, 3×CH), 3.72-3.56 (m, 5H, 1×CH+2×CH$_2$), 3.49-3.42 (m, 2H, 2×CH), 3.38-3.33 (m, 1H, 1×CH), 3.29-3.23 (m, 1H, 1×CH), 2.69-2.54 (m, 2H, 1×CH$_2$), 1.75-1.56 (m, 2H, 1×CH$_2$), 1.43-1.19 (m, 16H, 8×CH$_2$), 0.90 (t, J=7.0 Hz, 3H, 1×CH$_3$). $^{13}$C NMR (CD$_3$OD, 125.77 MHz, δ): 198.6, 102.9, 83.9, 81.1, 80.6, 79.5, 75.1, 74.8, 74.2, 72.9, 71.5, 62.8, 62.0, 45.1, 33.1, 30.7, 30.7, 30.5, 30.5, 30.4, 30.0, 26.4, 23.7, 14.4. MS (ESI-TOF) [m/z (%)]: 540 ([MH]+, 25), 563 ([M+Na]+, 100). HRMS (ESI-TOF) calculated for $C_{24}H_{44}O_{11}SNa$ ([M+Na]+) 563.2497, found 563.2499.

Oleoyl maltose thioester (Compound No. 4 in FIGS. 1B, 5, 6, 7, and 9). A solution of oleic acid (36.3 mg, 131.5 μmol) in DMF (500 μL) was stirred at 0° C. for 10 min, and then HATU (55.0 mg, 144.6 μmol) and DIEA (25.2 μL, 144.6 μmol) were successively added. After 10 min stirring at 0° C., 1-thio-β-maltose sodium salt (9, 50.0 mg, 131.5 μmol) was added. After 1 h stirring at rt, the mixture was concentrated under reduced pressure. The corresponding residue was diluted in MeOH (500 μL), filtered using a 0.2 μm syringe-driven filter, and the crude solution was purified by HPLC, affording 48.8 mg of 4 as a white solid [58%, tR=7.0 min (Zorbax SB-C18 semipreparative column, 5% Phase A in Phase B, 15.5 min)]. $^1$H NMR (CD$_3$OD, 500.13 MHz, δ): 5.36-5.32 (m, 6H, 2×CH+2×CH$_2$), 5.18 (d, J=3.8 Hz, 1H, 1×CH), 5.06 (d, J=10.2 Hz, 1H, 1×CH), 4.84 (d, J=17.2 Hz, 1H, 1×CH) 3.86-3.79 (m, 2H, 2×CH), 3.71-3.58 (m, 5H, 1×CH+2×CH$_2$), 3.47-3.42 (m, 2H, 2×CH), 3.37-3.24 (m, 1H, 1×CH$_2$), 2.63-2.59 (m, 2H, 1×CH$_2$), 2.03 (q, J=6.1 Hz, 2H, 1×CH$_2$), 1.65 (q, J=7.2 Hz, 4H, 2×CH$_2$), 1.33 (dd, J1=20.1 Hz, J2=11.5 Hz, 16H, 8×CH$_2$), 0.90 (t, J=6.9 Hz, 3H, 1×CH$_3$). $^{13}$C NMR (CD$_3$OD, 125.77 MHz, δ): 197.1, 129.4, 129.3, 101.4, 82.4, 79.6, 79.1, 78.0, 73.6, 73.3, 72.8, 71.5, 70.1, 48.1, 47.0, 43.6, 31.6, 29.4, 29.3, 29.1, 29.0, 28.9, 28.8, 28.7, 28.5, 26.7, 26.6, 24.9, 22.3, 13.0. MS (ESI-TOF) [m/z (%)]: 621 ([M-H]−, 100). HRMS (ESI-TOF) calculated for $[C_{24}H_{44}O_{11}S]$ ([M-H]−) 621.3314, found 621.3317.

Synthesis of Lysophospholipids 1-oleoyl-2-[N-Boc-L-Cys(Trt)]-sn-glycero-3-phosphocholine (Compound No. 10 in FIG. 8)[S3]

A solution of N-Boc-L-Cys(Trt)-OH (88.9 mg, 191.7 μmol) in CH$_2$Cl$_2$ (7.5 mL) was stirred at rt for 10 min, and then DIC (45.0 μL, 287.5 μmol) and DMAP (11.7 mg, 95.8 μmol) were successively added. After 10 min stirring at rt, 1-oleoyl-2-hydroxy-sn-glycero-3-phosphocholine (25.0 mg, 47.9 μmol) was added. After 12 h stirring at rt, the solvent was removed under reduced pressure, and the crude was purified by HPLC, affording 34.6 mg of 10 as a colorless foam [75%, tR=7.8 min (Zorbax SB-C18 semipreparative column, 100% Phase B, 15.5 min)]. $^1$H NMR (CDCl$_3$, 500.13 MHz, δ): 7.38 (d, J=7.5 Hz, 6H, 6×CHAr), 7.33-7.26 (m, 6H, 6×CHAr), 7.25-7.19 (m, 3H, 3×CHAr), 5.40-5.29 (m, 2H, 2×CH), 5.27-5.13 (m, 1H, 1×CH), 5.07 (d, J=9.0 Hz, 1H, 1×NH), 4.41-3.88 (m, 7H, 3×CH$_2$+1×CH), 3.77-3.57 (m, 2H, 1×CH$_2$), 3.25 (s, 9H, 3×CH$_3$), 2.74-2.48 (m, 2H, 1×CH$_2$), 2.31-2.09 (m, 2H, 1×CH$_2$), 2.07-1.93 (m, 4H, 2×CH$_2$), 1.61-1.43 (m, 2H, 1×CH$_2$), 1.42 (s, 9H, 3×CH$_3$), 1.31-1.17 (m, 20H, 10×CH$_2$), 0.88 (t, J=7.0 Hz, 3H, 1×CH$_3$). $^{13}$C NMR (CDCl$_3$, 125.77 MHz, δ): 173.5, 170.4, 163.9, 155.3, 144.4, 130.1, 129.9, 129.7, 129.6, 128.2, 128.2, 127.1, 80.1, 72.3, 67.2, 66.5, 63.8, 62.7, 59.4, 54.6, 52.7, 34.1, 34.1, 34.0, 32.0, 29.9, 29.9, 29.7, 29.5, 29.5, 29.4, 29.4, 29.3, 29.2, 29.2, 28.5, 28.5, 27.4, 27.3, 24.9, 24.8, 22.8, 14.3. MS (ESI-TOF) [m/z (%)]: 967 ([MH]+, 100), 989 ([M+Na]+, 20). HRMS (ESI-TOF) calculated for $C_{53}H_{80}N_2O_{10}PS$ ([MH]+) 967.5266, found 967.5269.

1-oleoyl-2-(L-Cys)-sn-glycero-3-phosphocholine (Compound No. 2 in FIGS. 1B, 5, 6, 8, and 9)[S3]

A solution of 1-oleoyl-2-[N-Boc-L-Cys(Trt)]-sn-glycero-3-phosphocholine (10, 10.0 mg, 10.3 μmol) in 2 mL of TFA/CH$_2$Cl$_2$/TES (0.9:0.9:0.2) was stirred at rt for 30 min. After removal of the solvent, the residue was dried under high vacuum for 3 h. Then, the corresponding residue was diluted in MeOH (500 μL), filtered using a 0.2 μm syringe-driven filter, and the crude solution was purified by HPLC, affording 5.1 mg of the lysophospholipid 2 as a colorless foam [79%, tR=8.6 min (Zorbax SB-C18 semipreparative column, 50% Phase A in Phase B, 5 min, and then 5% Phase A in Phase B, 10 min)]. $^1$H NMR (CD$_3$OD, 500.13 MHz, δ): 5.46-5.26 (m, 3H, 3×CH), 4.49-4.35 (m, 1H, 1×CH), 4.34-4.19 (m, 3H, 1.5×CH$_2$), 4.16-3.99 (m, 3H, 1.5×CH$_2$), 3.72-3.59 (m, 2H, 1×CH$_2$), 3.29-3.26 (m, 1H, 0.5×CH$_2$), 3.23 (s, 9H, 3×CH$_3$), 3.19-3.00 (m, 1H, 0.5×CH$_2$), 2.35 (t, J=6.7 Hz, 2H, 1×CH$_2$), 2.09-1.90 (m, 4H, 2×CH$_2$), 1.69-1.53 (m, 2H, 1×CH$_2$), 1.41-1.22 (m, 20H, 10×CH$_2$), 0.90 (t, J=6.7 Hz, 3H, 1×CH$_3$). $^{13}$C NMR (CD$_3$OD, 125.77 MHz, δ): 174.9, 172.3, 131.6, 130.8, 73.7, 67.4, 64.9, 63.4, 63.2, 60.6, 54.6, 34.9, 33.7, 33.1, 30.8, 30.8, 30.7, 30.6, 30.5, 30.4, 30.3, 30.3, 30.2, 28.1, 26.0, 23.8, 14.5. MS (ESI-TOF) [m/z (%)]: 625 ([MH]+, 100). HRMS (ESI-TOF) calculated for C29H58N2O8PS ([MH]+) 625.3651, found 625.3647.

1-palmitoyl-2-[N-Boc-L-Cys(Trt)]-sn-glycero-3-phosphocholine (Compound No. 11 in FIG. 8)[S3-S5]

A solution of N-Boc-L-Cys(Trt)-OH (93.7 mg, 201.6 μmol) in CH$_2$Cl$_2$ (7.5 mL) was stirred at rt for 10 min, and then DIC (47.0 μL, 302.4 μmol) and DMAP (12.3 mg, 100.8 μmol) were successively added. After 10 min stirring at rt, 1-palmitoyl-2-hydroxy-sn-glycero-3-phosphocholine (25.0 mg, 50.4 μmol) was added. After 12 h stirring at rt, the solvent was removed under reduced pressure, and the crude was purified by HPLC, affording 29.6 mg of 11 as a colorless foam [88%, Rt=12.5 min (Zorbax SB-C18 semipreparative column, 5% Phase A in Phase B, 15.5 min)]. $^1$H NMR (CDCl$_3$, 500.13 MHz, δ): 7.38-7.31 (d, J=8.0 Hz, 6H, 6×CHAr), 7.30-7.23 (m, 6H, 6×CHAr), 7.22-7.16 (m, 3H, 3×CHAr), 5.25-5.13 (m, 1H, 1×CH), 5.10 (d, J=7.8 Hz, 0.3H, 1×NH), 5.01 (d, J=7.8 Hz, 0.7H, 1×NH), 4.38-4.21 (m, 3H, 1.5×CH$_2$), 4.20-4.11 (m, 1H, 1×CH), 4.10-3.87 (m, 3H, 1.5×CH$_2$), 3.86-3.66 (m, 2H, 1×CH$_2$), 3.25 (s, 9H, 3×CH$_3$), 2.73-2.45 (m, 2H, 1×CH$_2$), 2.33-2.06 (m, 2H, 1×CH$_2$), 1.62-1.43 (m, 2H, 1×CH$_2$), 1.38 (s, 9H, 3×CH$_3$), 1.31-1.16 (m, 24H, 12×CH$_2$), 0.85 (t, J=7.0 Hz, 3H, 1×CH$_3$). $^{13}$C NMR (CDCl3, 125.77 MHz, δ): 173.6, 170.4, 163.9, 155.3, 144.5, 129.7, 128.3, 121.2, 80.2, 72.2, 67.3, 66.4, 64.1, 62.6, 59.9, 54.7, 52.8, 34.2, 34.1, 32.1, 29.9, 29.9, 29.9, 29.7, 29.6, 29.5, 29.4, 29.3, 28.6, 24.9, 22.9, 14.3. MS (ESI-TOF) [m/z (%)]: 941 ([MH]+, 100). HRMS (ESI-TOF) calculated for C51H78N2O10PS ([MH]+) 941.5109, found 941.5111.

1-palmitoyl-2-(L-Cys)-sn-glycero-3-phosphocholine (Compound No. 5 in FIGS. 1B, 5, 6, 8, and 9)[S3-S5]

A solution of 1-pal-mitoyl-2-[N-Boc-L-Cys(Trt)]-sn-glycero-3-phosphocholine (11, 30.0 mg, 31.9 μmol) in 6 mL of TFA/CH$_2$Cl$_2$/TES (2.85:2.85:0.3) was stirred at rt for 30 min. After removal of the solvent, the residue was dried under high vacuum for 3 h. Then, the corresponding residue was diluted in MeOH (1 mL), filtered using a 0.2 μm syringe-driven filter, and the crude solution was purified by HPLC, affording 14.2 mg of the lysophospholipid 5 as a colorless foam [64%, Rt=9.0 min (Zorbax SB-C18 semipreparative column, 50% Phase A in Phase B, 5 min, and then 5% Phase A in Phase B, 10 min)]. $^1$H NMR (CD$_3$OD, 500.13 MHz, δ): 5.37 (m, 1H, 1×CH), 4.43-4.36 (m, 1H, 0.5×CH$_2$), 4.35-4.28 (m, 1H, 1×CH), 4.27-4.14 (m, 3H, 1.5×CH$_2$), 4.13-3.98 (m, 2H, 1×CH$_2$), 3.63-3.56 (m, 2H, 1×CH$_2$), 3.17 (s, 9H, 3×CH$_3$), 3.16-2.99 (m, 2H, 1×CH$_2$), 2.33-2.25 (m, 2H, 1×CH$_2$), 1.60-1.49 (m, 2H, 1×CH$_2$), 1.31-1.19 (m, 24H, 12×CH$_2$), 0.84 (t, J=6.9 Hz, 3H, 1×CH$_3$). $^{13}$C NMR (CD$_3$OD, 125.77 MHz, δ): 175.0, 168.5, 75.0, 67.5, 65.1, 63.3, 60.7, 55.9, 54.8, 34.9, 33.2, 31.0, 31.0, 30.9, 30.9, 30.9, 30.8, 30.7, 30.6, 30.4, 26.1, 25.5, 25.3, 23.9, 14.6. MS (ESI-TOF) [m/z (%)]: 599 ([MH]+, 100). HRMS (ESI-TOF) calculated for C$_{27}$H$_{56}$N$_2$O$_8$PS ([MH]+) 599.3490, found 599.3484.

Synthesis of Phospholipids 1-oleoyl-2-[L-Cys-(dodecanoyl)]-sn-glycero-3-phosphocholine (Compound No. 3 in FIGS. 1B, 5, 6, and 9)

1-oleoyl-2-(L-Cys)-sn-glycero-3-phosphocholine (2, 2.50 mg, 4.00 μmol) and dodecanoyl maltose thioester (1, 2.16 mg, 4.00 μmol) were dissolved in 800 L of 25 mM DTT in 200 mM NaH$_2$PO$_4$.H$_2$O pH 7.1 buffer and stirred under N$_2$ at rt. After 30 min, the corresponding mixture was filtered using a 0.2 μm syringe-driven filter, and the crude solution was purified by HPLC, affording 1.7 mg of the amidophospholipid 3 as a colorless film [53%, tR=9.1 min (Zorbax SB-C18 semipreparative column, 100% Phase B, 20.5 min)]. MS (ESI-TOF) [m/z (%)]: 807 ([MH]+, 100), 829 ([M+Na]+, 45). HRMS (ESI-TOF) calculated for C$_{41}$H$_{80}$N$_2$O$_9$PS ([MH]+) 807.5322, found 807.5325.

1-palmitoyl-2-[L-Cys-(oleoyl)]-sn-glycero-3-phosphocholine (Compound No. 6 in FIGS. 1B, 5, 6, and 9)[S3-S5]

1-palmitoyl-2-(L-Cys)-sn-glycero-3-phosphocholine (5, 2.50 mg, 3.60 μmol) and oleoyl maltose thioester (4, 2.23 mg, 3.60 μmol) were dissolved in 800 L of 25 mM DTT in 200 mM NaH$_2$PO$_4$.H$_2$O pH 7.1 buffer and stirred under N$_2$ at rt. After 30 min, the corresponding mixture was filtered using a 0.2 μm syringe-driven filter, and the crude solution was purified by HPLC, affording 2.0 mg of the amidophospholipid 6 as a colorless film [68%, tR=12.7 min (Zorbax SB-C18 semipreparative column, 100% Phase B, 15.5 min)]. $^1$H NMR (CDCl$_3$, 500.13 MHz, δ): 6.87 (d, 1H, 1×NH, J=7.5 Hz), 5.37-5.29 (m, 2H, 2×CH), 5.28-5.18 (m, 1H, 1×CH), 4.88-4.77 (m, 1H, 1×CH), 4.46-4.24 (m, 3H, 1.5×CH$_2$), 4.23-3.99 (m, 3H, 1.5×CH$_2$), 3.98-3.80 (m, 2H, 1×CH$_2$), 3.36 (s, 9H, 3×CH$_3$), 3.08-2.81 (m, 2H, 1×CH$_2$), 2.34-2.17 (m, 4H, 2×CH$_2$), 2.04-1.87 (m, 4H, 2×CH$_2$), 1.67-1.48 (m, 4H, 2×CH$_2$), 1.35-1.16 (m, 45H, 22×CH$_2$+1× SH), 0.85 (t, J=6.8 Hz, 6H, 2×CH$_3$). 13C NMR (CDCl$_3$, 125.77 MHz, δ): 173.7, 169.9, 163.5, 130.7 and 130.4, 130.2 and 129.9, 72.3, 66.3, 64.6, 62.4, 60.2, 54.7, 53.7, 36.5, 34.2, 32.9, 32.1, 30.0, 29.9, 29.9, 29.9, 29.8, 29.7, 29.6, 29.6, 29.6, 29.5, 29.4, 29.4, 29.3, 27.4, 26.9, 25.9, 25.0, 22.9, 14.4. MS (ESI-TOF) [m/z (%)]: 885 ([M+Na]+, 60), 863 ([MH]+, 100). HRMS (ESI-TOF) calculated for C$_{45}$H$_{88}$N$_2$O$_9$PS ([MH]+) 863.5943, found 863.5948.

De Novo Phospholipid Synthesis: In Situ Vesicle Formation 5.0 μL of a 25 mM DTT solution in 200 mM NaH$_2$PO$_4$ pH 7.1 buffer were added to 2.5 μL of a 10 mM solution of cysteine-based lysophospholipid 2 in 200 mM NaH$_2$PO$_4$ pH 7.1 buffer. Afterward, 2.5 μL of a 10 mM solution of dodecanoyl maltose thioester 1 in NaH$_2$PO$_4$ pH 7.1 buffer were added, and the mixture was briefly agitated. The resulting solution was added to a glass microscope slide and covered with a glass coverslip supported with vacuum grease. The sample was then monitored by phase contrast microscopy in order to analyze the in situ phospholipid 3 vesicle formation.

LC/MS Analysis

De novo formation (NCL reaction) of phospholipid membranes was performed in the appropriate buffer (200 mM NaH$_2$PO$_4$ pH 7.1 buffer containing 25 mM DTT) as described above. Aliquots of 1.5 μL of sample were taken at various time points, diluted with 50.0 μL of MeOH and analyzed using an Eclipse Plus C$_8$ analytical column (5% Phase A in Phase B, 5.5 min) with an Evaporative Light Scattering Detector (ELSD) at a flow of 1.0 mL/min. For all LC/MS runs, solvent Phase A consisted of H$_2$O with 0.1% formic acid and solvent Phase B of MeOH with 0.1% formic acid.

A$_{2A}$ Expression and Purification

A$_{2A}$ construct design, expression and purification was performed as previously described.[S6]

Reconstitution of A$_{2A}$ in HDL

Purified A$_{2A}$ receptor was reconstituted into high density lipid containing apoA-1 particles similarly as described with β2AR-HDL reconstitution.[S7] A 200 μL HDL-A$_{2A}$ recon was prepared from 1-palmitoyl-2-oleoyl-sn-glycero-3-phosphocholine (POPC) and 1-palmitoyl-2-oleoyl-sn-glycero-3-phosphoglycerol (POPG) with a 3:2 molar ratio, respectively. Briefly, 0.78 μmol POPC and 0.52 μmol POPG in CHCl$_3$ were aspirated in a glass tube and house vacuum until dry. The remaining residue was then re-dissolved into a 19.5 mM cholate containing-HNE buffer. After chilling on ice for 10 min., 20.0 nmol of purified apoA-1 (0.1 mM, final) along with 2.0 nmol purified A$_{2A}$ dissolved in 0.1% MNG and 0.02% CHS were added to the mixture. The remaining solution, 200 μL total, was allowed to rest for 1 h before transferring to an equal volume of prepared Bio-Beads (200 μL) to equilibrate at 4° C. overnight with gentle agitation. The final concentration of A$_{2A}$ in HDL was estimated via total specific binding using [$^3$H]-ZM241385 (10 nM).

Detergent Exchange of A$_{2A}$

DDM was exchanged for the reactive thioesters (1 or 4), by using a 10 kDa-cutoff spin column (Millipore). The A$_{2A}$ was concentrated by two-fold, followed by a two-fold dilution with 20 mM HEPES buffer, pH 7.4 containing 100 mM NaCl, 20 mM DTT, 1.5 mM maltose thioester (1 or 4). This was repeated up to 6× at 10,000 rcf.

Reconstitution of purified A$_{2A}$ into NCL-based proteoliposomes A$_{2A}$/3

100 μl of micelle-solubilized protein (A$_{2A}$/1), with a final concentration of dodecanoyl maltose thioester 1 of 1.5 mM, was reacted with 50.0 μl (1.5 mM final concentration) of cysteine-functionalized lysophospholipid 2 in the presence of 20 mM HEPES buffer, pH 7.4 containing 100 mM NaCl and 20 mM DTT for 20 min at rt. After this time, formation of A$_{2A}$/3 proteoliposomes was observed.

A$_{2A}$ Fluorescent Labeling

A$_{2A}$ was labeled using 5 equivalents of Alexa Fluor® 488 NHS ester in 20 mM sodium bicarbonate, pH 8.2, 100 mM NaCl and 0.1% DDM for 1 h at rt. The modified protein was then dialyzed overnight in 20 mM HEPES, pH 7.5 buffer, 100 mM NaCl and 0.1% DDM. Then, it was followed by DDM exchange for 1.5 mM of compound 1. After visualization of liposome formation, Texas Red® DHPE, at a final concentration of 0.5 mol % was added to observe co-localization with the modified A$_{2A}$/3 proteoliposomes.

Saturation Binding

Reconstituted $A_{2A}$ HDL or $A_{2A}$ NCL-based liposome specific binding saturation experiments were performed in triplicates incubated at 25° C. over 1.5 h prepared in 96-well plates in 200.0 or 500.0 μL volumes using [$^3$H]-NECA (0.001-10.0 μM final (cold+$^3$H ligand))/($A_{2A}$HDL only) or [$^3$H]-ZM241385 (0.01-100.0 nM final (cold+$^3$H ligand)) in 50 mM Tris, 150 mM NaCl, pH 7.6 (TBS). Specific binding was calculated from total binding—nonspecific binding as determined with competing 5.0 μM unlabeled ZM241385.

NECA/[$^3$H]-ZM241385 competition

Ligand competition with $A_{2A}$ reconstituted synthetic liposomes was completed in 96 well plates in 200 μL volume triplicates using [$^3$H]-ZM241385 at 2.0 nM and NECA (0.0003-30 μM) over 1.5 h incubations at 25° C. in 25 mM Tris, 150 mM NaCl, pH 7.6 (TBS). Specific binding was determined from total binding (2 nM [$^3$H]-ZM241385) using 5 μM unlabeled ZM241385.

In some embodiments, membrane proteins are key regulators of communication between cellular compartments, functioning primarily as receptors and transporters. They may also determine the distinctive architecture and adhesion properties of cells. Loss of their function may lead to numerous disease states, including metabolic dysfunction, neurodegenerative diseases, and cardiovascular diseases. Although the proteome is comprised of approximately 25% membrane proteins, less than 1% have known structures in the Protein Data Bank. The lack of structural insight is a major challenge associated with the study of membrane proteins and has motivated the need to develop additional characterization tools.

A transmembrane protein reconstitution using CuACC precursors; oleoyl azide/alkyne lysophosphatidylcholine and the NCL precursors; cysteine lysolipid/thioester was demonstrated. However, both employ a lysophospholipid mimic acting as the detergent to solubilize the membrane proteins. This may be less than ideal considering lysophospholipids, in general, may be poor detergents for the isolation of membrane proteins. Their cmc ranges between 4-20 uM; this low cmc may result in their intrinsic ability to make micelles before fully solubilizing the protein. As a consequence, in some embodiments, this may require excess lysophospholipid to saturate the binding capacity of the protein in order to obtain micelle-solubilized protein. Furthermore, if the lysophospholipid's head group is ionic or zwitterionic it may have a greater potential of denaturing a protein o interest, thereby abolishing its native function. N-dodecyl-β-D-maltoside (DDM) is a glycosidic surfactant, increasingly employed in transmembrane protein isolations, especially when protein activity needs to be preserved. It was previously demonstrated to be more efficient than CHAPS, or NP-40. Correspondingly, a DDM thioester precursor to be utilized with the NCL methodology (FIGS. 10A-10E) was designed to achieve high yielding protein reconstitution by improving both the solubilization and stability of the membrane proteins.

REFERENCES (EXAMPLE 1)

[1] Katritch, V.; Cherezov, V.; Stevens, R. C. Annu. Rev. Pharmacol. Toxicol. 2013, 53, 531; [2] Salon, J. A.; Lodowski, D. T.; Palczewski, K. Pharmacol. Rev. 2011, 63, 901; [3] Pierce, K. L.; Premont, R. T.; Lefkowitz, R. J. Nat. Rev. Mol. Cell Biol. 2002, 3, 639; [4] Kobilka, B. K. Biochim. Biophys. Acta 2007, 1768, 794; [5] Magalhaes, A. C.; Dunn, H.; Ferguson, S. S. G. Br. J. Pharmacol. 2012, 165, 1717; [6] Grisshammer, R. Methods Enzymol. 2009, 463, 631; [7] Bocquet, N.; Kohler, J.; Hug, M. N.; Kusznir, E. A.; Rufer, A. C.; Dawson, R. J.; Hennig, M.; Ruf, A.; Huber, W.; Huber, S. Biochim. Biophys. Acta—Biomembranes 2015, 1848, 1224; [8] Whorton, M. R.; Bokoch, M. P.; Rasmussen, S. G. F.; Huang, B.; Zare, R. N.; Kobilka, B.; Sunahara, R. K. Proc. Natl. Acad. Sci. USA 2007, 104, 7682; [9] Cole, C. M.; Brea, R. J.; Kim, Y. H.; Hardy, M. D.; Yang, J.; Devaraj, N. K. Angew. Chem. Int. Ed. 2015, 54, 12738; [10] Bhamidipati, S. P.; Hamilton, J. A. Biochemistry 1995, 34, 5666; [11] Stangl, M.; Veerappan, A.; Kroeger, A.; Vogel, P.; Schneider, D. Biophys. J. 2012, 103, 2455; [12] Seddon, A. M.; Curnow, P.; Booth, P. J. Biochim. Biophys. Acta 2004, 1666, 105; [13] O'Malley, M. A.; Helgeson, M. E.; Wagner, N. J.; Robinson, A. S. Biophys. J. 2011, 101, 1938; [14] Lipfert, J.; Columbus, L.; Chu, V. B.; Lesley, S. A.; Doniach, S. J. Phys. Chem. B 2007, 111, 12427; [15] Gutmann, D. A.; Mizohata, E.; Newstead, S.; Ferrandon, S.; Postis, V.; Xia, X.; Henderson, P. J.; van Veen, H. W.; Byrne, B. Protein Sci. 2007, 16, 1422; [16] Thompson, A. A.; Liu, J. J.; Chun, E.; Wacker, D.; Wu, H.; Cherezov, V.; Stevens, R. C. Methods 2011, 55, 310; [17] Rosevear, P.; VanAken, T.; Baxter, J.; Ferguson-Miller, S. Biochemistry 1980, 19, 4108; [18] Klammt, C.; Schwarz, D.; Fendler, K.; Haase, W.; Dotsch, V.; Bernhard, F. FEBS J. 2005, 272, 6024; [19] Privé, G. G. Methods 2007, 41, 388; [20] Dawson, P. E.; Muir, T. W.; Clark-Lewis, I.; Kent, S. B. H. Science 1994, 266, 776; [21] Mitra, N.; Liu, Y.; Liu, J.; Serebryany, E.; Mooney, V.; DeVree, B. T.; Sunahara, R. K.; Yan, E. C. ACS Chem. Biol. 2013, 8, 617; [22] Vélez-Ruiz, G. A.; Sunahara, R. K. Methods Mol. Biol. 2011, 756, 167; [23] Gao, Z.-G.; Jiang, Q.; Jacobson, K. A.; Ijzerman, A. P. Biochem. Pharmacol. 2000, 60, 661; [24] Bosch, M. P.; Campos, F.; Niubó, I.; Rosell, G.; Diaz, J. L.; Brea, J.; Loza, M. I.; Guerrero, A. J. Med. Chem. 2004, 47, 4041; [25] Schuler, M. A.; Denisov, I. G.; Sligar, S. G. Methods Mol. Biol. 2013, 974, 415. [S1] Scheurer, P. G.; Smith, F. J. Am. Chem. Soc. 1954, 76, 3224. [S2] Mori, M.; Haga, M.; Tejima, S. Chem. Pharm. Bull. 1974, 22, 1331. [S3] Brea, R. J.; Rudd, A. K.; Devaraj, N. K. Proc. Natl. Acad. Sci. U.S.A. 2016, 113, 8589. [S4] Brea, R. J.; Cole, C. M.; Devaraj, N. K. Angew. Chem. Int. Ed. 2014, 53, 14102. [S5] Cole, C. M.; Brea, R. J.; Kim, Y. H.; Hardy, M. D.; Yang, J.; Devaraj, N. K. Angew. Chem. Int. Ed. 2015, 54, 12738. [S6] Ye, L.; Van Eps, N.; Zimmer, M; Ernst, O. P.; Prosser, R. S. Nature 2016, 533, 265. [S7] Whorton, M. R.; Bokoch, M. P.; Rasmussen, S. G. F.; Huang, B.; Zare, R. N.; Kobilka, B.; Sunahara, R. K. Proc. Natl. Acad. Sci. USA 2007, 104, 7682.

What is claimed is:

1. A method for forming a lipid membrane comprising a membrane protein, the method comprising:
    adding a reactive maltoside surfactant comprising a reactive thioester moiety to a first solution which comprises the membrane protein; thereby forming a second solution which comprises the reactive maltoside surfactant and the membrane protein; and
    (ii) adding a cysteine-functionalized phosphatidylcholine compound to the second solution, thereby forming a synthetic phospholipid; wherein the synthetic phospholipid forms a lipid membrane comprising the membrane protein.

2. The method of claim 1, comprising solubilizing the membrane protein in a first surfactant to form the first solution.

3. The method of claim 2, wherein the first surfactant is a nonionic alkyl glucoside.

4. The method of claim 2, wherein the first surfactant is n-dodecyl-β-D-maltoside.

5. The method of claim 1, wherein the said reactive maltoside surfactant has the formula:

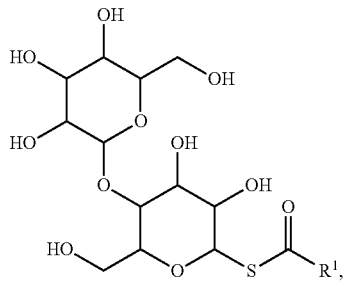

wherein $R^1$ is a substituted or unsubstituted alkyl.

6. The method of claim 1, wherein the cysteine-functionalized phosphatidylcholine compound is a cysteine-functionalized oleoyl lysophosphatidylcholine compound or a cysteine-functionalized palmitoyl lysophosphatidylcholine compound.

7. The method of claim 1, wherein the cysteine-functionalized phosphatidylcholine compound has the formula:

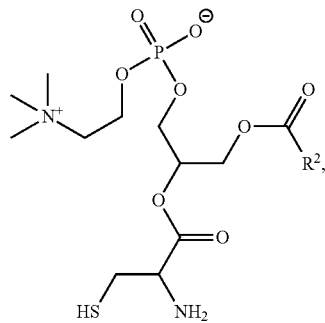

wherein $R^2$ is a substituted or unsubstituted alkyl.

8. The method of claim 7, wherein $R^2$ is an unsubstituted $C_4$-$C_{20}$ alkyl or an unsubstituted $C_6$-$C_{18}$ alkenyl.

9. The method of claim 1, wherein the synthetic phospholipid has the formula:

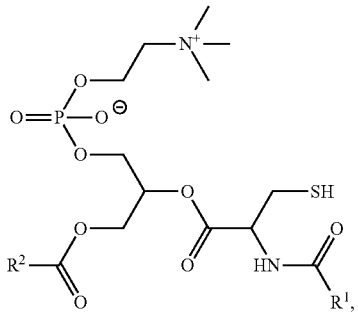

wherein $R^1$ is a substituted or unsubstituted alkyl.

10. The method of claim 9, wherein $R^1$ is an unsubstituted $C_4$-$C_{20}$ alkyl or an unsubstituted $C_6$-$C_{18}$ alkenyl.

11. The method of claim 1, wherein the membrane protein is a G protein-coupled receptor.

12. The method of claim 1, wherein the membrane protein is a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

13. The method of claim 1, wherein the lipid membrane is a liposome.

14. The method of claim 1, wherein the molar ratio of the membrane protein to the synthetic phospholipid is from about 0.1:1 to about 1:600.

15. A liposome produced by the method of claim 1.

* * * * *